US009477811B2

(12) United States Patent
Drucker et al.

(10) Patent No.: US 9,477,811 B2
(45) Date of Patent: *Oct. 25, 2016

(54) BLOOD GLUCOSE TRACKING APPARATUS AND METHODS

(75) Inventors: Steven Drucker, Oakland, CA (US); Charles T. Liamos, Pleasanton, CA (US); Fredric C. Colman, Oakland, CA (US); Mark Lortz, Pleasanton, CA (US); Kelley Lipman, Livermore, CA (US); Feng Jiang, Union City, CA (US); Henrik Bacho, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1482 days.

This patent is subject to a terminal disclaimer.

(21) Appl. No.: 11/160,427

(22) Filed: Jun. 23, 2005

(65) Prior Publication Data
US 2005/0239156 A1  Oct. 27, 2005

Related U.S. Application Data

(62) Division of application No. 10/112,671, filed on Mar. 29, 2002, now Pat. No. 7,041,468.

(60) Provisional application No. 60/300,011, filed on Jun. 20, 2001, provisional application No. 60/280,905, filed on Apr. 2, 2001.

(51) Int. Cl.
*G01N 33/48* (2006.01)
*G01N 31/00* (2006.01)
(Continued)

(52) U.S. Cl.
CPC ........... *G06F 19/3418* (2013.01); *A61B 5/743* (2013.01); *G01N 33/48778* (2013.01);
(Continued)

(58) Field of Classification Search
CPC .......... A61B 2562/0295; A61B 5/743; A61B 5/14532; G06Q 50/22; G01N 33/48792; G01N 33/96
See application file for complete search history.

(56) References Cited

U.S. PATENT DOCUMENTS 2,402,306 A  6/1946  Turkel
3,132,123 A  5/1964  Harris, Jr. et al.
(Continued)

FOREIGN PATENT DOCUMENTS

AU  WO 97/24980  *  7/1997  ............... A61B 5/02
DE  42 34 533 C2  1/1995
(Continued)

OTHER PUBLICATIONS

Arnold Henry Kadish, M.D., "Biocybernetics of Bodily Fuels—Monitoring of Blood Glucose and the Establishment of On-Line Metabolic Homeostasis," Proceedings of the 3.sup.rd Hawaii International Conference on System Sciences Part 1, 1970, pp. 231-234.
(Continued)

*Primary Examiner* — Larry D Riggs, II
(74) *Attorney, Agent, or Firm* — Edward J. Baba; Brian E. Davy; Bozicevic, Field & Francis LLP

(57) ABSTRACT

A measurement module for glucose testing includes a glucose testing measurement module housing, a test strip receptacle formed in the housing, and a connector portion formed in the housing and shaped to permit mechanical removable attachment of the housing to a hand-held computer. Electronics determine the amount of glucose present in a sample of body fluid, when the test strip is positioned in the receptacle and the body fluid is placed on a test strip, and communicate the glucose amount to the hand-held computer via the connector portion.

12 Claims, 16 Drawing Sheets

(51) Int. Cl.

| | | |
|---|---|---|
| *G06G 7/48* | (2006.01) | |
| *G06G 7/58* | (2006.01) | |
| *G06F 19/00* | (2011.01) | |
| *A61B 5/00* | (2006.01) | |
| *G06Q 50/22* | (2012.01) | |
| *G06Q 50/24* | (2012.01) | |
| *G01N 33/487* | (2006.01) | |
| *A61B 5/145* | (2006.01) | |

(52) U.S. Cl.
CPC ..... *G01N33/48792* (2013.01); *G06F 19/3406* (2013.01); *G06Q 50/22* (2013.01); *G06Q 50/24* (2013.01); *A61B 5/14532* (2013.01); *A61B 2562/0295* (2013.01); *Y10S 435/97* (2013.01)

(56) References Cited

U.S. PATENT DOCUMENTS

| | | |
|---|---|---|
| 3,219,533 A | 11/1965 | Mullins |
| 3,260,656 A | 7/1966 | Ross, Jr. |
| 3,282,875 A | 11/1966 | Connolly et al. |
| 3,304,413 A | 2/1967 | Lehmann et al. |
| 3,310,606 A | 3/1967 | Fritz |
| 3,397,191 A | 8/1968 | Beckerbauer |
| 3,635,926 A | 1/1972 | Gresham et al. |
| 3,651,318 A | 3/1972 | Czekajewski |
| 3,653,841 A | 4/1972 | Klein |
| 3,698,386 A | 10/1972 | Fried |
| 3,719,564 A | 3/1973 | Lilly, Jr. et al. |
| 3,768,014 A | 10/1973 | Smith et al. |
| 3,775,182 A | 11/1973 | Patton et al. |
| 3,776,832 A | 12/1973 | Oswin et al. |
| 3,785,939 A | 1/1974 | Hsu |
| 3,837,339 A | 9/1974 | Aisenberg et al. |
| 3,851,018 A | 11/1974 | Kelly |
| 3,910,257 A * | 10/1975 | Fletcher et al. .............. 600/483 |
| 3,919,051 A | 11/1975 | Koch et al. |
| 3,926,760 A | 12/1975 | Allen et al. |
| 3,929,971 A | 12/1975 | Roy |
| 3,930,889 A | 1/1976 | Ruggiero et al. |
| 3,933,593 A | 1/1976 | Sternberg |
| 3,964,974 A | 6/1976 | Banauch et al. |
| 3,966,580 A | 6/1976 | Janata et al. |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,024,312 A | 5/1977 | Korpman |
| 4,032,729 A | 6/1977 | Koistinen |
| 4,036,749 A | 7/1977 | Anderson |
| 4,040,908 A | 8/1977 | Clark, Jr. |
| 4,055,175 A | 10/1977 | Clemens et al. |
| 4,059,406 A | 11/1977 | Fleet |
| 4,059,708 A | 11/1977 | Heiss, Jr. et al. |
| 4,073,713 A | 2/1978 | Newman |
| 4,076,596 A | 2/1978 | Connery et al. |
| 4,076,656 A | 2/1978 | White et al. |
| 4,098,574 A | 7/1978 | Dappen |
| 4,100,048 A | 7/1978 | Pompei et al. |
| 4,129,128 A | 12/1978 | McFarlane |
| 4,151,845 A | 5/1979 | Clemens |
| 4,154,231 A | 5/1979 | Russell |
| 4,168,205 A | 9/1979 | Danninger et al. |
| 4,172,770 A | 10/1979 | Semersky et al. |
| 4,178,916 A | 12/1979 | McNamara |
| 4,193,982 A | 3/1980 | Avrameas et al. |
| 4,197,840 A | 4/1980 | Beck et al. |
| 4,206,755 A | 6/1980 | Klein |
| 4,215,703 A | 8/1980 | Wilson |
| 4,224,125 A | 9/1980 | Nakamura et al. |
| 4,240,438 A | 12/1980 | Updike et al. |
| 4,240,889 A | 12/1980 | Yoda et al. |
| 4,241,438 A | 12/1980 | Kern |
| 4,245,634 A | 1/1981 | Albisser et al. |
| 4,247,297 A | 1/1981 | Berti et al. |
| 4,255,500 A | 3/1981 | Hooke |
| 4,259,540 A | 3/1981 | Sabia |
| 4,271,449 A | 6/1981 | Grogan |
| 4,275,225 A | 6/1981 | Krespan |
| 4,318,784 A | 3/1982 | Higgins et al. |
| 4,324,257 A | 4/1982 | Albarda et al. |
| 4,327,725 A | 5/1982 | Cortese et al. |
| 4,331,869 A | 5/1982 | Rollo |
| 4,335,255 A | 6/1982 | Krespan |
| 4,340,458 A | 7/1982 | Lerner et al. |
| 4,344,438 A | 8/1982 | Schultz |
| 4,352,960 A | 10/1982 | Dormer et al. |
| 4,353,888 A | 10/1982 | Sefton |
| 4,356,074 A | 10/1982 | Johnson |
| 4,357,282 A | 11/1982 | Anderson et al. |
| 4,365,637 A | 12/1982 | Johnson |
| 4,366,033 A | 12/1982 | Richter et al. |
| 4,374,013 A | 2/1983 | Enfors |
| 4,375,399 A | 3/1983 | Havas et al. |
| 4,384,586 A | 5/1983 | Christiansen |
| 4,388,166 A | 6/1983 | Suzuki et al. |
| 4,390,621 A | 6/1983 | Bauer |
| 4,392,933 A | 7/1983 | Nakamura et al. |
| 4,401,122 A | 8/1983 | Clark, Jr. |
| 4,404,066 A | 9/1983 | Johnson |
| 4,407,288 A | 10/1983 | Langer et al. |
| 4,407,959 A | 10/1983 | Tsuji et al. |
| 4,415,666 A | 11/1983 | D'Orazio et al. |
| 4,417,588 A | 11/1983 | Houghton et al. |
| 4,418,148 A | 11/1983 | Oberhardt |
| 4,420,564 A | 12/1983 | Tsuji et al. |
| 4,425,920 A | 1/1984 | Bourland et al. |
| 4,427,004 A | 1/1984 | Miller |
| 4,427,770 A | 1/1984 | Chen et al. |
| 4,431,004 A | 2/1984 | Bessman et al. |
| 4,431,507 A | 2/1984 | Nankai et al. |
| 4,436,094 A | 3/1984 | Cerami |
| 4,440,175 A | 4/1984 | Wilkins |
| 4,443,218 A | 4/1984 | DeCant, Jr. et al. |
| 4,444,892 A | 4/1984 | Malmros |
| 4,450,842 A | 5/1984 | Zick et al. |
| 4,458,686 A | 7/1984 | Clark, Jr. |
| 4,461,691 A | 7/1984 | Frank |
| 4,467,811 A | 8/1984 | Clark, Jr. |
| 4,469,110 A | 9/1984 | Slama |
| 4,476,003 A | 10/1984 | Frank et al. |
| 4,477,314 A | 10/1984 | Richter et al. |
| 4,478,976 A | 10/1984 | Goertz et al. |
| 4,483,924 A | 11/1984 | Tsuji et al. |
| 4,484,987 A | 11/1984 | Gough |
| 4,494,950 A | 1/1985 | Fischell |
| 4,499,249 A | 2/1985 | Nakagawa et al. |
| 4,506,680 A | 3/1985 | Stokes |
| 4,512,348 A | 4/1985 | Uchigaki et al. |
| 4,522,690 A | 6/1985 | Venkatsetty |
| 4,524,114 A | 6/1985 | Samuels et al. |
| 4,526,661 A | 7/1985 | Steckhan et al. |
| 4,526,948 A | 7/1985 | Resnick |
| 4,527,240 A | 7/1985 | Kvitash |
| 4,530,696 A | 7/1985 | Bisera et al. |
| 4,534,356 A | 8/1985 | Papadakis |
| 4,538,616 A | 9/1985 | Rogoff |
| 4,543,955 A | 10/1985 | Schroeppel |
| 4,544,869 A | 10/1985 | Pittaway |
| 4,545,382 A | 10/1985 | Higgins et al. |
| 4,552,840 A | 11/1985 | Riffer |
| 4,560,534 A | 12/1985 | Kung et al. |
| 4,561,443 A | 12/1985 | Hogrefe et al. |
| 4,569,589 A | 2/1986 | Neufeld |
| 4,571,292 A | 2/1986 | Liu et al. |
| 4,573,994 A | 3/1986 | Fischell et al. |
| 4,577,642 A | 3/1986 | Stokes |
| 4,581,336 A | 4/1986 | Malloy et al. |
| 4,595,011 A | 6/1986 | Phillips |
| 4,595,479 A | 6/1986 | Kimura et al. |
| 4,614,760 A | 9/1986 | Homan et al. |
| 4,619,754 A | 10/1986 | Niki et al. |
| 4,619,793 A | 10/1986 | Lee |

(56) References Cited

U.S. PATENT DOCUMENTS

| | | |
|---|---|---|
| 4,627,445 A | 12/1986 | Garcia et al. |
| 4,627,908 A | 12/1986 | Miller |
| 4,633,878 A | 1/1987 | Bombardien |
| 4,633,881 A | 1/1987 | Moore et al. |
| 4,637,403 A | 1/1987 | Garcia et al. |
| RE32,361 E | 2/1987 | Duggan |
| 4,648,408 A | 3/1987 | Hutcheson et al. |
| 4,650,547 A | 3/1987 | Gough |
| 4,653,513 A | 3/1987 | Dombrowski |
| 4,654,197 A | 3/1987 | Lilja et al. |
| 4,655,880 A | 4/1987 | Liu |
| 4,655,885 A | 4/1987 | Hill et al. |
| 4,658,463 A | 4/1987 | Sugita et al. |
| 4,663,824 A | 5/1987 | Kenmochi |
| 4,671,288 A | 6/1987 | Gough |
| 4,674,652 A | 6/1987 | Aten et al. |
| 4,679,562 A | 7/1987 | Luksha |
| 4,680,268 A | 7/1987 | Clark, Jr. |
| 4,681,111 A | 7/1987 | Silvian |
| 4,682,602 A | 7/1987 | Prohaska |
| 4,684,537 A | 8/1987 | Graetzel et al. |
| 4,685,463 A | 8/1987 | Williams |
| 4,686,624 A | 8/1987 | Blum et al. |
| 4,698,582 A | 10/1987 | Braun et al. |
| 4,703,756 A | 11/1987 | Gough et al. |
| 4,711,245 A | 12/1987 | Higgins et al. |
| 4,711,251 A | 12/1987 | Stokes |
| 4,714,462 A | 12/1987 | DiDomenico |
| 4,717,673 A | 1/1988 | Wrighton et al. |
| 4,718,893 A | 1/1988 | Dorman |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,731,051 A | 3/1988 | Fischell |
| 4,731,726 A | 3/1988 | Allen, III |
| 4,747,828 A | 5/1988 | Tseo |
| 4,749,985 A | 6/1988 | Corsberg |
| 4,750,496 A | 6/1988 | Reinhardt |
| 4,753,652 A | 6/1988 | Langer et al. |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,798 A | 11/1988 | Gough |
| 4,784,736 A | 11/1988 | Lonsdale et al. |
| 4,787,398 A | 11/1988 | Garcia et al. |
| 4,795,707 A | 1/1989 | Niiyama et al. |
| 4,796,634 A | 1/1989 | Huntsman et al. |
| 4,803,243 A | 2/1989 | Fujimoto et al. |
| 4,803,625 A | 2/1989 | Fu et al. |
| 4,803,726 A | 2/1989 | Levine et al. |
| 4,805,624 A | 2/1989 | Yao et al. |
| 4,810,470 A | 3/1989 | Burkhardt et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| 4,835,372 A | 5/1989 | Gombrich et al. |
| RE32,947 E | 6/1989 | Dormer et al. |
| 4,837,049 A | 6/1989 | Byers et al. |
| 4,838,887 A | 6/1989 | Idriss |
| 4,840,893 A | 6/1989 | Hill et al. |
| RE32,974 E | 7/1989 | Porat et al. |
| 4,844,076 A | 7/1989 | Lesho et al. |
| 4,845,035 A | 7/1989 | Fanta et al. |
| 4,848,351 A | 7/1989 | Finch |
| 4,849,458 A | 7/1989 | Reed et al. |
| 4,854,322 A | 8/1989 | Ash et al. |
| 4,856,340 A | 8/1989 | Garrison |
| 4,857,713 A | 8/1989 | Brown |
| 4,858,617 A | 8/1989 | Sanders |
| 4,870,561 A | 9/1989 | Love et al. |
| 4,871,351 A | 10/1989 | Feingold |
| 4,871,440 A | 10/1989 | Nagata et al. |
| 4,874,499 A | 10/1989 | Smith et al. |
| 4,874,500 A | 10/1989 | Madou et al. |
| 4,889,744 A | 12/1989 | Quaid |
| 4,890,620 A | 1/1990 | Gough |
| 4,890,621 A | 1/1990 | Hakky |
| 4,894,137 A | 1/1990 | Takizawa et al. |
| 4,896,142 A | 1/1990 | Aycox et al. |
| 4,897,162 A | 1/1990 | Lewandowski et al. |
| 4,897,173 A | 1/1990 | Nankai et al. |
| 4,897,457 A | 1/1990 | Nakamura et al. |
| 4,899,839 A | 2/1990 | Dessertine et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,920,969 A | 5/1990 | Suzuki |
| 4,920,977 A | 5/1990 | Haynes |
| 4,923,586 A | 5/1990 | Katayama et al. |
| 4,925,268 A | 5/1990 | Iyer et al. |
| 4,927,407 A | 5/1990 | Dorman |
| 4,927,516 A | 5/1990 | Yamaguchi et al. |
| 4,931,795 A | 6/1990 | Gord |
| 4,934,369 A | 6/1990 | Maxwell |
| 4,935,105 A | 6/1990 | Churchouse |
| 4,935,345 A | 6/1990 | Guilbeau et al. |
| 4,936,956 A | 6/1990 | Wrighton |
| 4,938,860 A | 7/1990 | Wogoman |
| 4,942,127 A | 7/1990 | Wada et al. |
| 4,944,299 A | 7/1990 | Silvian |
| 4,945,045 A | 7/1990 | Forrest et al. |
| 4,950,378 A | 8/1990 | Nagara |
| 4,953,552 A | 9/1990 | DeMarzo |
| 4,954,129 A | 9/1990 | Giuliani et al. |
| 4,955,861 A | 9/1990 | Enegren et al. |
| 4,957,115 A | 9/1990 | Selker |
| 4,958,632 A | 9/1990 | Duggan |
| 4,963,595 A | 10/1990 | Ward et al. |
| 4,968,400 A | 11/1990 | Shimomura et al. |
| 4,969,468 A | 11/1990 | Byers et al. |
| 4,970,145 A | 11/1990 | Bennetto et al. |
| 4,974,929 A | 12/1990 | Curry |
| 4,979,509 A | 12/1990 | Hakky |
| 4,984,929 A | 1/1991 | Rock et al. |
| 4,986,271 A | 1/1991 | Wilkins |
| 4,986,671 A | 1/1991 | Sun et al. |
| 4,990,845 A | 2/1991 | Gord |
| 4,991,582 A | 2/1991 | Byers et al. |
| 4,994,068 A | 2/1991 | Hufnagie |
| 4,994,167 A | 2/1991 | Shults et al. |
| 4,995,402 A | 2/1991 | Smith et al. |
| 5,001,054 A | 3/1991 | Wagner |
| 5,002,054 A | 3/1991 | Ash et al. |
| 5,002,572 A | 3/1991 | Picha |
| 5,007,427 A | 4/1991 | Suzuki et al. |
| 5,007,929 A | 4/1991 | Quaid |
| 5,016,172 A | 5/1991 | Dessertine |
| 5,016,201 A | 5/1991 | Bryan et al. |
| 5,016,631 A | 5/1991 | Hogrefe et al. |
| 5,019,974 A | 5/1991 | Beckers |
| 5,030,333 A | 7/1991 | Clark, Jr. |
| 5,034,112 A | 7/1991 | Murase et al. |
| 5,034,192 A | 7/1991 | Wrighton et al. |
| 5,035,860 A | 7/1991 | Kleingeld et al. |
| 5,036,860 A | 8/1991 | Leigh et al. |
| 5,036,861 A | 8/1991 | Sembrowich et al. |
| 5,037,527 A | 8/1991 | Hayashi et al. |
| 5,049,487 A | 9/1991 | Phillips et al. |
| 5,050,612 A | 9/1991 | Matsumura |
| 5,055,171 A | 10/1991 | Peck |
| 5,058,592 A | 10/1991 | Whisler |
| 5,059,654 A | 10/1991 | Hou et al. |
| 5,063,081 A | 11/1991 | Cozzette et al. |

(56) References Cited

U.S. PATENT DOCUMENTS

| | | |
|---|---|---|
| 5,067,491 A | 11/1991 | Taylor et al. |
| 5,068,536 A | 11/1991 | Rosenthal |
| 5,070,535 A | 12/1991 | Hochmair et al. |
| 5,073,500 A | 12/1991 | Saito et al. |
| 5,074,977 A | 12/1991 | Cheung et al. |
| 5,077,476 A | 12/1991 | Rosenthal |
| 5,078,854 A | 1/1992 | Burgess et al. |
| 5,082,550 A | 1/1992 | Rishpon et al. |
| 5,082,786 A | 1/1992 | Nakamoto |
| 5,084,828 A | 1/1992 | Kaufman et al. |
| 5,088,981 A | 2/1992 | Howson et al. |
| 5,089,112 A | 2/1992 | Skotheim et al. |
| 5,094,951 A | 3/1992 | Rosenberg |
| 5,095,904 A | 3/1992 | Seligman et al. |
| 5,096,560 A | 3/1992 | Takai et al. |
| 5,096,836 A | 3/1992 | Macho et al. |
| 5,097,834 A | 3/1992 | Skrabal |
| 5,101,814 A | 4/1992 | Palti |
| 5,106,365 A | 4/1992 | Hernandez |
| 5,108,564 A | 4/1992 | Szuminsky et al. |
| 5,109,850 A | 5/1992 | Blanco et al. |
| 5,111,539 A | 5/1992 | Hiruta et al. |
| 5,111,818 A | 5/1992 | Suzuji et al. |
| 5,114,678 A | 5/1992 | Crawford et al. |
| 5,120,420 A | 6/1992 | Nankai et al. |
| 5,120,421 A | 6/1992 | Glass et al. |
| 5,126,034 A | 6/1992 | Carter et al. |
| 5,126,247 A | 6/1992 | Palmer et al. |
| 5,130,009 A | 7/1992 | Marsoner et al. |
| 5,131,441 A | 7/1992 | Simpson et al. |
| 5,133,856 A | 7/1992 | Yamaguchi et al. |
| 5,134,391 A | 7/1992 | Okada |
| 5,135,003 A | 8/1992 | Souma |
| 5,139,023 A | 8/1992 | Stanley et al. |
| 5,140,393 A | 8/1992 | Hijikihigawa et al. |
| 5,140,985 A | 8/1992 | Schroeder et al. |
| 5,141,868 A | 8/1992 | Shanks et al. |
| 5,147,725 A | 9/1992 | Pinchuk |
| 5,153,827 A | 10/1992 | Coutre et al. |
| 5,161,532 A | 11/1992 | Joseph |
| 5,165,407 A | 11/1992 | Wilson et al. |
| 5,168,046 A | 12/1992 | Hamamoto et al. |
| 5,171,689 A | 12/1992 | Kawaguri et al. |
| 5,174,291 A | 12/1992 | Schoonen et al. |
| 5,176,644 A | 1/1993 | Srisathapat et al. |
| 5,176,662 A | 1/1993 | Bartholomew et al. |
| 5,182,707 A | 1/1993 | Cooper et al. |
| 5,184,359 A | 2/1993 | Tsukamura et al. |
| 5,185,256 A | 2/1993 | Nankai et al. |
| 5,190,041 A | 3/1993 | Palti |
| 5,192,415 A | 3/1993 | Yoshioka et al. |
| 5,192,416 A | 3/1993 | Wang et al. |
| 5,193,539 A | 3/1993 | Schulman et al. |
| 5,193,540 A | 3/1993 | Schulman et al. |
| 5,197,322 A | 3/1993 | Indravudh |
| 5,198,367 A | 3/1993 | Aizawa et al. |
| 5,198,771 A | 3/1993 | Fidler et al. |
| 5,200,051 A | 4/1993 | Cozzette et al. |
| 5,202,261 A | 4/1993 | Musho et al. |
| 5,205,920 A | 4/1993 | Oyama et al. |
| 5,206,145 A | 4/1993 | Cattell |
| 5,208,154 A | 5/1993 | Weaver et al. |
| 5,209,229 A | 5/1993 | Gilli |
| 5,215,887 A | 6/1993 | Saito |
| 5,216,597 A | 6/1993 | Beckers |
| 5,217,442 A | 6/1993 | Davis |
| 5,217,595 A | 6/1993 | Smith et al. |
| 5,227,042 A | 7/1993 | Zawodzinski et al. |
| 5,229,282 A | 7/1993 | Yoshioka et al. |
| 5,232,668 A | 8/1993 | Grant et al. |
| 5,235,003 A | 8/1993 | Ward et al. |
| 5,243,983 A | 9/1993 | Tarr et al. |
| 5,246,867 A | 9/1993 | Lakowicz et al. |
| 5,249,576 A | 10/1993 | Goldberger et al. |
| 5,250,439 A | 10/1993 | Musho et al. |
| 5,251,126 A | 10/1993 | Kahn et al. |
| 5,257,971 A | 11/1993 | Lord et al. |
| 5,257,980 A | 11/1993 | Van Antwerp et al. |
| 5,259,769 A | 11/1993 | Cruise et al. |
| 5,261,401 A | 11/1993 | Baker et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,106 A | 11/1993 | McAleer et al. |
| 5,265,888 A | 11/1993 | Yamamoto et al. |
| 5,266,179 A | 11/1993 | Nankai et al. |
| 5,269,212 A | 12/1993 | Peters et al. |
| 5,271,736 A | 12/1993 | Picha |
| 5,271,815 A | 12/1993 | Wong |
| 5,272,060 A | 12/1993 | Hamamoto et al. |
| 5,275,159 A | 1/1994 | Griebel |
| 5,276,610 A | 1/1994 | Maeda et al. |
| 5,278,079 A | 1/1994 | Gubinski et al. |
| 5,279,294 A | 1/1994 | Anderson |
| 5,282,848 A | 2/1994 | Schmitt |
| 5,282,950 A | 2/1994 | Dietze et al. |
| 5,284,156 A | 2/1994 | Schramm et al. |
| 5,284,570 A | 2/1994 | Savage et al. |
| 5,284,748 A | 2/1994 | Mroczkawski et al. |
| 5,285,513 A | 2/1994 | Kaufman et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,291,887 A | 3/1994 | Stanley et al. |
| 5,293,546 A | 3/1994 | Tadros et al. |
| 5,299,571 A | 4/1994 | Mastrototaro |
| 5,304,127 A | 4/1994 | Kawahara et al. |
| 5,304,468 A | 4/1994 | Phillips et al. |
| 5,307,263 A | 4/1994 | Brown |
| 5,309,919 A | 5/1994 | Snell et al. |
| 5,310,469 A | 5/1994 | Cunningham et al. |
| 5,310,885 A | 5/1994 | Maier et al. |
| 5,312,361 A | 5/1994 | Zadini et al. |
| 5,314,450 A | 5/1994 | Thompson |
| 5,314,471 A | 5/1994 | Brauker et al. |
| 5,318,521 A | 6/1994 | Slettenmark |
| 5,320,098 A | 6/1994 | Davidson |
| 5,320,725 A | 6/1994 | Gregg et al. |
| 5,322,063 A | 6/1994 | Allen et al. |
| 5,324,303 A | 6/1994 | Strong et al. |
| 5,324,316 A | 6/1994 | Schulman et al. |
| 5,326,356 A | 7/1994 | Della Valle et al. |
| 5,326,449 A | 7/1994 | Cunningham |
| 5,328,460 A | 7/1994 | Lord et al. |
| 5,330,521 A | 7/1994 | Cohen |
| 5,330,634 A | 7/1994 | Wong et al. |
| 5,331,966 A | 7/1994 | Bennett et al. |
| 5,337,258 A | 8/1994 | Dennis |
| 5,337,747 A | 8/1994 | Neftei |
| 5,340,722 A | 8/1994 | Wolfbeis et al. |
| 5,342,409 A | 8/1994 | Mullett |
| 5,342,789 A | 8/1994 | Chick et al. |
| 5,343,869 A | 9/1994 | Pross et al. |
| 5,344,454 A | 9/1994 | Clarke et al. |
| 5,348,788 A | 9/1994 | White |
| 5,350,407 A | 9/1994 | McClure et al. |
| 5,352,348 A | 10/1994 | Young et al. |
| 5,352,351 A | 10/1994 | White |
| 5,354,319 A | 10/1994 | Wyborny et al. |
| 5,356,348 A | 10/1994 | Bellio et al. |
| 5,356,786 A | 10/1994 | Heller et al. |
| 5,358,514 A | 10/1994 | Schulman et al. |
| 5,364,797 A | 11/1994 | Olson et al. |
| 5,366,609 A | 11/1994 | White et al. |
| 5,368,028 A | 11/1994 | Palti |
| 5,368,562 A | 11/1994 | Blomquist et al. |
| 5,370,622 A | 12/1994 | Livingston et al. |
| 5,371,687 A | 12/1994 | Holmes, II et al. |
| 5,372,133 A | 12/1994 | Hogen Esch |
| 5,372,719 A | 12/1994 | Afejan et al. |
| 5,376,070 A | 12/1994 | Purvis et al. |
| 5,376,251 A | 12/1994 | Kaneko et al. |

(56) References Cited

U.S. PATENT DOCUMENTS

| | | |
|---|---|---|
| 5,377,258 A | 12/1994 | Bro |
| 5,378,628 A | 1/1995 | Gratzel et al. |
| 5,379,238 A | 1/1995 | Stark |
| 5,380,422 A | 1/1995 | Negishis et al. |
| 5,380,536 A | 1/1995 | Hubbell et al. |
| 5,382,346 A | 1/1995 | Uenoyama et al. |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney, II et al. |
| 5,393,903 A | 2/1995 | Gratzel et al. |
| 5,395,504 A | 3/1995 | Saurer et al. |
| 5,397,848 A | 3/1995 | Yang et al. |
| 5,399,823 A | 3/1995 | McCusker |
| 5,400,782 A | 3/1995 | Beaubiah |
| 5,408,999 A | 4/1995 | Singh et al. |
| 5,410,471 A | 4/1995 | Alyfuku et al. |
| 5,410,474 A | 4/1995 | Fox |
| 5,411,536 A | 5/1995 | Armstrong |
| 5,411,647 A | 5/1995 | Johnson et al. |
| 5,413,690 A | 5/1995 | Kost et al. |
| 5,422,246 A | 6/1995 | Koopal et al. |
| 5,426,032 A | 6/1995 | Phillips |
| 5,429,129 A | 7/1995 | Lovejoy et al. |
| 5,431,160 A | 7/1995 | Wilkins |
| 5,431,691 A | 7/1995 | Snell et al. |
| 5,431,921 A | 7/1995 | Thombre |
| 5,433,710 A | 7/1995 | Van Antwerp et al. |
| 5,437,973 A | 8/1995 | Vadgama et al. |
| 5,437,999 A | 8/1995 | Dieboid et al. |
| 5,438,984 A | 8/1995 | Schoendorfer |
| 5,445,611 A | 8/1995 | Eppstein et al. |
| 5,445,920 A | 8/1995 | Saito |
| 5,451,260 A | 9/1995 | Versteeg et al. |
| 5,452,173 A | 9/1995 | Brannon et al. |
| 5,453,199 A | 9/1995 | Afejan et al. |
| 5,453,278 A | 9/1995 | Chan et al. |
| 5,456,692 A | 10/1995 | Smith, Jr. et al. |
| 5,456,940 A | 10/1995 | Funderburk |
| 5,458,140 A | 10/1995 | Eppstein et al. |
| 5,460,618 A | 10/1995 | Harreld |
| 5,462,064 A | 10/1995 | D'Angelo et al. |
| 5,462,525 A | 10/1995 | Srisathapat et al. |
| 5,462,645 A | 10/1995 | Albery et al. |
| 5,466,218 A | 11/1995 | Srisathapat et al. |
| 5,469,846 A | 11/1995 | Khan |
| 5,472,317 A | 12/1995 | Field et al. |
| 5,476,460 A | 12/1995 | Montalvo |
| 5,477,855 A | 12/1995 | Schindler et al. |
| 5,482,473 A | 1/1996 | Lord et al. |
| 5,484,404 A | 1/1996 | Schulman et al. |
| 5,487,751 A | 1/1996 | Radons et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,501,665 A | 3/1996 | Jhuboo et al. |
| 5,501,956 A | 3/1996 | Wada et al. |
| 5,505,709 A | 4/1996 | Funderburk |
| 5,505,713 A | 4/1996 | Van Antwerp et al. |
| 5,507,288 A | 4/1996 | Bocker et al. |
| 5,508,171 A | 4/1996 | Walling et al. |
| 5,509,410 A | 4/1996 | Hill et al. |
| 5,514,103 A | 5/1996 | Srisathapat et al. |
| 5,514,253 A | 5/1996 | Davis et al. |
| 5,518,006 A | 5/1996 | Mawhirt et al. |
| 5,520,787 A | 5/1996 | Hanagan et al. |
| 5,522,865 A | 6/1996 | Schulman et al. |
| 5,525,511 A | 6/1996 | D'Costa |
| 5,526,120 A | 6/1996 | Jina et al. |
| 5,527,307 A | 6/1996 | Srisathapat et al. |
| 5,529,676 A | 6/1996 | Maley et al. |
| 5,531,878 A | 7/1996 | Vadgama et al. |
| 5,538,007 A | 7/1996 | Gorman |
| 5,538,511 A | 7/1996 | Van Antwerp et al. |
| 5,540,828 A | 7/1996 | Yacynych |
| 5,545,152 A | 8/1996 | Funderburk et al. |
| 5,545,191 A | 8/1996 | Mann et al. |
| 5,545,220 A | 8/1996 | Andrews et al. |
| 5,545,223 A | 8/1996 | Neuenfeldt et al. |
| 5,549,113 A | 8/1996 | Halleck et al. |
| 5,549,115 A | 8/1996 | Morgan et al. |
| 5,549,675 A | 8/1996 | Neuenfeldt et al. |
| 5,552,027 A | 9/1996 | Birkle et al. |
| 5,554,166 A | 9/1996 | Lange et al. |
| 5,556,524 A | 9/1996 | Albers |
| 5,558,638 A | 9/1996 | Evers et al. |
| 5,560,357 A | 10/1996 | Faupei et al. |
| 5,562,713 A | 10/1996 | Silvian |
| 5,564,439 A | 10/1996 | Picha |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,569,212 A | 10/1996 | Brown |
| 5,569,462 A | 10/1996 | Martinson et al. |
| 5,571,395 A | 11/1996 | Park et al. |
| 5,573,506 A | 11/1996 | Vasko |
| 5,573,647 A | 11/1996 | Maley et al. |
| 5,575,895 A | 11/1996 | Ikeda et al. |
| 5,575,930 A | 11/1996 | Tietje-Girault et al. |
| 5,580,527 A | 12/1996 | Bell et al. |
| 5,580,794 A | 12/1996 | Allen |
| 5,582,184 A | 12/1996 | Erickson et al. |
| 5,582,593 A | 12/1996 | Hultman |
| 5,582,697 A | 12/1996 | Ikeda et al. |
| 5,582,698 A | 12/1996 | Flaherty et al. |
| 5,584,813 A | 12/1996 | Livingston et al. |
| 5,584,876 A | 12/1996 | Bruchman et al. |
| 5,586,553 A | 12/1996 | Halli et al. |
| 5,587,273 A | 12/1996 | Yan et al. |
| 5,589,326 A | 12/1996 | Deng et al. |
| 5,589,563 A | 12/1996 | Ward et al. |
| 5,590,651 A | 1/1997 | Shaffer et al. |
| 5,593,440 A | 1/1997 | Brauker et al. |
| 5,593,852 A | 1/1997 | Heller et al. |
| 5,594,906 A | 1/1997 | Holmes, II et al. |
| 5,596,150 A | 1/1997 | Arndy et al. |
| 5,596,994 A | 1/1997 | Bro |
| 5,601,435 A | 2/1997 | Quy |
| 5,601,694 A | 2/1997 | Maley et al. |
| 5,605,152 A | 2/1997 | Slate et al. |
| 5,607,565 A | 3/1997 | Azarnia et al. |
| 5,611,900 A | 3/1997 | Worden et al. |
| 5,615,091 A * | 3/1997 | Palatnik .................. 363/17 |
| 5,615,671 A | 4/1997 | Schoonen et al. |
| 5,616,222 A | 4/1997 | Maley et al. |
| 5,617,851 A | 4/1997 | Lipkovker |
| 5,623,925 A | 4/1997 | Swenson et al. |
| 5,624,537 A | 4/1997 | Turner et al. |
| 5,628,309 A | 5/1997 | Brown |
| 5,628,310 A | 5/1997 | Rao et al. |
| 5,628,890 A | 5/1997 | Carter et al. |
| 5,629,981 A | 5/1997 | Nerlikar |
| 5,637,095 A | 6/1997 | Nason et al. |
| 5,640,764 A | 6/1997 | Strojnik |
| 5,640,954 A | 6/1997 | Pfeiffer et al. |
| 5,643,212 A | 7/1997 | Coutre et al. |
| 5,647,853 A | 7/1997 | Feldmann et al. |
| 5,650,062 A | 7/1997 | Ikeda et al. |
| 5,651,767 A | 7/1997 | Schulman et al. |
| 5,651,869 A | 7/1997 | Yoshioka et al. |
| 5,653,735 A | 8/1997 | Chen et al. |
| 5,653,756 A | 8/1997 | Clarke et al. |
| 5,653,863 A | 8/1997 | Glenshaw et al. |
| 5,658,250 A | 8/1997 | Blomquist et al. |
| 5,658,330 A | 8/1997 | Carlisle et al. |
| 5,660,163 A | 8/1997 | Schulman et al. |
| 5,662,694 A | 9/1997 | Lidman et al. |
| 5,665,065 A | 9/1997 | Colman et al. |
| 5,667,983 A | 9/1997 | Abel et al. |
| 5,670,031 A | 9/1997 | Hintsche et al. |
| 5,673,691 A | 10/1997 | Abrams et al. |
| 5,678,571 A | 10/1997 | Brown |

(56) References Cited

U.S. PATENT DOCUMENTS

| | | |
|---|---|---|
| 5,679,690 A | 10/1997 | Andre et al. |
| 5,680,858 A | 10/1997 | Hansen et al. |
| 5,682,233 A | 10/1997 | Brinda |
| 5,686,717 A | 11/1997 | Knowles et al. |
| 5,686,829 A | 11/1997 | Girault |
| 5,695,473 A | 12/1997 | Olsen |
| 5,695,623 A | 12/1997 | Michel et al. |
| 5,695,949 A | 12/1997 | Galen et al. |
| 5,701,894 A | 12/1997 | Cherry et al. |
| 5,704,354 A | 1/1998 | Priedel et al. |
| 5,704,366 A | 1/1998 | Tacklind et al. |
| 5,704,922 A | 1/1998 | Brown |
| 5,706,807 A | 1/1998 | Picha |
| 5,707,502 A | 1/1998 | McCaffrey et al. |
| 5,708,247 A | 1/1998 | McAleer et al. |
| 5,710,630 A | 1/1998 | Essenpreis et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,711,868 A | 1/1998 | Maley et al. |
| 5,713,888 A | 2/1998 | Neuenfeldt et al. |
| 5,714,123 A | 2/1998 | Sohrab |
| 5,718,234 A | 2/1998 | Warden et al. |
| 5,720,733 A | 2/1998 | Brown |
| 5,720,862 A | 2/1998 | Hamamoto et al. |
| 5,721,783 A | 2/1998 | Anderson |
| 5,722,397 A | 3/1998 | Eppstein |
| 5,727,548 A | 3/1998 | Hill et al. |
| 5,730,124 A | 3/1998 | Yamauchi |
| 5,730,654 A | 3/1998 | Brown |
| 5,733,336 A | 3/1998 | Neuenfeldt et al. |
| 5,735,273 A | 4/1998 | Kurnik et al. |
| 5,735,285 A | 4/1998 | Albert et al. |
| 5,741,211 A | 4/1998 | Renirie et al. |
| 5,741,330 A | 4/1998 | Brauker et al. |
| 5,741,688 A | 4/1998 | Oxenboll et al. |
| 5,746,217 A | 5/1998 | Erickson et al. |
| 5,748,103 A | 5/1998 | Flach et al. |
| 5,749,907 A | 5/1998 | Mann |
| 5,750,926 A | 5/1998 | Schulman et al. |
| 5,756,632 A | 5/1998 | Ward et al. |
| 5,770,028 A | 6/1998 | Maley et al. |
| 5,771,001 A | 6/1998 | Cobb |
| 5,771,890 A | 6/1998 | Tamada |
| 5,772,586 A | 6/1998 | Heinonen et al. |
| 5,777,060 A | 7/1998 | Van Antwerp |
| 5,778,882 A | 7/1998 | Raymond et al. |
| 5,779,665 A | 7/1998 | Mastrototaro et al. |
| 5,782,814 A | 7/1998 | Brown et al. |
| 5,782,912 A | 7/1998 | Brauker et al. |
| 5,785,681 A | 7/1998 | Indravudh |
| 5,786,439 A | 7/1998 | Van Antwerp et al. |
| 5,786,584 A | 7/1998 | Button et al. |
| 5,787,900 A | 8/1998 | Butler et al. |
| 5,788,678 A | 8/1998 | Van Antwerp |
| 5,791,344 A | 8/1998 | Schulman et al. |
| 5,792,117 A | 8/1998 | Brown |
| 5,795,774 A | 8/1998 | Matsumoto et al. |
| 5,798,065 A | 8/1998 | Picha |
| 5,800,387 A | 9/1998 | Duffy et al. |
| 5,800,420 A | 9/1998 | Gross et al. |
| 5,800,529 A | 9/1998 | Brauker et al. |
| 5,804,048 A | 9/1998 | Wong et al. |
| 5,807,315 A | 9/1998 | Van Antwerp et al. |
| 5,807,375 A | 9/1998 | Gross et al. |
| 5,807,406 A | 9/1998 | Brauker et al. |
| 5,811,487 A | 9/1998 | Schulz, Jr. et al. |
| 5,814,599 A | 9/1998 | Mitragotri et al. |
| 5,820,551 A | 10/1998 | Hill et al. |
| 5,820,570 A | 10/1998 | Erickson et al. |
| 5,820,622 A | 10/1998 | Gross et al. |
| 5,822,715 A | 10/1998 | Worthington et al. |
| 5,825,488 A | 10/1998 | Kohl et al. |
| 5,827,179 A | 10/1998 | Lichter et al. |
| 5,827,180 A | 10/1998 | Goodman |
| 5,827,183 A | 10/1998 | Kurnik et al. |
| 5,827,184 A | 10/1998 | Netherly et al. |
| 5,828,943 A | 10/1998 | Brown |
| 5,830,341 A | 11/1998 | Gilmartin |
| 5,832,448 A | 11/1998 | Brown |
| 5,833,603 A | 11/1998 | Kovacs et al. |
| 5,834,224 A | 11/1998 | Ruger et al. |
| 5,836,887 A | 11/1998 | Oka et al. |
| 5,836,989 A | 11/1998 | Shelton |
| 5,837,454 A | 11/1998 | Cozzette et al. |
| 5,837,546 A | 11/1998 | Allen et al. |
| 5,837,728 A | 11/1998 | Purcell |
| 5,840,020 A | 11/1998 | Heinonen et al. |
| 5,840,240 A | 11/1998 | Stenoien et al. |
| 5,842,983 A | 12/1998 | Abel et al. |
| 5,843,140 A | 12/1998 | Strojnik |
| 5,846,702 A | 12/1998 | Deng et al. |
| 5,846,744 A | 12/1998 | Athey et al. |
| 5,851,197 A | 12/1998 | Marano et al. |
| 5,854,078 A | 12/1998 | Asher et al. |
| 5,854,189 A | 12/1998 | Kruse et al. |
| 5,857,967 A | 1/1999 | Frid et al. |
| 5,857,983 A | 1/1999 | Douglas et al. |
| 5,860,917 A | 1/1999 | Comanor et al. |
| 5,861,009 A | 1/1999 | Armstrong et al. |
| 5,861,019 A | 1/1999 | Sun et al. |
| 5,862,803 A | 1/1999 | Besson et al. |
| 5,871,465 A | 2/1999 | Vasko |
| 5,871,514 A | 2/1999 | Wiklund et al. |
| 5,872,713 A | 2/1999 | Douglas et al. |
| 5,872,820 A | 2/1999 | Upadrasta |
| 5,876,484 A | 3/1999 | Raskin et al. |
| 5,879,163 A | 3/1999 | Brown et al. |
| 5,879,311 A | 3/1999 | Duchon et al. |
| 5,879,373 A | 3/1999 | Roper et al. |
| 5,880,829 A | 3/1999 | Kauhaniemi et al. |
| 5,882,494 A | 3/1999 | Van Antwerp |
| 5,885,211 A | 3/1999 | Eppstein et al. |
| 5,885,245 A | 3/1999 | Lynch et al. |
| 5,887,133 A | 3/1999 | Brown et al. |
| 5,895,371 A | 4/1999 | Levitas et al. |
| 5,897,493 A | 4/1999 | Brown |
| 5,897,578 A | 4/1999 | Wiklund et al. |
| 5,898,025 A | 4/1999 | Burg et al. |
| 5,899,855 A | 5/1999 | Brown |
| 5,899,931 A | 5/1999 | Deschamp et al. |
| 5,902,234 A | 5/1999 | Webb |
| 5,904,708 A | 5/1999 | Goedeke |
| 5,913,310 A | 6/1999 | Brown |
| 5,913,827 A | 6/1999 | Gorman |
| 5,913,998 A | 6/1999 | Butler et al. |
| 5,914,026 A | 6/1999 | Blubaugh, Jr. et al. |
| 5,916,445 A | 6/1999 | Hjerten et al. |
| 5,917,346 A | 6/1999 | Gord |
| 5,918,603 A | 7/1999 | Brown |
| 5,919,215 A | 7/1999 | Wiklund et al. |
| 5,925,021 A | 7/1999 | Castellano et al. |
| 5,928,130 A | 7/1999 | Schmidt |
| 5,931,791 A | 8/1999 | Saltzstein et al. |
| 5,931,814 A | 8/1999 | Alex et al. |
| 5,933,136 A | 8/1999 | Brown |
| 5,935,099 A | 8/1999 | Peterson et al. |
| 5,935,785 A | 8/1999 | Reber et al. |
| 5,940,801 A | 8/1999 | Brown |
| 5,942,979 A | 8/1999 | Luppino |
| 5,945,345 A | 8/1999 | Blatt et al. |
| 5,947,749 A | 9/1999 | Rathburn |
| 5,947,921 A | 9/1999 | Johnson et al. |
| 5,948,512 A | 9/1999 | Kubota et al. |
| 5,950,632 A | 9/1999 | Reber et al. |
| 5,951,300 A | 9/1999 | Brown |
| 5,951,492 A | 9/1999 | Douglas et al. |
| 5,951,521 A | 9/1999 | Mastrototaro et al. |
| 5,951,836 A | 9/1999 | McAleer et al. |
| 5,954,641 A | 9/1999 | Kehr et al. |
| 5,954,643 A | 9/1999 | Van Antwerp |
| 5,954,685 A | 9/1999 | Tierney |
| 5,954,700 A | 9/1999 | Kovelman |

(56) References Cited

U.S. PATENT DOCUMENTS

| | | |
|---|---|---|
| 5,956,501 A | 9/1999 | Brown |
| 5,957,854 A | 9/1999 | Besson et al. |
| 5,957,890 A | 9/1999 | Mann et al. |
| 5,957,903 A | 9/1999 | Mirzaee et al. |
| 5,957,958 A | 9/1999 | Schulman et al. |
| 5,959,050 A | 9/1999 | Mosbach et al. |
| 5,960,403 A | 9/1999 | Brown |
| 5,961,451 A | 10/1999 | Reber et al. |
| 5,964,804 A | 10/1999 | Brauker et al. |
| 5,964,993 A | 10/1999 | Blubaugh, Jr. et al. |
| 5,965,380 A | 10/1999 | Heller et al. |
| 5,967,975 A | 10/1999 | Ridgeway |
| 5,968,839 A | 10/1999 | Blatt et al. |
| 5,971,922 A | 10/1999 | Arita et al. |
| 5,971,941 A | 10/1999 | Simons et al. |
| 5,974,124 A | 10/1999 | Schlueter, Jr. et al. |
| 5,976,085 A | 11/1999 | Kimball et al. |
| 5,977,476 A | 11/1999 | Guha et al. |
| 5,981,294 A | 11/1999 | Blatt et al. |
| 5,985,129 A | 11/1999 | Gough et al. |
| 5,987,352 A | 11/1999 | Klein et al. |
| 5,989,409 A | 11/1999 | Kurnik et al. |
| 5,991,729 A | 11/1999 | Barry et al. |
| 5,994,476 A | 11/1999 | Shin et al. |
| 5,995,860 A | 11/1999 | Sun et al. |
| 5,997,476 A | 12/1999 | Brown |
| 5,999,848 A | 12/1999 | Gord et al. |
| 5,999,849 A | 12/1999 | Gord et al. |
| 6,001,067 A | 12/1999 | Shults et al. |
| 6,001,471 A | 12/1999 | Bries et al. |
| 6,002,954 A | 12/1999 | Van Antwerp et al. |
| 6,002,961 A | 12/1999 | Mitragotri et al. |
| 6,004,441 A | 12/1999 | Fujiwara et al. |
| 6,007,845 A | 12/1999 | Domb |
| 6,011,984 A | 1/2000 | Van Antwerp et al. |
| 6,013,113 A | 1/2000 | Mika |
| 6,014,577 A | 1/2000 | Henning et al. |
| 6,016,448 A | 1/2000 | Busacker et al. |
| 6,017,435 A | 1/2000 | Hassard et al. |
| 6,018,678 A | 1/2000 | Mitragotri et al. |
| 6,023,629 A | 2/2000 | Tamada |
| 6,024,699 A | 2/2000 | Surwit et al. |
| 6,026,320 A | 2/2000 | Carlson et al. |
| 6,027,459 A | 2/2000 | Shain et al. |
| 6,027,692 A | 2/2000 | Galen et al. |
| 6,032,059 A | 2/2000 | Henning et al. |
| 6,032,119 A | 2/2000 | Brown et al. |
| 6,032,199 A | 2/2000 | Lim et al. |
| 6,033,866 A | 3/2000 | Guo et al. |
| 6,035,237 A | 3/2000 | Schulman et al. |
| 6,039,688 A | 3/2000 | Douglas et al. |
| 6,040,194 A | 3/2000 | Chick et al. |
| 6,041,253 A | 3/2000 | Kost et al. |
| 6,043,437 A | 3/2000 | Schulman et al. |
| 6,048,691 A | 4/2000 | Maracas |
| 6,049,727 A | 4/2000 | Crothall |
| 6,051,372 A | 4/2000 | Bayerl et al. |
| D424,696 S | 5/2000 | Ray et al. |
| 6,056,718 A | 5/2000 | Funderburk et al. |
| 6,057,377 A | 5/2000 | Sasaki et al. |
| 6,063,459 A | 5/2000 | Velte |
| 6,063,637 A | 5/2000 | Arnold et al. |
| 6,066,083 A | 5/2000 | Slater et al. |
| 6,066,243 A | 5/2000 | Anderson et al. |
| 6,066,448 A | 5/2000 | Wohlstadter et al. |
| 6,067,474 A | 5/2000 | Schulman et al. |
| 6,068,615 A | 5/2000 | Brown et al. |
| D426,638 S | 6/2000 | Ray et al. |
| D427,312 S | 6/2000 | Douglas |
| 6,071,249 A | 6/2000 | Cunningham et al. |
| 6,071,251 A | 6/2000 | Cunningham et al. |
| 6,071,294 A | 6/2000 | Simons et al. |
| 6,071,391 A | 6/2000 | Gotoh et al. |
| 6,071,406 A | 6/2000 | Tsou |
| 6,073,049 A | 6/2000 | Alt et al. |
| 6,081,735 A | 6/2000 | Diab et al. |
| 6,081,736 A | 6/2000 | Colvin et al. |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,156 A | 7/2000 | Cunningham et al. |
| 6,093,167 A | 7/2000 | Houben et al. |
| 6,093,172 A | 7/2000 | Funderburk et al. |
| 6,097,831 A | 8/2000 | Wieck et al. |
| 6,099,484 A | 8/2000 | Douglas et al. |
| 6,101,478 A | 8/2000 | Brown |
| 6,103,033 A | 8/2000 | Say et al. |
| 6,103,533 A | 8/2000 | Hassard et al. |
| 6,106,780 A | 8/2000 | Douglas et al. |
| 6,107,083 A | 8/2000 | Collins et al. |
| 6,110,148 A | 8/2000 | Brown et al. |
| 6,110,152 A | 8/2000 | Kovelman |
| 6,113,578 A | 9/2000 | Brown |
| 6,115,634 A | 9/2000 | Donders et al. |
| 6,117,290 A | 9/2000 | Say |
| 6,119,028 A | 9/2000 | Schulman et al. |
| 6,120,676 A | 9/2000 | Heller et al. |
| 6,121,009 A | 9/2000 | Heller et al. |
| 6,122,351 A | 9/2000 | Schlueter, Jr. et al. |
| 6,122,536 A | 9/2000 | Sun et al. |
| 6,125,978 A | 10/2000 | Ando et al. |
| 6,134,461 A | 10/2000 | Say et al. |
| 6,134,504 A | 10/2000 | Douglas et al. |
| 6,135,978 A | 10/2000 | Houben et al. |
| 6,139,718 A | 10/2000 | Kurnik et al. |
| 6,141,573 A | 10/2000 | Kurnik et al. |
| 6,142,939 A | 11/2000 | Eppstein et al. |
| 6,142,972 A | 11/2000 | Cheikh |
| 6,143,164 A | 11/2000 | Heller et al. |
| 6,144,837 A | 11/2000 | Quy |
| 6,144,869 A | 11/2000 | Berner et al. |
| 6,144,922 A | 11/2000 | Douglas et al. |
| 6,148,094 A | 11/2000 | Kinsella |
| 6,150,128 A | 11/2000 | Uretsky |
| 6,151,586 A | 11/2000 | Brown |
| 6,153,062 A | 11/2000 | Saito et al. |
| 6,153,069 A | 11/2000 | Pottgen et al. |
| 6,154,675 A | 11/2000 | Juran et al. |
| 6,159,147 A | 12/2000 | Lichter et al. |
| 6,161,095 A | 12/2000 | Brown |
| 6,162,611 A | 12/2000 | Heller et al. |
| 6,162,639 A | 12/2000 | Douglas |
| 6,167,362 A | 12/2000 | Brown et al. |
| 6,167,614 B1 | 1/2001 | Tuttle et al. |
| 6,168,563 B1 | 1/2001 | Brown |
| 6,170,318 B1 | 1/2001 | Lewis |
| 6,171,237 B1 | 1/2001 | Avitall et al. |
| 6,175,752 B1 | 1/2001 | Say et al. |
| 6,180,416 B1 | 1/2001 | Kurnik et al. |
| 6,186,145 B1 | 2/2001 | Brown |
| 6,187,062 B1 | 2/2001 | Oweis et al. |
| 6,189,536 B1 | 2/2001 | Martinez et al. |
| 6,192,891 B1 | 2/2001 | Gravel et al. |
| 6,193,873 B1 | 2/2001 | Ohara et al. |
| D439,242 S | 3/2001 | Brown et al. |
| 6,196,970 B1 | 3/2001 | Brown |
| 6,198,957 B1 | 3/2001 | Green |
| 6,200,265 B1 | 3/2001 | Walsh et al. |
| 6,200,772 B1 | 3/2001 | Vadgama et al. |
| 6,201,979 B1 | 3/2001 | Kurnik et al. |
| 6,201,980 B1 | 3/2001 | Darrow et al. |
| 6,201,993 B1 | 3/2001 | Kruse et al. |
| 6,206,841 B1 | 3/2001 | Cunningham et al. |
| 6,206,856 B1 | 3/2001 | Mahurkar |
| 6,207,400 B1 | 3/2001 | Kwon |
| 6,208,894 B1 | 3/2001 | Schulman et al. |
| 6,210,272 B1 | 4/2001 | Brown |
| 6,210,976 B1 | 4/2001 | Sabbadini |
| 6,212,416 B1 | 4/2001 | Ward et al. |
| 6,212,424 B1 | 4/2001 | Robinson |
| 6,214,185 B1 | 4/2001 | Offenbacher et al. |
| 6,219,565 B1 | 4/2001 | Cupp et al. |
| 6,219,574 B1 | 4/2001 | Cormier et al. |

(56) References Cited

U.S. PATENT DOCUMENTS

| | | |
|---|---|---|
| 6,223,083 B1 | 4/2001 | Rosar |
| 6,223,471 B1 | 5/2001 | Barber |
| 6,224,745 B1 | 5/2001 | Baltruschat |
| 6,230,059 B1 | 5/2001 | Duffin |
| 6,231,879 B1 | 5/2001 | Li et al. |
| 6,232,130 B1 | 5/2001 | Wolf |
| 6,232,370 B1 | 5/2001 | Kubota et al. |
| 6,232,783 B1 | 5/2001 | Merrill |
| 6,233,080 B1 | 5/2001 | Brenner et al. |
| 6,233,471 B1 | 5/2001 | Berner et al. |
| 6,233,539 B1 | 5/2001 | Brown |
| 6,239,925 B1 | 5/2001 | Ardrey et al. |
| 6,241,704 B1 | 6/2001 | Peterson et al. |
| 6,241,862 B1 | 6/2001 | McAleer et al. |
| 6,241,863 B1 | 6/2001 | Monbouquette |
| 6,246,330 B1 | 6/2001 | Nielsen |
| 6,246,992 B1 | 6/2001 | Brown |
| 6,248,065 B1 | 6/2001 | Brown |
| 6,248,067 B1 | 6/2001 | Causey, III et al. |
| 6,248,093 B1 | 6/2001 | Moberg |
| 6,249,809 B1 | 6/2001 | Bro |
| 6,251,260 B1 | 6/2001 | Heller et al. |
| 6,251,280 B1 | 6/2001 | Dai et al. |
| 6,252,032 B1 | 6/2001 | Van Antwerp et al. |
| 6,253,804 B1 | 7/2001 | Safabash |
| 6,254,586 B1 | 7/2001 | Mann et al. |
| 6,256,522 B1 | 7/2001 | Schultz |
| 6,256,643 B1 | 7/2001 | Cork et al. |
| 6,259,587 B1 | 7/2001 | Sheldon et al. |
| 6,259,937 B1 | 7/2001 | Schulman et al. |
| 6,260,022 B1 | 7/2001 | Brown |
| 6,264,825 B1 | 7/2001 | Blackburn et al. |
| 6,266,645 B1 | 7/2001 | Simpson |
| 6,267,724 B1 | 7/2001 | Taylor |
| 6,268,161 B1 | 7/2001 | Han et al. |
| 6,268,913 B1 | 7/2001 | Rising |
| 6,270,445 B1 | 8/2001 | Dean, Jr. et al. |
| 6,270,455 B1 | 8/2001 | Brown |
| 6,272,364 B1 | 8/2001 | Kurnik |
| 6,272,480 B1 | 8/2001 | Tresp et al. |
| 6,274,285 B1 | 8/2001 | Gries et al. |
| 6,274,686 B1 | 8/2001 | Mosbach |
| 6,275,717 B1 | 8/2001 | Gross et al. |
| 6,280,416 B1 | 8/2001 | Van Antwerp et al. |
| 6,280,587 B1 | 8/2001 | Matsumoto |
| 6,281,006 B1 | 8/2001 | Heller et al. |
| 6,283,943 B1 | 9/2001 | Dy et al. |
| 6,284,126 B1 | 9/2001 | Kurnik et al. |
| 6,284,478 B1 | 9/2001 | Heller et al. |
| 6,285,897 B1 | 9/2001 | Kilcoyne et al. |
| 6,292,783 B1 | 9/2001 | Rohler et al. |
| 6,293,925 B1 | 9/2001 | Safabash et al. |
| 6,294,281 B1 | 9/2001 | Heller |
| 6,295,463 B1 | 9/2001 | Stenzler |
| 6,295,506 B1 | 9/2001 | Heinonen et al. |
| 6,298,254 B2 | 10/2001 | Tamada |
| 6,299,578 B1 | 10/2001 | Kurnik et al. |
| 6,299,757 B1 | 10/2001 | Feldman et al. |
| 6,300,002 B1 | 10/2001 | Webb et al. |
| 6,301,499 B1 | 10/2001 | Carlson et al. |
| 6,304,766 B1 | 10/2001 | Colvin, Jr. et al. |
| 6,309,351 B1 | 10/2001 | Kurnik et al. |
| 6,309,384 B1 | 10/2001 | Harrington et al. |
| 6,309,526 B1 | 10/2001 | Fujiwara et al. |
| 6,309,884 B1 | 10/2001 | Cooper et al. |
| 6,310,110 B1 | 10/2001 | Markowitz et al. |
| 6,315,721 B2 | 11/2001 | Schulman et al. |
| 6,315,738 B1 | 11/2001 | Nishikawa et al. |
| 6,319,540 B1 | 11/2001 | Van Antwerp et al. |
| 6,319,566 B1 | 11/2001 | Polanyi et al. |
| 6,320,357 B1 | 11/2001 | Peters et al. |
| 6,324,428 B1 | 11/2001 | Weinberg et al. |
| 6,325,978 B1 | 12/2001 | Labuda et al. |
| 6,325,979 B1 | 12/2001 | Hahn et al. |
| 6,326,160 B1 | 12/2001 | Dunn et al. |
| 6,329,161 B1 | 12/2001 | Heller et al. |
| 6,329,929 B1 | 12/2001 | Weijand et al. |
| 6,330,426 B2 | 12/2001 | Brown et al. |
| 6,330,464 B1 | 12/2001 | Colvin, Jr. et al. |
| 6,331,518 B2 | 12/2001 | Hemm et al. |
| 6,334,778 B1 | 1/2002 | Brown |
| 6,336,900 B1 | 1/2002 | Alleckson et al. |
| 6,338,790 B1 | 1/2002 | Feldman et al. |
| 6,340,421 B1 | 1/2002 | Vachon et al. |
| 6,341,232 B1 | 1/2002 | Conn et al. |
| 6,343,225 B1 | 1/2002 | Clark, Jr. |
| 6,356,776 B1 | 3/2002 | Berner et al. |
| 6,358,237 B1 | 3/2002 | Paukovits et al. |
| 6,360,888 B1 | 3/2002 | McIvor et al. |
| 6,361,960 B1 | 3/2002 | Pliszka et al. |
| 6,363,282 B1 | 3/2002 | Nichols et al. |
| 6,365,670 B1 | 4/2002 | Fry |
| 6,366,793 B1 | 4/2002 | Bell et al. |
| 6,366,794 B1 | 4/2002 | Moussy et al. |
| 6,368,141 B1 | 4/2002 | VanAntwerp et al. |
| 6,368,274 B1 | 4/2002 | Van Antwerp et al. |
| 6,370,410 B2 | 4/2002 | Kurnik et al. |
| 6,379,301 B1 | 4/2002 | Worthington et al. |
| 6,379,317 B1 | 4/2002 | Kintzig et al. |
| 6,383,767 B1 | 5/2002 | Polak |
| 6,387,048 B1 | 5/2002 | Schulman et al. |
| 6,389,461 B1 | 5/2002 | Shah |
| 6,391,643 B1 | 5/2002 | Chen et al. |
| 6,393,318 B1 | 5/2002 | Chen et al. |
| 6,398,562 B1 | 6/2002 | Butler et al. |
| 6,398,727 B1 | 6/2002 | Bui et al. |
| 6,402,689 B1 | 6/2002 | Scarantino et al. |
| 6,402,691 B1 | 6/2002 | Peddicord et al. |
| 6,405,066 B1 | 6/2002 | Essenpreis et al. |
| 6,406,066 B1 | 6/2002 | Uegene |
| 6,406,426 B1 | 6/2002 | Reuss et al. |
| 6,409,674 B1 | 6/2002 | Brockway et al. |
| 6,413,393 B1 | 7/2002 | Van Antwerp et al. |
| 6,416,471 B1 | 7/2002 | Kumar et al. |
| 6,418,332 B1 | 7/2002 | Mastrototaro et al. |
| 6,418,346 B1 | 7/2002 | Nelson et al. |
| 6,424,847 B1 * | 7/2002 | Mastrototaro ..... A61B 5/14532 600/316 |
| 6,424,867 B1 | 7/2002 | Snell et al. |
| 6,427,088 B1 | 7/2002 | Bowman, IV et al. |
| 6,434,409 B1 | 8/2002 | Pfeiffer et al. |
| 6,438,414 B1 | 8/2002 | Conn et al. |
| 6,440,068 B1 | 8/2002 | Brown et al. |
| 6,442,433 B1 | 8/2002 | Linberg |
| 6,442,637 B1 | 8/2002 | Hawkins et al. |
| 6,443,942 B2 | 9/2002 | Van Antwerp et al. |
| 6,447,448 B1 | 9/2002 | Ishikawa et al. |
| 6,447,542 B1 | 9/2002 | Weadock |
| 6,454,705 B1 | 9/2002 | Cosentino et al. |
| 6,454,710 B1 | 9/2002 | Ballerstadt et al. |
| 6,459,917 B1 | 10/2002 | Gowda et al. |
| 6,461,496 B1 | 10/2002 | Feldman et al. |
| 6,462,162 B2 | 10/2002 | Van Antwerp et al. |
| 6,464,687 B1 | 10/2002 | Ishikawa et al. |
| 6,464,848 B1 | 10/2002 | Matsumoto |
| 6,466,810 B1 | 10/2002 | Ward et al. |
| 6,468,222 B1 | 10/2002 | Mault et al. |
| 6,469,526 B1 | 10/2002 | Franklin |
| 6,471,645 B1 | 10/2002 | Warkentin et al. |
| 6,471,689 B1 | 10/2002 | Joseph et al. |
| 6,472,122 B1 | 10/2002 | Schulman et al. |
| 6,475,180 B2 | 11/2002 | Peterson et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,478,736 B1 | 11/2002 | Mault |
| 6,480,730 B2 | 11/2002 | Darrow et al. |
| 6,481,440 B2 | 11/2002 | Gielen et al. |
| 6,482,158 B2 | 11/2002 | Mault |
| 6,482,604 B2 | 11/2002 | Kwon |
| 6,484,045 B1 | 11/2002 | Holker et al. |
| 6,484,046 B1 | 11/2002 | Say et al. |
| 6,485,138 B1 | 11/2002 | Kubota et al. |
| 6,485,465 B2 | 11/2002 | Moberg et al. |

(56) References Cited

U.S. PATENT DOCUMENTS

| | | |
|---|---|---|
| 6,494,830 B1 | 12/2002 | Wessel |
| 6,496,728 B2 | 12/2002 | Li et al. |
| 6,498,043 B1 | 12/2002 | Schulman et al. |
| 6,498,941 B1 | 12/2002 | Jackson |
| 6,505,059 B1 | 1/2003 | Kollias et al. |
| 6,512,939 B1 | 1/2003 | Colvin et al. |
| 6,513,532 B2 | 2/2003 | Mault et al. |
| 6,514,718 B2 | 2/2003 | Heller et al. |
| 6,515,593 B1 | 2/2003 | Stark et al. |
| 6,519,241 B1 | 2/2003 | Theimer |
| 6,520,326 B2 | 2/2003 | McIvor et al. |
| 6,520,997 B1 | 2/2003 | Pekkarinen et al. |
| 6,526,298 B1 | 2/2003 | Khalil et al. |
| 6,527,729 B1 | 3/2003 | Turcott |
| 6,528,584 B2 | 3/2003 | Kennedy et al. |
| 6,529,755 B2 | 3/2003 | Kurnik et al. |
| 6,529,772 B2 | 3/2003 | Carlson et al. |
| 6,530,915 B1 | 3/2003 | Eppstein et al. |
| 6,534,322 B1 | 3/2003 | Sabbadini |
| 6,534,323 B1 | 3/2003 | Sabbadini |
| 6,535,753 B1 | 3/2003 | Raskas |
| 6,537,243 B1 | 3/2003 | Henning et al. |
| 6,537,318 B1 | 3/2003 | Ita et al. |
| 6,540,672 B1 | 4/2003 | Simonsen et al. |
| 6,540,675 B2 | 4/2003 | Aceti et al. |
| 6,541,107 B1 | 4/2003 | Zhong et al. |
| 6,544,212 B2 | 4/2003 | Galley et al. |
| 6,545,085 B2 | 4/2003 | Kilgour et al. |
| 6,546,232 B1 | 4/2003 | Sack et al. |
| 6,546,268 B1 | 4/2003 | Ishikawa et al. |
| 6,546,269 B1 | 4/2003 | Kurnik |
| 6,547,839 B2 | 4/2003 | Zhang et al. |
| 6,549,796 B2 | 4/2003 | Sohrab |
| 6,551,276 B1 | 4/2003 | Mann et al. |
| 6,551,494 B1 | 4/2003 | Heller et al. |
| 6,551,496 B1 | 4/2003 | Moles et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,569,521 B1 | 5/2003 | Sheridan et al. |
| 6,571,128 B2 | 5/2003 | Lebel et al. |
| 6,571,200 B1 | 5/2003 | Mault |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,576,101 B1 | 6/2003 | Heller et al. |
| 6,576,117 B1 | 6/2003 | Iketaki et al. |
| 6,577,899 B2 | 6/2003 | Lebel et al. |
| 6,579,231 B1 | 6/2003 | Phipps |
| 6,579,498 B1 | 6/2003 | Eglise |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,585,675 B1 | 7/2003 | O'Mahony et al. |
| 6,585,763 B1 | 7/2003 | Keilman et al. |
| 6,587,705 B1 | 7/2003 | Kim et al. |
| 6,588,644 B2 | 7/2003 | Simon |
| 6,589,205 B1 | 7/2003 | Meadows |
| 6,589,229 B1 | 7/2003 | Connelly et al. |
| 6,591,125 B1 | 7/2003 | Buse et al. |
| 6,591,126 B2 | 7/2003 | Roeper et al. |
| 6,594,514 B2 | 7/2003 | Berner et al. |
| 6,595,919 B2 | 7/2003 | Berner et al. |
| 6,595,929 B2 | 7/2003 | Stivoric et al. |
| 6,602,191 B2 | 8/2003 | Quy |
| 6,602,678 B2 | 8/2003 | Kwon et al. |
| 6,602,909 B1 | 8/2003 | Jarowski |
| 6,605,072 B2 | 8/2003 | Struys et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,607,658 B1 | 8/2003 | Heller et al. |
| 6,610,012 B2 | 8/2003 | Mault |
| 6,612,306 B1 | 9/2003 | Mault |
| 6,612,984 B1 | 9/2003 | Kerr |
| 6,613,379 B2 | 9/2003 | Ward et al. |
| 6,615,078 B1 | 9/2003 | Burson et al. |
| 6,616,819 B1 | 9/2003 | Liamos et al. |
| 6,618,603 B2 | 9/2003 | Varalli et al. |
| 6,618,934 B1 | 9/2003 | Feldman et al. |
| 6,620,106 B2 | 9/2003 | Mault |
| 6,627,058 B1 | 9/2003 | Chan |
| 6,629,934 B2 | 10/2003 | Mault et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,642,015 B2 | 11/2003 | Vachon et al. |
| 6,644,321 B1 | 11/2003 | Behm |
| 6,645,142 B2 | 11/2003 | Braig et al. |
| 6,645,181 B1 | 11/2003 | Lavi et al. |
| 6,648,821 B2 | 11/2003 | Lebel et al. |
| 6,653,091 B1 | 11/2003 | Dunn et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,671,554 B2 | 12/2003 | Gibson et al. |
| 6,673,596 B1 | 1/2004 | Sayler et al. |
| 6,673,625 B2 | 1/2004 | Satcher, Jr. et al. |
| 6,682,938 B1 | 1/2004 | Satcher, Jr. et al. |
| 6,683,040 B2 | 1/2004 | Bragulla et al. |
| 6,683,535 B1 | 1/2004 | Utke |
| 6,687,522 B2 | 2/2004 | Tamada |
| 6,687,546 B2 | 2/2004 | Lebel et al. |
| 6,689,056 B1 | 2/2004 | Kilcoyne et al. |
| 6,689,091 B2 | 2/2004 | Bui et al. |
| 6,689,265 B2 | 2/2004 | Heller et al. |
| 6,693,069 B2 | 2/2004 | Korber et al. |
| 6,694,158 B2 | 2/2004 | Polak |
| 6,694,191 B2 | 2/2004 | Starkweather et al. |
| 6,695,860 B1 | 2/2004 | Ward et al. |
| 6,699,188 B2 | 3/2004 | Wessel |
| 6,699,218 B2 | 3/2004 | Flaherty et al. |
| 6,699,383 B2 | 3/2004 | Lemire et al. |
| 6,702,857 B2 | 3/2004 | Brauker et al. |
| 6,704,587 B1 | 3/2004 | Kumar et al. |
| 6,705,833 B2 | 3/2004 | Tam et al. |
| 6,708,049 B1 | 3/2004 | Berson et al. |
| 6,711,423 B2 | 3/2004 | Colvin, Jr. |
| 6,721,587 B2 | 4/2004 | Gough |
| 6,723,046 B2 | 4/2004 | Lichtenstein et al. |
| 6,728,560 B2 | 4/2004 | Kollias et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,734,162 B2 | 5/2004 | Van Antwerp et al. |
| 6,735,551 B2 | 5/2004 | Voegeli et al. |
| 6,736,777 B2 | 5/2004 | Kim et al. |
| 6,737,401 B2 | 5/2004 | Kim et al. |
| 6,738,654 B2 | 5/2004 | Sohrab |
| 6,740,075 B2 | 5/2004 | Lebel et al. |
| 6,741,163 B1 | 5/2004 | Roberts |
| 6,741,876 B1 | 5/2004 | Scecina et al. |
| 6,741,877 B1 | 5/2004 | Shults et al. |
| 6,749,587 B2 | 6/2004 | Flaherty |
| 6,750,311 B1 | 6/2004 | Van Antwerp et al. |
| 6,758,810 B2 | 7/2004 | Lebel et al. |
| 6,766,183 B2 | 7/2004 | Walsh et al. |
| 6,766,201 B2 | 7/2004 | Von Arx et al. |
| 6,768,425 B2 | 7/2004 | Flaherty et al. |
| 6,770,030 B1 | 8/2004 | Schaupp et al. |
| 6,770,729 B2 | 8/2004 | Van Antwerp et al. |
| 6,771,995 B2 | 8/2004 | Kurnik et al. |
| 6,773,563 B2 | 8/2004 | Matsumoto |
| 6,773,565 B2 | 8/2004 | Kunimoto et al. |
| 6,780,297 B2 | 8/2004 | Matsumoto et al. |
| 6,780,871 B2 | 8/2004 | Glick et al. |

(56) References Cited

U.S. PATENT DOCUMENTS

| | | |
|---|---|---|
| 6,784,274 B2 | 8/2004 | Van Antwerp et al. |
| 6,790,178 B1 | 9/2004 | Mault et al. |
| 6,793,802 B2 | 9/2004 | Lee et al. |
| 6,794,195 B2 | 9/2004 | Colvin, Jr. |
| 6,799,149 B2 | 9/2004 | Hartlaub |
| 6,800,451 B2 | 10/2004 | Daniloff et al. |
| 6,801,041 B2 | 10/2004 | Karinka et al. |
| 6,801,420 B2 | 10/2004 | Talbot et al. |
| 6,802,957 B2 | 10/2004 | Jung et al. |
| 6,804,544 B2 | 10/2004 | Van Antwerp et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,659 B2 | 11/2004 | Vachon |
| 6,812,031 B1 | 11/2004 | Carlsson |
| 6,813,516 B2 | 11/2004 | Ujhelyi et al. |
| 6,813,519 B2 | 11/2004 | Lebel et al. |
| 6,815,186 B2 | 11/2004 | Clark, Jr. |
| 6,816,742 B2 | 11/2004 | Kim et al. |
| 6,835,553 B2 | 12/2004 | Han et al. |
| RE38,681 E | 1/2005 | Kurnik et al. |
| 6,840,912 B2 | 1/2005 | Kloepfer et al. |
| 6,844,023 B2 | 1/2005 | Schulman et al. |
| 6,849,045 B2 | 2/2005 | Iliff |
| 6,849,237 B2 | 2/2005 | Housefield et al. |
| 6,850,790 B2 | 2/2005 | Berner et al. |
| 6,852,500 B1 | 2/2005 | Hoss et al. |
| 6,852,694 B2 | 2/2005 | Van Antwerp et al. |
| 6,853,854 B1 | 2/2005 | Proniewicz et al. |
| 6,855,115 B2 | 2/2005 | Fonseca et al. |
| 6,856,928 B2 | 2/2005 | Harmon |
| 6,858,403 B2 | 2/2005 | Han et al. |
| 6,862,465 B2 | 3/2005 | Shults et al. |
| 6,862,466 B2 | 3/2005 | Ackerman |
| 6,872,200 B2 | 3/2005 | Mann et al. |
| 6,873,268 B2 | 3/2005 | Lebel et al. |
| 6,875,386 B1 | 4/2005 | Ward et al. |
| 6,879,849 B2 | 4/2005 | Begic |
| 6,881,551 B2 | 4/2005 | Heller et al. |
| 6,882,940 B2 | 4/2005 | Potts et al. |
| 6,885,883 B2 | 4/2005 | Parris et al. |
| 6,891,317 B2 | 5/2005 | Pei et al. |
| 6,891,936 B2 | 5/2005 | Kai et al. |
| 6,892,085 B2 | 5/2005 | McIvor et al. |
| 6,893,552 B1 | 5/2005 | Wang et al. |
| 6,895,263 B2 | 5/2005 | Shin et al. |
| 6,899,683 B2 | 5/2005 | Mault et al. |
| 6,899,684 B2 | 5/2005 | Mault et al. |
| 6,902,905 B2 | 6/2005 | Burson et al. |
| 6,904,301 B2 | 6/2005 | Raskas |
| 6,907,127 B1 | 6/2005 | Kravitz et al. |
| 6,915,147 B2 | 7/2005 | Lebel et al. |
| 6,918,769 B2 | 7/2005 | Rink |
| 6,918,874 B1 | 7/2005 | Hatch et al. |
| 6,922,578 B2 | 7/2005 | Eppstein et al. |
| 6,922,584 B2 | 7/2005 | Wang et al. |
| RE38,775 E | 8/2005 | Kurnik et al. |
| 6,923,764 B2 | 8/2005 | Aceti et al. |
| 6,923,936 B2 | 8/2005 | Swanson et al. |
| 6,927,246 B2 | 8/2005 | Noronha et al. |
| 6,931,327 B2 | 8/2005 | Goode, Jr. et al. |
| 6,932,084 B2 | 8/2005 | Estes et al. |
| 6,932,894 B2 | 8/2005 | Mao et al. |
| 6,936,006 B2 | 8/2005 | Sabra |
| 6,936,029 B2 | 8/2005 | Mann et al. |
| 6,940,590 B2 | 9/2005 | Colvin, Jr. et al. |
| 6,941,163 B2 | 9/2005 | Ford et al. |
| 6,946,996 B2 | 9/2005 | Koyama |
| 6,950,708 B2 | 9/2005 | Bowman, IV et al. |
| 6,952,603 B2 | 10/2005 | Gerber et al. |
| 6,954,673 B2 | 10/2005 | Von Arx et al. |
| 6,955,650 B2 | 10/2005 | Mault et al. |
| 6,957,102 B2 | 10/2005 | Silver et al. |
| 6,957,107 B2 | 10/2005 | Rogers et al. |
| 6,958,705 B2 | 10/2005 | Lebel et al. |
| 6,965,791 B1 | 11/2005 | Hitchcock et al. |
| 6,968,294 B2 | 11/2005 | Gutta et al. |
| 6,968,375 B1 | 11/2005 | Brown |
| 6,973,706 B2 | 12/2005 | Say et al. |
| 6,974,437 B2 | 12/2005 | Lebel et al. |
| 6,978,182 B2 | 12/2005 | Mazar et al. |
| 6,979,326 B2 | 12/2005 | Mann et al. |
| 6,990,366 B2 | 1/2006 | Say et al. |
| 6,991,096 B2 | 1/2006 | Gottlieb et al. |
| 6,997,907 B2 | 2/2006 | Safabash et al. |
| 6,997,920 B2 | 2/2006 | Mann et al. |
| 6,998,247 B2 | 2/2006 | Monfre et al. |
| 6,999,810 B2 | 2/2006 | Berner et al. |
| 7,003,336 B2 | 2/2006 | Holker et al. |
| 7,003,341 B2 | 2/2006 | Say et al. |
| 7,004,901 B2 | 2/2006 | Fish |
| 7,005,857 B2 | 2/2006 | Stiene et al. |
| 7,011,630 B2 | 3/2006 | Desai et al. |
| 7,016,721 B2 | 3/2006 | Lee et al. |
| 7,018,366 B2 | 3/2006 | Easter |
| 7,018,568 B2 | 3/2006 | Tierney |
| 7,022,072 B2 | 4/2006 | Fox et al. |
| 7,024,236 B2 | 4/2006 | Ford et al. |
| 7,024,245 B2 | 4/2006 | Lebel et al. |
| 7,025,743 B2 | 4/2006 | Mann et al. |
| 7,029,444 B2 | 4/2006 | Shin et al. |
| 7,039,810 B1 | 5/2006 | Nichols |
| 7,041,468 B2 | 5/2006 | Drucker et al. |
| 7,043,305 B2 | 5/2006 | KenKnight et al. |
| 7,049,277 B2 | 5/2006 | Bagulla et al. |
| 7,052,472 B1 | 5/2006 | Miller et al. |
| 7,052,483 B2 | 5/2006 | Wojcik |
| 7,056,302 B2 | 6/2006 | Douglas |
| 7,070,580 B2 | 7/2006 | Nielsen |
| 7,072,718 B2 | 7/2006 | VonArx et al. |
| 7,072,802 B2 | 7/2006 | Hartlaub |
| 7,074,307 B2 | 7/2006 | Simpson et al. |
| 7,077,806 B2 | 7/2006 | Ackermann et al. |
| 7,081,195 B2 | 7/2006 | Simpson et al. |
| 7,082,334 B2 | 7/2006 | Boute et al. |
| 7,098,803 B2 | 8/2006 | Mann et al. |
| 7,108,778 B2 | 9/2006 | Simpson et al. |
| 7,109,878 B2 | 9/2006 | Mann et al. |
| 7,110,803 B2 | 9/2006 | Shults et al. |
| 7,113,821 B1 | 9/2006 | Sun et al. |
| 7,115,884 B1 | 10/2006 | Walt et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,137,964 B2 | 11/2006 | Flaherty |
| 7,150,975 B2 | 12/2006 | Tamada et al. |
| 7,163,511 B2 | 1/2007 | Conn et al. |
| 7,166,074 B2 | 1/2007 | Reghabit et al. |
| 7,171,274 B2 | 1/2007 | Starkweather et al. |
| 7,177,690 B2 | 2/2007 | Woods et al. |
| 7,183,068 B2 | 2/2007 | Burson et al. |
| 7,183,102 B2 | 2/2007 | Monfre et al. |
| 7,187,528 B2 | 3/2007 | Talbot et al. |
| 7,189,341 B2 | 3/2007 | Li et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,226,978 B2 | 6/2007 | Tapsak et al. |
| 7,228,163 B2 | 6/2007 | Ackerman |
| 7,233,817 B2 | 6/2007 | Yen |
| 7,248,929 B2 | 7/2007 | Meadows et al. |
| 7,261,691 B1 | 8/2007 | Asomani |
| 7,267,665 B2 | 9/2007 | Steil et al. |
| 7,276,029 B2 | 10/2007 | Goode, Jr. et al. |
| 7,286,894 B1 | 10/2007 | Grant et al. |
| 7,287,031 B1 | 10/2007 | Karpf et al. |
| 7,295,867 B2 | 11/2007 | Berner et al. |
| 7,297,108 B2 | 11/2007 | Iliff |
| 7,310,544 B2 | 12/2007 | Brister et al. |
| 7,353,179 B2 | 4/2008 | Ott et al. |

(56) References Cited

U.S. PATENT DOCUMENTS

| | | |
|---|---|---|
| 7,448,996 B2 | 11/2008 | Khanuja et al. |
| 2001/0005830 A1 | 6/2001 | Kuroyanagi |
| 2001/0011224 A1 | 8/2001 | Brown |
| 2001/0016310 A1 | 8/2001 | Brown et al. |
| 2001/0016682 A1 | 8/2001 | Berner et al. |
| 2001/0016683 A1 | 8/2001 | Darrow et al. |
| 2001/0020124 A1 | 9/2001 | Tamada |
| 2001/0029340 A1 | 10/2001 | Mault et al. |
| 2001/0032278 A1 | 10/2001 | Brown et al. |
| 2001/0037060 A1 | 11/2001 | Thompson et al. |
| 2001/0037069 A1 | 11/2001 | Carlson et al. |
| 2001/0039504 A1 | 11/2001 | Linberg et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0047125 A1 | 11/2001 | Quy |
| 2001/0049096 A1 | 12/2001 | Brown |
| 2001/0049470 A1 | 12/2001 | Mault et al. |
| 2001/0051787 A1 | 12/2001 | Haller et al. |
| 2001/0056328 A1 | 12/2001 | Trippel et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0009810 A1 | 1/2002 | O'Connor et al. |
| 2002/0010414 A1 | 1/2002 | Coston et al. |
| 2002/0016530 A1 | 2/2002 | Brown |
| 2002/0019022 A1 | 2/2002 | Dunn et al. |
| 2002/0019330 A1 | 2/2002 | Murray et al. |
| 2002/0019586 A1 | 2/2002 | Teller et al. |
| 2002/0019748 A1 | 2/2002 | Brown |
| 2002/0022883 A1 | 2/2002 | Burg |
| 2002/0023852 A1 | 2/2002 | McIvor et al. |
| 2002/0026111 A1 | 2/2002 | Ackerman |
| 2002/0026937 A1 | 3/2002 | Mault |
| 2002/0027164 A1 | 3/2002 | Mault et al. |
| 2002/0028995 A1 | 3/2002 | Mault |
| 2002/0040208 A1 | 4/2002 | Flaherty et al. |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0063060 A1 | 5/2002 | Gascoyne et al. |
| 2002/0065453 A1 | 5/2002 | Lesho et al. |
| 2002/0068858 A1 | 6/2002 | Braig et al. |
| 2002/0068860 A1 | 6/2002 | Clark, Jr. |
| 2002/0072858 A1 | 6/2002 | Cheng |
| 2002/0077765 A1 | 6/2002 | Mault |
| 2002/0077766 A1 | 6/2002 | Mault |
| 2002/0081559 A1 | 6/2002 | Brown et al. |
| 2002/0083461 A1 | 6/2002 | Hutcheson et al. |
| 2002/0087056 A1 | 7/2002 | Aceti et al. |
| 2002/0091312 A1 | 7/2002 | Berner et al. |
| 2002/0099282 A1 | 7/2002 | Knobbe et al. |
| 2002/0099997 A1 | 7/2002 | Piret |
| 2002/0103425 A1 | 8/2002 | Mault |
| 2002/0107433 A1 | 8/2002 | Mault |
| 2002/0107476 A1 | 8/2002 | Mann et al. |
| 2002/0109600 A1 | 8/2002 | Mault et al. |
| 2002/0111547 A1 | 8/2002 | Knobbe et al. |
| 2002/0119711 A1 | 8/2002 | Van Antwerp et al. |
| 2002/0124017 A1 | 9/2002 | Mault |
| 2002/0128594 A1 | 9/2002 | Das et al. |
| 2002/0130042 A1 | 9/2002 | Moerman et al. |
| 2002/0133378 A1 | 9/2002 | Mault et al. |
| 2002/0143241 A1 | 10/2002 | Thorell |
| 2002/0151796 A1 | 10/2002 | Koulik |
| 2002/0151816 A1 | 10/2002 | Rich et al. |
| 2002/0155615 A1 | 10/2002 | Novikov et al. |
| 2002/0161286 A1 | 10/2002 | Gerber et al. |
| 2002/0161288 A1 | 10/2002 | Shin et al. |
| 2002/0177764 A1 | 11/2002 | Sohrab |
| 2002/0182241 A1 | 12/2002 | Boerenstein et al. |
| 2002/0186243 A1 | 12/2002 | Ellis et al. |
| 2002/0188466 A1 | 12/2002 | Barrette et al. |
| 2002/0193885 A1 | 12/2002 | Legeay et al. |
| 2002/0198513 A1 | 12/2002 | Lebel et al. |
| 2003/0004457 A1 | 1/2003 | Andersson |
| 2003/0006669 A1 | 1/2003 | Pei et al. |
| 2003/0023171 A1 | 1/2003 | Sato et al. |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032077 A1 | 2/2003 | Itoh et al. |
| 2003/0032867 A1 | 2/2003 | Crothall et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0042137 A1 | 3/2003 | Mao et al. |
| 2003/0050537 A1 | 3/2003 | Wessel |
| 2003/0050546 A1 | 3/2003 | Desai et al. |
| 2003/0059631 A1 | 3/2003 | Al-Lamee |
| 2003/0065254 A1 | 4/2003 | Schulman et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0097082 A1 | 5/2003 | Purdy et al. |
| 2003/0100040 A1 | 5/2003 | Bonnecaze et al. |
| 2003/0100821 A1 | 5/2003 | Heller et al. |
| 2003/0101078 A1 | 5/2003 | Voegeli et al. |
| 2003/0105407 A1 | 6/2003 | Pearce et al. |
| 2003/0108976 A1 | 6/2003 | Braig et al. |
| 2003/0125612 A1 | 7/2003 | Fox et al. |
| 2003/0125613 A1 | 7/2003 | Enegren et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158707 A1 | 8/2003 | Doi |
| 2003/0168338 A1 | 9/2003 | Gao et al. |
| 2003/0175806 A1 | 9/2003 | Rule et al. |
| 2003/0176183 A1 | 9/2003 | Drucker et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0188427 A1 | 10/2003 | Say et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0199744 A1 | 10/2003 | Buse et al. |
| 2003/0199791 A1 | 10/2003 | Boecker et al. |
| 2003/0199903 A1 | 10/2003 | Boecker et al. |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208409 A1 | 11/2003 | Mault |
| 2003/0211625 A1 | 11/2003 | Cohan |
| 2003/0212346 A1 | 11/2003 | Yuzhakov et al. |
| 2003/0212364 A1 | 11/2003 | Mann et al. |
| 2003/0212379 A1 | 11/2003 | Bylund et al. |
| 2003/0217966 A1 | 11/2003 | Tapsak et al. |
| 2003/0225437 A1 | 12/2003 | Ferguson |
| 2003/0226695 A1 | 12/2003 | Mault |
| 2003/0229514 A2 | 12/2003 | Brown |
| 2003/0232370 A1 | 12/2003 | Trifiro |
| 2003/0235817 A1 | 12/2003 | Bartkowiak et al. |
| 2004/0010207 A1 | 1/2004 | Flaherty et al. |
| 2004/0011671 A1 | 1/2004 | Shults et al. |
| 2004/0015134 A1 | 1/2004 | Lavi et al. |
| 2004/0018486 A1 | 1/2004 | Dunn et al. |
| 2004/0030285 A1 | 2/2004 | Lavi et al. |

(56) References Cited

U.S. PATENT DOCUMENTS

| | | |
|---|---|---|
| 2004/0030294 A1 | 2/2004 | Mahurkar |
| 2004/0039256 A1 | 2/2004 | Kawatahara et al. |
| 2004/0039406 A1 | 2/2004 | Jessen |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0068230 A1 | 4/2004 | Estes et al. |
| 2004/0069164 A1 | 4/2004 | Nakamura et al. |
| 2004/0072357 A1 | 4/2004 | Stiene et al. |
| 2004/0073095 A1 | 4/2004 | Causey, III et al. |
| 2004/0074785 A1 | 4/2004 | Holker |
| 2004/0078219 A1 | 4/2004 | Kaylor |
| 2004/0096959 A1 | 5/2004 | Stiene et al. |
| 2004/0106858 A1 | 6/2004 | Say et al. |
| 2004/0106859 A1 | 6/2004 | Say et al. |
| 2004/0108226 A1 | 6/2004 | Polychronakos et al. |
| 2004/0122353 A1 | 6/2004 | Shahmirian et al. |
| 2004/0122489 A1 | 6/2004 | Mazar et al. |
| 2004/0133164 A1 | 7/2004 | Funderburk et al. |
| 2004/0138588 A1 | 7/2004 | Saikley et al. |
| 2004/0153585 A1 | 8/2004 | Kawatahara et al. |
| 2004/0162035 A1 | 8/2004 | Petersen et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167801 A1 | 8/2004 | Say et al. |
| 2004/0171921 A1 | 9/2004 | Say et al. |
| 2004/0172284 A1 | 9/2004 | Sullivan et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0202576 A1 | 10/2004 | Aceti et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254433 A1 | 12/2004 | Bandis et al. |
| 2004/0254434 A1 | 12/2004 | Goodnow et al. |
| 2004/0260363 A1 | 12/2004 | Von Arx et al. |
| 2004/0263354 A1 | 12/2004 | Mann et al. |
| 2005/0003470 A1 | 1/2005 | Nelson et al. |
| 2005/0010087 A1 | 1/2005 | Banet et al. |
| 2005/0010269 A1 | 1/2005 | Lebel et al. |
| 2005/0027177 A1 | 2/2005 | Shin et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0049473 A1 | 3/2005 | Desai et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |
| 2005/0112169 A1 | 5/2005 | Brauker et al. |
| 2005/0113657 A1 | 5/2005 | Alarcon et al. |
| 2005/0113658 A1 | 5/2005 | Jacobson et al. |
| 2005/0118726 A1 | 6/2005 | Schultz et al. |
| 2005/0121322 A1 | 6/2005 | Say et al. |
| 2005/0124873 A1 | 6/2005 | Shults et al. |
| 2005/0131346 A1 | 6/2005 | Douglas |
| 2005/0137471 A1 | 6/2005 | Haar et al. |
| 2005/0143635 A1 | 6/2005 | Kamath et al. |
| 2005/0143636 A1 | 6/2005 | Zhang et al. |
| 2005/0148003 A1 | 7/2005 | Kieth et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0182306 A1 | 8/2005 | Sloan et al. |
| 2005/0182451 A1 | 8/2005 | Griffin et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203707 A1 | 9/2005 | Tsutsui et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0239154 A1 | 10/2005 | Feldman et al. |
| 2005/0239156 A1 | 10/2005 | Drucker et al. |
| 2005/0242479 A1 | 11/2005 | Petisce et al. |
| 2005/0245795 A1 | 11/2005 | Goode, Jr. et al. |
| 2005/0245799 A1 | 11/2005 | Brauker et al. |
| 2005/0251083 A1 | 11/2005 | Carr-Brendel et al. |
| 2005/0261563 A1 | 11/2005 | Zhou et al. |
| 2005/0261660 A1 | 11/2005 | Choi |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277164 A1 | 12/2005 | Drucker et al. |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004271 A1 | 1/2006 | Peyser et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1 | 2/2006 | Talbot et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0052679 A1 | 3/2006 | Kotulla et al. |
| 2006/0058602 A1 | 3/2006 | Kwiatkowski et al. |
| 2006/0063218 A1 | 3/2006 | Bartkowiak et al. |
| 2006/0068208 A1 | 3/2006 | Tapsak et al. |
| 2006/0074564 A1 | 4/2006 | Bartkowiak et al. |
| 2006/0086624 A1 | 4/2006 | Tapsak et al. |
| 2006/0155180 A1 | 7/2006 | Brister et al. |
| 2006/0173444 A1 | 8/2006 | Choy et al. |
| 2006/0189856 A1 | 8/2006 | Petisce et al. |
| 2006/0189863 A1 | 8/2006 | Peyser et al. |

(56) References Cited

U.S. PATENT DOCUMENTS

| | | |
|---|---|---|
| 2006/0195029 A1 | 8/2006 | Shults et al. |
| 2006/0198864 A1 | 9/2006 | Shults et al. |
| 2006/0200019 A1 | 9/2006 | Petisce et al. |
| 2006/0200020 A1 | 9/2006 | Brister et al. |
| 2006/0200022 A1 | 9/2006 | Brauker et al. |
| 2006/0211921 A1 | 9/2006 | Brauker et al. |
| 2006/0222566 A1 | 10/2006 | Brauker et al. |
| 2006/0224108 A1 | 10/2006 | Brauker et al. |
| 2006/0235285 A1 | 10/2006 | Brister et al. |
| 2006/0247985 A1 | 11/2006 | Liamos et al. |
| 2006/0248398 A1 | 11/2006 | Neel et al. |
| 2006/0258761 A1 | 11/2006 | Boock et al. |
| 2006/0258929 A1 | 11/2006 | Goode, Jr. et al. |
| 2006/0270922 A1 | 11/2006 | Brauker et al. |
| 2006/0270923 A1 | 11/2006 | Brauker et al. |
| 2007/0016381 A1 | 1/2007 | Kamath et al. |
| 2007/0017805 A1 | 1/2007 | Hodges et al. |
| 2007/0027381 A1 | 2/2007 | Stafford |
| 2007/0027384 A1 | 2/2007 | Brister et al. |
| 2007/0027385 A1 | 2/2007 | Brister et al. |
| 2007/0032706 A1 | 2/2007 | Kamath et al. |
| 2007/0032717 A1 | 2/2007 | Brister et al. |
| 2007/0032718 A1 | 2/2007 | Shults et al. |
| 2007/0045902 A1 | 3/2007 | Brauker et al. |
| 2007/0060814 A1 | 3/2007 | Stafford |
| 2007/0066873 A1 | 3/2007 | Kamath et al. |
| 2007/0078320 A1 | 4/2007 | Stafford |
| 2007/0078321 A1 | 4/2007 | Mazza et al. |
| 2007/0093704 A1 | 4/2007 | Brister et al. |
| 2007/0106135 A1 | 5/2007 | Sloan et al. |
| 2007/0149873 A1 | 6/2007 | Say et al. |
| 2007/0149874 A1 | 6/2007 | Say et al. |
| 2007/0151869 A1 | 7/2007 | Heller et al. |
| 2007/0161879 A1 | 7/2007 | Say et al. |
| 2007/0161880 A1 | 7/2007 | Say et al. |
| 2007/0163880 A1 | 7/2007 | Woo et al. |
| 2007/0179370 A1 | 8/2007 | Say et al. |
| 2007/0179372 A1 | 8/2007 | Say et al. |
| 2007/0191699 A1 | 8/2007 | Say et al. |
| 2007/0191700 A1 | 8/2007 | Say et al. |
| 2007/0197889 A1 | 8/2007 | Brister et al. |
| 2007/0197890 A1 | 8/2007 | Boock et al. |
| 2007/0203408 A1 | 8/2007 | Say et al. |
| 2007/0203410 A1 | 8/2007 | Say et al. |
| 2007/0203411 A1 | 8/2007 | Say et al. |
| 2007/0203966 A1 | 8/2007 | Brauker et al. |
| 2007/0208247 A1 | 9/2007 | Say et al. |
| 2007/0213610 A1 | 9/2007 | Say et al. |
| 2007/0215491 A1 | 9/2007 | Heller et al. |
| 2007/0218097 A1 | 9/2007 | Heller et al. |
| 2007/0235331 A1 | 10/2007 | Simpson et al. |
| 2007/0244380 A1 | 10/2007 | Say et al. |
| 2007/0249919 A1 | 10/2007 | Say et al. |
| 2007/0249920 A1 | 10/2007 | Say et al. |
| 2007/0249922 A1 | 10/2007 | Peyser et al. |
| 2008/0139910 A1 | 6/2008 | Mastrototaro et al. |

FOREIGN PATENT DOCUMENTS

| | | |
|---|---|---|
| DE | 100 42 101 A1 | 2/2002 |
| EP | 0 504 835 A2 | 3/1992 |
| EP | 0 653 718 | 11/1994 |
| EP | 0 653 718 A2 | 11/1994 |
| EP | 0 800 082 A2 | 10/1997 |
| EP | 0 800 082 A3 | 10/1997 |
| EP | 0 880 936 A2 | 10/1997 |
| EP | 0 970 655 A1 | 1/1998 |
| EP | 1 416 417 A2 | 5/2004 |
| EP | 1965691 | 9/2008 |
| GB | 1 579 690 | 11/1980 |
| GB | 2 194 892 A | 3/1988 |
| GB | 2 225 637 A | 6/1990 |
| JP | 10-166894 | 1/2000 |
| JP | 10-314029 | 4/2000 |
| WO | WO 86/00513 | 1/1986 |
| WO | WO 87/06040 | 10/1987 |
| WO | WO 89/02246 | 3/1989 |
| WO | WO 90/00367 | 1/1990 |
| WO | WO 95/06240 | 3/1995 |
| WO | WO 96/07908 | 3/1996 |
| WO | WO 97/20207 | 6/1997 |
| WO | WO 97/41421 | 11/1997 |
| WO | WO 97/46868 | 12/1997 |
| WO | WO 98/09167 | 3/1998 |
| WO | WO 98/24366 | 6/1998 |
| WO | WO 98/52045 | 11/1998 |
| WO | WO 99/05966 | 2/1999 |
| WO | WO 99/32883 | 7/1999 |
| WO | WO 00/13580 | 3/2000 |
| WO | WO 00/20626 | 4/2000 |
| WO | 00/32258 | 6/2000 |
| WO | WO 00/33065 | 6/2000 |
| WO | 00/49731 | 8/2000 |
| WO | WO 00/78210 | 12/2000 |
| WO | WO 01/15056 | 3/2001 |
| WO | WO 01/24038 | 4/2001 |
| WO | WO 01/33216 | 5/2001 |
| WO | WO 01/52727 | 7/2001 |
| WO | WO 01/57238 | 8/2001 |
| WO | WO 01/57239 | 8/2001 |
| WO | WO 01/67009 | 9/2001 |
| WO | WO 01/89362 | 11/2001 |
| WO | WO 02/056151 | 7/2002 |
| WO | WO 02/078512 A2 | 10/2002 |
| WO | WO 02/082984 | 10/2002 |
| WO | WO 03/017832 | 3/2003 |
| WO | WO 03/039361 | 5/2003 |
| WO | WO 02/078512 A3 | 1/2004 |
| WO | WO 02/078512 A3 | 12/2004 |

OTHER PUBLICATIONS

Schmalzel, J. L., et al., "An Impedance Pneumograph Utilizing Microprocessor-based Instrumentation," Proceedings of the Fourteenth Annual Rocky Mountain Bioengineering Symposium, 1977, vol. 13, pp. 63-68.

Walford, S., et al., "Self-Monitoring of Blood Glucose, Improvement of Diabetic Control," Apr. 8, 1978, The Lancet, pp. 732-735.

Caprihan, A., et al., "A Simple Microcomputer for Biomedical Signal Processing," IECI '78 Annual Conference Proceedings on Industrial Applications of Microprocessors, Mar. 2-22, 1978, pp. 18-23. R.B. Tattersall, "Home Blood Glucose Monitoring," Diabetologia, 1979, vol. 16, No. 2, pp. 71-74.

Santigo, J. V., et al., "Closed-loop and Open-loop Devices for Blood Glucose Control in Normal and Diabetic Subjects," Diabetes, 1979, vol. 28, No. 1, pp. 71-81.

J. Stuart Soeldner, "Treatment of Diabetes Millitus by Devices," The American Journal of Medicine, Jan. 1981, vol. 70, 183-194.

Stuart J. Updike, et al., "Implanting the Glucose Enzyme Electrode: Problems, Progress, and Alternative Solutions," Diabetes Care, vol. 5, No. 3, May-Jun. 1982, pp. 207-212.

Kuykendall, V. G., et al., "Assessment of Self-Monitored Blood Glucose Results Using a Reflectance Meter with memory and Microcomputer," Symposium on Computer Applications in Medical Care, 9th: 1985:Baltimore, M.D., pp. 98-102.

Gifford-Jorgensen, R. A., et al., "Comparison of Five Glucose Meters for Self-Monitoring of Blood Glucose by Diabetic Patients," Diabetes Care, Jan.-Feb. 1986, vol. 9, No. 1, pp. 70-76.

Lawrence D. Devoe et al., "The Fetal Biophysical Profile: Antepartum Assessment Using a Programmed Microcomputer," Journal of Clinical Engineering, Jul.-Aug. 1986, vol. 11, No. 4, 285-289.

Chan, K. H., et al., "Microprocessor-Based Cardiopulmonary Rate Monitor," Medical & Biological Engineering & Computing, Jan. 1987, V. 25, No. 1, pp. 41-44.

Wiesspenier, G., et al, "Cardiotest=Single Chip Cardiac Monitor," Computer in Cardiology, Sep. 12-15, 1987: Leuven, Belgium (eds. Ripley, R.L.) pp. 463.

Christine A. Beebe, "Self Blood Glucose Monitoring: An Adjunct to Dietary and Insulin Management of the Patient with Diabetes," Journal of the American Dietetic Association, Jan. 1987, vol. 87, No. 1, pp. 61-65.

(56) References Cited

OTHER PUBLICATIONS

Zier, H., et al., "A Miniaturized, Portable Analyser for Operation of Glucose Sensors," GBF Monographs, 1987, vol. 10, pp. 261-262.
Subramanian,S., et al., "A Medical Device Data Acquisition System Using a Microcomputer-Based Software Interface," IEEE Engineering in Medicine and Biology Society 10.sup.th Annual International Conference, 1988, pp. 1432-1433.
"Central Fetal Monitoring Systems with Optical Disk Storage," Health Technology, 1988, vol. 2, pp. 249-251.
"Paying Attention to the 'Constants' in the Medical Care Equation," Health Technology, vol. 2, pp. 252-257.
Blood Glucose Monitors, Portable, Health Device, V. 17(9), 253-271 (1988).
Douglas, A.S., et al., "Hand-Held Glucose Monitor and Recorder," Proceedings of the Annual International Conference of the IEEE Engineering in Medicine and Biology Society, New Orleans, Nov. 4-7, 1988, pp. 747-748.
Stuart J. Updike, et al, "Laboratory Evaluation of New Reusable Blood Glucose Sensor," Diabetes Care, Nov./Dec. 1988, vol. 11, No. 10, pp. 801-807.
"Meters for Glucose Monitoring," The Medical letter on Drugs and Therapeutics, 1988, vol. 30, No. 778, pp. 101-102.
Beverly J. Leyerle, et al., "The PDMS as a Focal Point for Distributed Patient Data," International Journal of Clinical Monitoring and Computing, 1988, vol. 5, pp. 155-161.
"Blood Glucose Monitors," Health Devices, Sep. 1988, vol. 17, No. 9, pp. 253-271.
Daisuke Yoshizawa, et al., "The Development of a Data processing System with Personal Computer of MSX Standard System for Flow Injection Analysis," Journal of Flow Injection Analysis, 1988, V. 5, No. 2, pp. 101-110.
Zier, H., et al., "Portable Glucose Measurement in Blood," Artificial Organs, 1989, vol. 13, No. 2, pp. 176.
Zviran, M., et al., "DMSS—A Computer-Based Diabetes Monitoring System," Journal of Medical Systems, 1989, vol. 13, No. 5, pp. 293-308.
A.C. Thai, "Portable Meters for Self-Monitoring of Blood Glucose," Annals Academy of Medicine, Jul. 1989, vol. 18, No. 4, pp. 444-452.
A. Michael Albisser, "Intelligent Instrumentation in Diabetic Management," CRC CRitical Reviews in Biomedical Engineering, 1989, vol. 17, Issue 1, pp. 1-24.
"New Computer Uses Can Improve Diabetics' Lot," The Australian Journal of Pharmacy, Feb. 1989, vol. 70, pp. 144, 146-147.
J. Schrezenmeir, et al., "Computer Assisted Insulin Dosage Adjustment-Perspectives for Diabetes Control," Hormone and Metabolic Research, Supplement Series 1990, vol. No. 24, pp. 116-123.
Phillipou, G., et al., "Computer Based Quality Assessment of Hospital Capillary Blood Glucose Monnitoring," Diabetic Medicine, 1990, vol. 7, No. 3, pp. 234-237.
Cumbee, S. R., et al., "Cardiac Loop ECG Rcording: A New Noninvasive Diagnostic Test in Recurrent Syncope," Southern Medical Journal, 1990, vol. 83, No. 1, 39-43.
N. Ito, et al, "A Novel Blood Glucose Monitoring System Based on an ISFET Biosensor and its Application to a Human 75 g Oral Glucose Tolerance Test," Sensors and Actuators, B1, 1990, vol. 81(1-6) pp. 488-490.
E.F. Pfeiffer, "The Glucose Sensor: The Missing Link in Diabetes Therapy," Hormone and Metabolic Research, 1990, vol. 24, Suppl., pp. 154-164.
Laughton E. Miles, "A Portable Microcomputer for Long-Term Physiological Monitoring in the Home and Work Environment," Medical Monitoring in the Home and Work Environment, 1990, pp. 47-57.
Zamzow, K. et al., New Wearable Continuous Blood Glucose Monitor (BGM) and Artificial Pancreas (AP), Diabetes, 39:5A(20) (May 1990).
Carl E. Speicher, "The Bottom Line, Can Portable Blood Glucose Monitoring Improve the Outcomes of Diabetic Patients?," American Journal of Clinical Pathology, Feb. 1991, vol. 95, No. 2, pp. 112-116.
Kaj Lindecrantz, et al., "A System for Acquisition and Storage of Intra Partum Fetal ECG," Journal of Perinatal Medicine, vol. 19, Suppl. 1, pp. 342-345.
Kahn, M. G., et al., "Intelligent Computer-Based Interpretation and Graphical Presentation of Self-Monitored Blood Glucose and Insuling Data," Diab. Nutt Meta., 1991, vol. 4, Suppl. 1, pp. 99-107.
Latman, N. S., "Evaluation of Electronic, Digital Blood Glucose Monitors," Biomedical Instrumentation and Technology, 1991, vol. 25, No. 1, 43-49.
Reinauer, K. M., et al., "Evaluation of Systems for Computer-Assited Glucose-Reflectance Meters and Comparison of their Software," Diab. Nutr. Metab., 1991, vol. 4, Suppl. 1, pp. 109-115.
Dino A. Vallera, M.D., et al., "Accuracy of Portable Blood Glucose Monitoring, Effect of Glucose Level and Prandial State," Clinical Chemistry, A.J.C.P., Feb. 1991, pp. 247-252.
Schvarcz, E., et al., "Incidence of Symptomatic Mild Hypoglycemic Events: A Prospective Study in Adult Patients with Insulin-Treated Diabetes Mellitus Using a Portable Microcomputer-Based Data Logger," Diabetes Research, 1991, vol. 16, pp. 25-28.
M.F. Burritt, et al, "Portable Blood Glucose Meters: Teaching Patients How to Correctly Monitor Diabetes," Postgraduate Medicine, Mar. 1991, vol. 89, No. 4, pp. 75-78, 81, 84.
P.G. Fabietti, et al., "Wearable System for Acquisition, Processing and Storage of the Signal from Amperometric Glucose Sensors", International Journal of Artificial Organs, 1991, vol. 14, No. 3, pp. 175-178.
Raj Ajit K. Srivastava, "Effect of Glycosylation of Bacterial Amylase on Stability and active Site Conformation," Indian Journal of Biochemistry & Biophysics, Apr. 1991, vol. 28, No. 2, pp. 109-113.
Chen, C.Y. et al., "A Biocompatible Needle-Type Glucose Sensor Based on Platinum-Electroplated Carbon Electrode", Applied Biochemistry and Biotechnology, 36:211-226 (1992).
Andre J. Scheen, "Devices for the Treatment of Diabetes: Today," Artificial Organs, 1992, vol. 16, No. 2, pp. 13-166.
Charles L. Bryan, M.D., et al., "Ways to Improve Outcome After Cardiopulmonary Resuscitation, How to Monitor Patients, Correct Dysrhythmias," The Journal of Critical Illness, Aug. 1992, vol. 7, No. 8, pp. 1330-1347.
Thomas Hauser, et al., "Will Computers Replace or Complement the Diabetes Educator?," The Medical Journal of Australia, Oct. 5, 1992, vol. 157, 489-491.
Phillipou, G., et al., "Capillary Blood Glucose Measurements in Hospital Inpatients Using Portable Glucose Meters," Australian and new Zealand Journal of Medicine, 1993, vol. 23, No. 6, pp. 667-671.
Poitout, V., et al., "A Glucose Monitoring System for on Line Estimation in Man of Blood Glucose Concentration Using a Miniaturized Glucose Sensor Implanted in the Subcutaneous Tissue and a Wearable Control Unit," Diabetologia, 1993, vol. 36, No. 7, pp. 658-663.
Esch Hogen, et al., "Methods and Applications of Radio Identification" Tiidschirft van het Nederlands Electronica—en Radiogenootschap, 1993, vol. 58, No. 1, pp. 9-12.
V. L. Rose, et al., "Decentralized Testing for Prothrombin Time and Activated Partial Thromboplastin Time Using a Dry Chemistry Portable Analyser," Archives of Pathology and Laboratory Medicine, Jun. 1993, vol. 117, pp. 611-617.
Tsunenori Arai, et al., "A Portable Transcutaneous Blood Glucose Monitoring System Using Non-Invasive Collection of Suction Effusion Fluid From Skin," Proceedings of the 16.sup.th Annual International Conference of the IEEE Engineering in Medicine and Biology Socienty, Engineering Advances: New Opportunities for Biomedical Engineers, Jun. 1994, vol. 2, 812-813.
Hiroyuki Florio, et al., "Clinical Telecommunication Network System for Home Monitoring", Medical & Biological Engineering & Computing., Mar. 1994, vol. 32, 227-230.
Makikawa, M., et al., "Microprocessor-Based Memory Device for Ambulatory Heart Rate and Physical Activity Recording," Methods of Information in Medicine, 1994, vol. 33,, No. 1, pp. 94-96.

(56) References Cited

OTHER PUBLICATIONS

Marc C. Shults, et al., "A Telemetry-Instrumentation System for Monitoring Multiple Subcutaneously Implanted Glucose Sensors," IEEE Transactions on Biomedical Engineering, Oct. 1994, vol. 41, No. 10, pp. 937-942.
David Potter, "Fundametals of PC-Based Data Acquisition," SENSORS, Feb. 1994, pp. 12-20.
Skrabal, F., et al., "Portable System for On-Line Continuous Ex Vivo Monitoring of Subcutaneous Tissue Glucose Using Open Tissue Perfusion," Medical & Biological Engineering and Computing, Jan. 1995, vol. 33, No. 1, pp. 116-118.
James H. Nichols, et al., "Laboratory and Bedside Evaluation of Portable Glucose Meters," American Journal of Clinical Pathology, Feb. 1995, vol. 103, No. 2, pp. 244-251.
P. Kassirer, "The Next Transformation in the Delivery of Health Care," The New England Journal of Medicine, Jan. 5, 1995, vol. 332, No. 1, pp. 52-54.
V. Netz, Using Chip Cards to Promote Personal Health, Proceedings of the Health Cards '95 Conference, Oct. 1995, pp. 256-260.
K. Hara, "Application of Optical Memory Card for the Management of Maternity Care," Proceedings of the Health Cards '95 Conference, Oct. 1995, pp. 276-278.
R. Beyer, "Smart Cards, Technololgies and their Application," Proceedings of the Health Cards '95 Conference, Oct. 1995, pp. 145-149.
M. Michael Shabot, et al., "Real-Time-Wireless Decision Support Alerts on a Palmtop PDA," 19th Annual Symposium on Computer Applications in Medical Care. Toward Cost-Effective Clinical Computing, Oct.-Nov. 1995, pp. 174-177.
German language document: Sensor '95: "Neuheiten und Trends in der Sensorik," (Sensors '95: New Development and Trends in the Sensor Development, Sensors Report, May 1995, vol. 10, No. 3, pp. 14-18.
Michael E. Moseley, Ph.D., "MRI—Mapping the Human Brain Electronically", WESCON '95: Conference Record, San Francisco, CA, Nov. 7-9, 1995, pp. 656-659.
Table of Contents, Wescon '95: Conference Record, San Francisco, CA, Nov. 7-9, 1995.
Table of Contents of Health Cards '95 Conference, Oct. 23-26, 1995.
Cor J. Kalkman, "LabVIEW: A software System for Data Acquisition, Data Analysis, and Instrument Control," Journal of Clinical Monitoring, Jan. 1995, vol. 11, No. 1, pp. 51-58.
Eberhard Brunner, "An Ultra-low Noise Linear-in-DB Variable Gain Amplifier for Medical Ultrasound Applications," WESCON '95: Conference Record, San Francisco, CA, Nov. 7-9, 1995, pp. 650-655.
Willis G. Downing, Jr., "Electronic Measurements of Pulmonary Mechanics," WESCON '95: Conference Record, San Francisco, CA, Nov. 7-9, 1995, pp. 644-649.
Lisa E. Hake, "An Eye on the Future: Advances in Eye Care Technology," WESCON '95: Conference Record, San Francisco, CA, Nov. 7-9, 1995, pp. 638.
Stephen Harper, "Update on PCMCIA Standard Activities: CardBus and Beyond," WESCON '95: Conference Record, San Francisco, CA, Nov. 7-9, 1995, pp. 135-164.
V. Manfrini, et al., "Dual Concentric Conductor Arrays for Microwave Hyperthermia: Theoretical Study of Design Parameters," WESCON '95: Conference Record, San Francisco, CA, Nov. 7-9, 1995, pp. 661-684.
Charles Melear, "Configurable Modules of the MC68300 and MC68HC16 Microcontroller Families," WESCON '95: Conference Record, San Francisco, CA, Nov. 7-9, 1995, pp. 44-50.
G. Schlegelmilch, "Contributions of an IC-Manufacturer to Chip Card—Projects in Health Service Applications," Proceedings of the Health Cards '95 Conference, Oct. 1995, pp. 327-330.
A. F. Brockman, et al., "The Use of the Optical Memory Card to Facilitate Patient Centered Care During Pregnancy and to Provide a Basis for an Integrated Perinatal Data Collection System," Proceedings of the Health Cards '95 Conference, Oct. 1995, pp. 197-201.
K. Hirayama, et al., "Optical Memory Card—Present and Future State of the Technology and its Applications," Proceedings of the Health Cards '95 Conference, Oct. 1995, pp. 321-326.
P. Wenzlaff, et al., "DEFICARD: Health Card Project in Cardiology. Concept and One-Year-Report on Field Trial Experiences," Proceedings of the Health Cards '95 Conference, Oct. 1995, pp. 222-224.
H. Hrabcik, et al., Medical Functions on a Dynamically Multifunctional Personal Chip System (mPCS), Proceedings of the Health Cards '95 Conference, Oct. 1995, pp. 240-242.
M. Kossmann, "Experiences with the X-Ray Card," Proceedings of the Health Cards '95 Conference, Oct. 1995, pp. 243-245.
M. Opiela, "Multi-Functional Cards for Health Care Applications," Proceedings of the Health Cards '95 Conference, Oct. 1995, pp. 288-290.
K. Ozasa, et al., "Health Administration System Using an Optical Memory Card in a Rural Community," Proceedings of the Health Cards '95 Conference, Oct. 1995, pp. 279-283.
J. Berube, et al., "The Evaluation of the Rimouski Project: A Strategy for Development," Proceedings of the Health Cards '95 Conference, Oct. 1995, pp. 169-170.
John T. Oldenburg, "A Virtual Instrument Design Laboratory for Rapid Prototyping of Medical Instrumentation," WESCON 95: Conference Record, San Francisco, CA, Nov. 7-9, 1995, pp. 639-643.
Motorola Product Brief: MPC860ADS—Application Development System, 1995, pp. 4.
Motorola Product Brief MD68302 Family Application Development System, 1995, 4 pages.
Motorola Product Brief MPC821ADS—Application Development Sysytem, 1995, 4 pages, Rev. 1.1.
Report by Tom Balph, EC020/683XX Interface to ISA Bus-type PCMCIA Controller, 11 pages, Mar. 9, 1995.
Motorola MPC860 On-Chip Access Guide, MPC860 User's Manual, pp. 909-928.
Motorola MC68LC302 product Brief, Low Cost Intergrated Multiprotocol Processor, 1995, 6 pages.
A. M. Albisser, et al., "Diabetes Intervation in the Information Age," Medical Informatics, 1996, vol. 21, No. 4, pp. 297-316.
German Language Article: Aufgaben der Multisensorik, Design & Electronik vol. 39, No. 20, 1996, pp. 49.
Michael Greger, "PC-Cards die Vielfalt wachst" Electronik, Oct. 1996, vol. 45, No. 15, pp. 56-59.
C. Karen Altieri, "Introduction of a Fully Portable, Body-Mounted Emergency Medical Information System," Proceedings of the National Forum: Military Telemedicine On-Line Today Research, Practice, and Opportunities, 1996, pp. 135-140.
Rolf Engelbrecht, et al., "DIABCARD—A Smart Card for Patients with Chronic Diseases," Clinical Performance and Quality Healthcare, Apr./May/Jun. 1997, No. 5, vol. 2, pp. 67-70.
S. F. Kurikov, et al., "Use of a Sigma-Delta Analog-to-Digital Converter in Multichannel Electrocardiographs," Biomedical Engineering, 1997, vol. 31, No. 4, pp. 190-194.
Steven M. George, "NTIS: Computer Aided Medical Assistant (CAMA) System," NTIS: Report No. ARO-36050.1-MA-STI, Mar. 11, 1997, pp. 1-24.
MC68PM302 Device Errata, Revision C Changes, Feb. 27, 1997, 2 pages. Motorola Introduction to EBX, Version 1.8, Apr. 2, 1997, 2 pages.
A. Pizzuti, et al., "Valutazione di una scheda per la registrazione e l'archiviazione di electtrocardiogrammi con personal computer non dedicato," Minerva Cardioangiologia, V. 45, No. 7-8, 1997, pp. 357-361; English Abstract included: Evaluation of an Electrocardiographic Card to be directly Inserted into a Standard Personal Computer.
User's Guide, Accu-Chek Compass Diabetes Care Software, Roche Diagnostics, pp. 1-93 (2000).
Internet printout: MC68302 Product Summary Page, printed Nov. 8, 2002, www.motorola.com, 6 pages.

(56) References Cited

OTHER PUBLICATIONS

Motorola Report on Science, Standards and Stewardship, Wireless Safety Update, Sep. 2002, 11 pages.
Internet printout: Motorola Announces Latest Developer's Kits for Its Pagewriter 2000 Two-Way Pager, Pagewriter 2000X Two-Way Wireless Communications Center and Creatalink 2XT Two-Way Data Transceiver, www.motorola.com, 2 pages.
Internet printout: MC68356: Signal Processing Communication Engine (SPCE), www.motorola.com, printed Nov. 8, 2002, 2 pages.
PCMCIA Release 2.0 Interface Board for Dragonball Update, www.motorola.com, Nov. 24, 1998, 5 pages.
Internet printout: A Complete Control and Monitoring Solution—Motorola's Creatalink 2 XT Two-Way Data Transceiver Can Provide Wireless Communications Between Devices and People, www.motorola.com, printed Nov. 8, 2002, 2 pages.
Internet printout: QRS Products, Software Integration, Office Medic IDMS, Spirometry, Press Release, (QRS Diagnostic Secures International Approvals on key Patent; Sunrise Lifestyle Centers Selects QRS Medical Devices; QRS and CompleWare Integrate Software and Medical Devices to Streamline Data Collection and Management for Clinical Trials; Physicians Worldwide Can Now Use Advanced patient Information management Software and Medical Devices from QRS Diagnostic; QRS Releases Office Medic Small Office Edition Software), QRS Diagnostic, printed Oct. 31, 2002, 17 pages.
Internet printout: Voyager Pulse Oximeter, www.dolphinmedical.com, Oct. 31, 2002, 3 pages.
Internet printout: Accu-Chek Pocket Compass, 6 pages.
Internet printout: Accu-Chek Compass, Accu-Chek Pocket Compass, www.accu-chek.com, printed on Oct. 12, 2002, 17 pages.
Internet printout: How Flash Memory Works, CompactFlash, by Jeff Tyson, www.howstuffworks.com, printed on Sep. 28, 2002, 2 pages.
Internet printout: How Flash Memory Works, SmartMedia, by Jeff Tyson, www.howstuffworks.com, printed on Sep. 28, 2002, 2 pages.
Internet printout: How Flash Memory Works, Gadget of the Day, by Marshall Brain, www.howstuffworks.com, printed on Sep. 28, 2002, 2 pages.
Internet printout: Fingerprint ID, Biometric Logon, Data Access Protection and Fingerprint ID, www.motorola.com and www.guardwaresystems.com, 16 pages, printed on Nov. 8, 2002.
Smale et al., (IEE Colloquium on Intelligent Instrumentation, p. 5-7, May 13, 1991).

* cited by examiner

BLOOD GLUCOSE TRACKING APPARATUS AND METHODS

This application is a divisional patent application of U.S. patent application Ser. No. 10/112,671, filed Mar. 29, 2002, now U.S. Pat. No. 7,041,468, which claims the benefit of priority to U.S. provisional patent applications No. 60/300,011, filed Jun. 20, 2001, and 60/280,905, filed Apr. 2, 2001, which are assigned to the same assignee as the present application and are hereby incorporated by reference.

BACKGROUND OF THE INVENTION

1. Filed of the Invention

The invention relates to blood glucose monitoring, and particularly to a blood glucose monitor and data management and display device integrated as a synchronous, hand-held unit, as an effective and efficient diabetes management tool.

2. Discussion of the Related Art

Blood glucose self-measurements have been conventionally taken by diabetics. The diabetic uses a blood glucose measuring tool. The diabetic typically pricks his or her finger using a lancet. A droplet of exposed blood is applied to a sensor strip which is placed in the glucose measuring tool. A reading appears on a display of the measuring tool indicating the blood glucose level of the diabetic.

Diabetics sometimes use a computer having some form of software that permits the user to track the glucose measurements they have taken. The glucose measurements are typically loaded into the computer manually by the diabetic. Other transfer methods are possible that require steps by the diabetic in order that the information gets entered into the computer, e.g., transferring glucose readings that have been retained in memory of the measuring tool via a cable to the computer. The data may be sent to a health care professional who may also be keeping an eye on the diabetic's status. It is an object of this invention to provide a more efficient and reliable process of taking the measurement, determining the glucose level, entering the glucose level data into a diabetes management program, and managing the diabetes condition using diabetes management software.

In the past, the glucose measurement tool could be carried by the patient for use almost anywhere. However, access to data entry and management using the computer and software have been relegated to a PC setup at a fixed location such as the patient's home, and so these steps had to wait until the diabetic arrived back at his or her home. In the present invention, it is recognized that the development of hand-held devices such as PDAs and mobile phones and PDA/mobile phone combined units could permit diabetics to enter data and use the data management software away from their PCs. It is therefore an object of this invention to provide a system that permits data entry and management by the diabetic away from the diabetic's PC. In addition, it is desired to have a device that permits this mobile data entry and management, and yet permits the user to take off-finger measurements, or using so-called alternate site testing.

Conventional methods have utilized two very separate instruments, the glucose measurement tool and the PC. It is an object of this invention to provide a synchronous tool that performs the conventional functions of both the glucose measurement tool and PC, and perhaps additional features and advantages. It is a further object to synergistically provide this tool, such as by using a same power source and/or a same display for both purposes, i.e., glucose measurement and data management and/or analysis.

SUMMARY OF THE INVENTION

In view of the above, and in particular accordance with the above objects, a measurement module for glucose testing is provided including a glucose testing measurement module housing, a test strip receptacle formed in the housing, and a connector portion formed in the housing and shaped to permit mechanical, removable attachment of the housing to a hand-held processing device, hand-held computer, PDA, mobile phone or wireless processing device. Electronics are provided either in the measurement module or in the hand-held processing device for determining the amount of glucose present in a sample of body fluid, when a test strip is positioned in the receptacle and the fluid is placed on the test strip, and for communicating the glucose amount to the processing device via the connector portion.

The test strip is typically inserted into the test strip receptacle so that the system may calibrate in preparation for application of the body fluid to the strip. Insertion of the strip may further initiate an activation of electrical components that participate in the testing of a body fluid sample. When the system is ready after connecting the measurement module with the hand-held processing device, and after insertion of the strip into the receptacle in the measurement module, and after any calibration or component activation, then the system display preferably indicates that the body fluid is to be now applied to the strip for testing. An alternative system may be or may become available to those skilled in the art wherein the body fluid is applied to the strip, and/or calibration/component activation occur, before strip insertion, and if such system would otherwise include one or more features of preferred embodiments herein, then such systems may also be within the scope of a preferred embodiment.

The housing of the glucose testing measurement module is configured so that a sample of body fluid may be easily applied to the strip when the module is connected to the hand-held processing device and the strip is inserted into the receptacle in the measurement module. The end of the housing from which the strip protrudes is substantially narrowed compared with the end that connects with the hand-held processing device. This narrowed end is preferably a tapered trapezoidal profile, is preferably rounded in two or three directions, protrudes from the connector end defining a shoulder or inset particularly for matching an alternate site body contour and is preferably made of low durometer material, so that the module can rest comfortably and securely on a body location near the test site for easy and precise application of the body fluid to the strip. This configuration of the housing is particularly advantageous when off-finger or alternate site testing is desired such as at an arm or a leg site.

The test strip may be side-filled and may also be tip-filled. Use of a side-filled strip is particularly advantageous for alternate site testing. For example, the module may be rested near the alternate test site (for example a forearm) with a user contacting a rounded shoulder of the housing on the user's skin. The device is then rocked comfortably into a test strip side-fill contact position with the body fluid, due to the ergonometric and/or arthopometric design of the module. For this purpose the module preferably has no square or sharp edges exposed when fitted with the handheld processing device. Even when using a tip-filled strip, exposed edges of the module are preferably rounded for rocking the strip into tip-filled contact with the body fluid, even though the depth of the module is small compared with its width particularly at the wider connection end, and contact with the user may be established perhaps only at a single point on the narrowed end when the body fluid in applied to the strip. The test strip advantageously uses only a relatively small amount of body fluid sample for performing reliable tests, such as less than 1 microliter. Measurements are conducted preferably using a coulometric technique, and alternatively an amperometric, reflectrometic or other technique understood by those skilled in the art, which is significant for alternate site testing wherein typically a lower volume of sample is made available by a same lancing operation at an alternate site than when testing is performed on the finger.

The removable connectability of the measurement module with the hand-held processing device is greatly facilitated by electronics that integrate the two components of this integrated system. An isolation barrier is provided for safe glucose monitoring and/or analysis, even though power is preferably supplied to the module from the hand-held processing device, while also data is transferred between the measurement module and hand-held processing device. The power is preferably transformer-coupled, or alternatively capacitatively-coupled, between the isolated and non-isolated sides of the barrier. Analog front-end signal acquisition circuitry of the measurement module allows signals including data indicative of a blood glucose level or other test of the body fluid to be acquired by the measurement module. Opto-isolators preferably isolate data I/O circuitry and provide a data signal transport route across the barrier to the hand-held processing device so that the data can be analyzed there and/or easily uploaded to a PC by HotSync. By "HotSync", what is meant is any method of synchronizing data in the handheld with data in a PC, such as by cable, cradle, infrared or radio link. By "analyze", it is meant that the hand-held processing device can do more than merely display a glucose measurement value. For example, charts, plots and graphs of compiled glucose data can be generated and additional factors such as diet, exercise, insulin regimen, etc., may be used to process and/or display various information relating to a diabetic condition or regimen. Serial to parallel conversion circuitry permits parallel access to a data/address bus of the hand-held processing device to the data transported across the barrier.

In a particular embodiment, a measurement module for glucose testing is further provided including a test strip receptacle in a glucose measurement module, a connector portion formed in the module shaped to permit connection of the module to a hand-held computer by inserting the connector portion of the glucose measurement module into a receptacle defined within the hand-held computer, and electronics for determining the amount of glucose present in a sample of body fluid, when the fluid is placed on a test strip and the test strip is positioned in the receptacle, and for communicating the glucose amount to the hand-held computer via the connector portion.

A glucose monitoring apparatus is further provided including a measurement module configured to couple with a test sensor and a hand-held processing device electrically and mechanically coupled with the measurement module to form an integrated, hand-held unit for performing and analyzing a glucose measurement after the test sensor is coupled with the measurement module and body fluid is applied to the test sensor.

A further glucose monitoring apparatus is provided including a measurement module configured to couple with a test sensor and a hand-held processing device electrically and mechanically coupled with and separable from the measurement module to form an integrated, hand-held unit for performing and analyzing a glucose measurement after the test sensor is coupled with the measurement module and body fluid is applied to the test sensor.

A glucose monitoring apparatus is also provided including a measurement module configured to couple with a test sensor and a hand-held processing device configured to receive data transmission from the measurement module. The measurement module and processing device form a synchronous unit for performing and analyzing a glucose measurement after the test sensor is coupled with the measurement module and body fluid is applied to the test sensor. The monitoring apparatus includes a single display at the processing device.

A glucose monitoring apparatus is further provided including a measurement module not having a display for displaying results of glucose measurements, the module being configured to couple with a test sensor, and a hand-held processing device configured to receive data transmission from the measurement module. The measurement module and the processing device form a synchronous unit for performing and analyzing a glucose measurement after the test sensor is coupled with the measurement module and body fluid is applied to the test sensor. The processing device includes a display for displaying the results of said glucose measurements.

A glucose monitoring apparatus is further provided including a measurement module configured to couple with a test sensor and a hand-held processing device configured to receive a data transmission from the measurement module. The measurement module and processing device form a synchronous unit for performing and analyzing a glucose measurement. The processing device is configured for automatically receiving the data transmission after the test sensor is coupled with the measurement module and body fluid is applied to the test sensor.

A method of performing a glucose measurement using a measurement module and a hand-held processing device is provided including coupling the processing device electrically and mechanically with the measurement module to form an integrated, hand-held unit for performing and analyzing a glucose measurement after a test sensor is inserted into the measurement module, coupling the test sensor with the measurement module, applying body fluid to the test sensor and reading a glucose level from a display on the integrated hand-held unit.

A method of performing a glucose measurement using a measurement module and a hand-held processing device is also provided including coupling the processing device with the measurement module to receive a data transmission from the measurement module such that the measurement module and the processing device form a synchronous unit including a single display on the processing device for performing and analyzing a glucose measurement after a test sensor is inserted into the measurement module, coupling the test sensor with the measurement module, applying body fluid to the test sensor and reading a body fluid glucose level from the display on the processing device.

A method of performing a glucose measurement using a measurement module and a hand-held processing device, is further provided including inserting the measurement module into a receptacle defined within the processing device for the processing device to receive a data transmission from the measurement module, such that the measurement module and the processing device form an integrated, hand-held unit for performing and analyzing a glucose measurement after a test sensor is inserted into the measurement module, coupling the test sensor with the measurement module, applying body fluid to the test sensor and reading a glucose level from a display on the processing device.

The invention further includes a method of performing a glucose measurement using a measurement module and a hand-held processing device including coupling the processing device with the measurement module to automatically receive a data transmission from the measurement module after a test sensor is inserted into the measurement module, such that the measurement module and the processing device form a synchronous unit for performing and analyzing a glucose measurement, coupling the test sensor with the measurement module, applying body fluid to the test sensor and reading a glucose level from a display.

A glucose monitoring apparatus is further provided including a measurement module configured to couple with a test sensor, and a hand-held processing device electrically and mechanically coupled with the measurement module to form an integrated, hand-held unit for performing and analyzing a glucose measurement after the test sensor is inserted and body fluid is applied to the test sensor. The measurement module is further geometrically configured to enable off-finger or alternate site application of blood to the test strip.

A glucose monitoring apparatus is also provided including a measurement module configured to couple with a test sensor, and a hand-held processing device electrically and mechanically coupled with the measurement module to form an integrated, hand-held unit for performing and analyzing a glucose measurement after the test sensor is inserted and body fluid is applied to the test sensor. The measurement module is rounded in three dimensions for providing smooth off-finger or alternate site points of contact with the skin of a person being tested.

A glucose monitoring apparatus is further provided including a measurement module configured to couple with a test sensor, and a hand-held processing device electrically and mechanically coupled with the measurement module to form an integrated, hand-held unit for performing and analyzing a glucose measurement after the test sensor is inserted and body fluid is applied to the test sensor. The measurement module is rounded in at least two dimensions for providing smooth off-finger or alternate site points of contact with the skin of a person being tested.

A glucose monitoring apparatus is also provided including a measurement module configured to couple with a test sensor, and a hand-held processing device electrically and mechanically coupled with the measurement module to form an integrated, hand-held unit for performing and analyzing a glucose measurement after the test sensor is inserted and body fluid is applied to the test sensor. The measurement module includes a telescoping trapezoidal profile for permitting placement of a test strip inserted within the module at an off-finger or alternate site location of a person being tested.

A glucose monitoring apparatus is also provided including a measurement module configured to couple with a test sensor, and a hand-held processing device electrically and mechanically coupled with the measurement module to form an integrated, hand-held unit for performing and analyzing a glucose measurement after the test sensor is inserted and body fluid is applied to the test sensor. The measurement module includes an encapsulation port for the test sensor and a PC board including an opto-isolation component. The measurement module extends less than two inches in length and less than one half inch in thickness beyond dimensions of the wireless processing device.

A software program for analyzing glucose data measured with a glucose monitoring apparatus which includes a measurement module configured to couple with a test sensor and a hand-held processing device is further provided. The measurement module and processing device form a synchronous unit for performing and analyzing a glucose measurement after the test sensor is inserted and body fluid is applied to the test sensor. The processing device is configured to HotSync with a PC. The software program includes instructions for a processor to perform the steps of creating a replica database on the PC of the glucose data stored in a device database on the processing device, and synchronizing the glucose data to a PC database program. The synchronizing step includes reading the glucose data stored in the device database on the processing device, matching the data to corresponding data in the replica database, format converting the data and writing the data to the replica database.

A software program for analyzing glucose data measured with a glucose monitoring apparatus which includes a measurement module configured to couple with a test strip and a hand-held processing device is also provided. The measurement module and processing device form a synchronous unit for performing and analyzing a glucose measurement after the test strip is inserted and body fluid is applied to the test strip. The processing device is configured to HotSync with a PC. The software program includes instructions for a processor to perform the steps of measuring glucose data from the test strip having body fluid applied thereto, automatically downloading the glucose data from the measurement module to the processing device, and downloading the glucose data to a personal computer.

A method for analyzing glucose data measured with a glucose monitoring apparatus which includes a measurement module configured to couple with a test sensor and a hand-held processing device. The measurement module and processing device form a synchronous unit for performing and analyzing a glucose measurement after the test sensor is inserted and body fluid is applied to the test sensor. The processing device is configured to HotSync with a PC. The method includes creating a replica database on the PC of the glucose data stored in a device database on the processing device, and synchronizing the glucose data to a PC database program. The synchronizing step includes reading the glucose data stored in the device database on the processing device, matching the data to corresponding data in the replica database, format converting the data, and writing the data to the replica database.

A method for analyzing glucose data measured with a glucose monitoring apparatus which includes a measurement module configured to couple with a test strip and a hand-held processing device is also provided. The measurement module and processing device form a detachably integrated, hand-held unit for performing and analyzing a glucose measurement after the test strip is inserted and body fluid is applied to the test strip. The processing device configured to HotSync with a PC. The method includes measuring glucose data from the test strip having body fluid applied thereto, automatically downloading the glucose data from the measurement module to the processing device after measuring said glucose data, and downloading the glucose data to a personal computer.

A software program for analyzing glucose data measured with a glucose monitoring apparatus which includes a measurement module configured to couple with a test sensor and a hand-held processing device is further provided. The measurement module and processing device form a synchronous unit for performing and analyzing a glucose measurement after the test sensor is inserted and body fluid is applied to the test sensor. The software program includes instructions for a processor to perform the steps of measuring glucose data, providing a sensory output of a glucose level corresponding to the data, and automatically entering the data into a database accessible by a diabetes management software program.

A method for analyzing glucose data measured with a glucose monitoring apparatus which includes a measurement module configured to couple with a test sensor and a hand-held processing device. The measurement module and processing device form a detachably integrated, hand-held unit for performing and analyzing a glucose measurement after the test sensor is inserted and body fluid is applied to the test sensor. The method includes measuring glucose data, providing a sensory output of a glucose level corresponding to the data, and automatically entering the data into a database accessible by a diabetes management software program.

BRIEF DESCRIPTION OF THE DRAWINGS

FIG. 6b schematically shows a rear view of the glucose module of FIG. 6a.

FIG. 6c schematically shows a bottom perspective view of the glucose module of FIG. 6a.

FIG. 6d schematically shows a top perspective view of the glucose module of FIG. 6a.

FIG. 6e schematically shows a side view of the glucose module of FIG. 6a.

FIG. 6f schematically shows a front view of the glucose module of FIG. 6a.

FIG. 7b schematically shows a plan view of the integrated measurement module and PDA of FIG. 7a.

INCORPORATION BY REFERENCE

Figure 1:
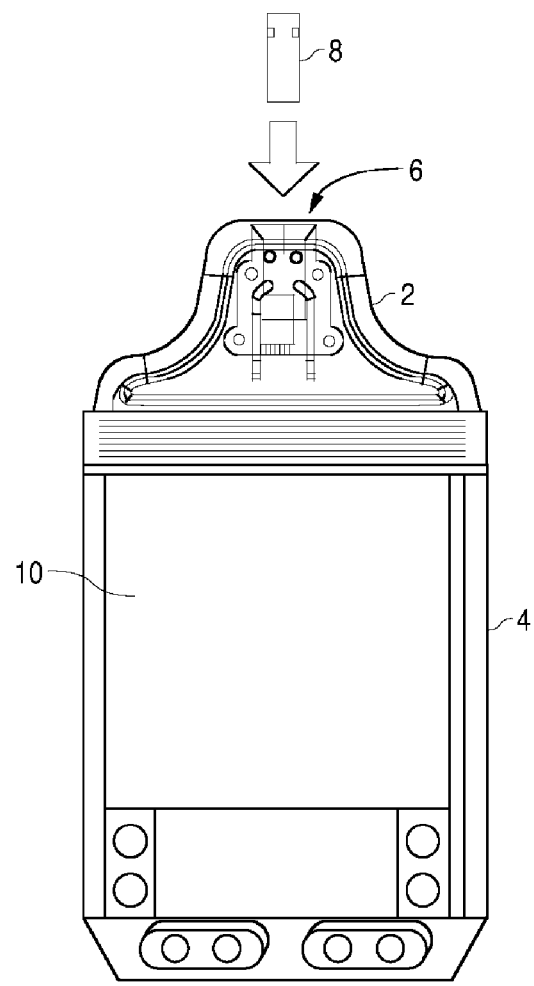
FIG. 1 schematically shows a plan view of an integrated glucose measurement module and hand-held processing device, such as a personal digital assistant or PDA, or mobile phone, integrated phone and PDA, or other wireless device, according to a preferred embodiment.

What follows is a cite list of references each of which is, in addition to the background, the invention summary, the abstract and the claims, hereby incorporated by reference into the detailed description of the preferred embodiments below, as disclosing alternative embodiments of elements or features of the preferred embodiments not otherwise set forth in detail below. A single one or a combination of two or more of these references may be consulted to obtain a variation of the preferred embodiments described in the detailed description below. Further patent, patent application and non-patent references are cited in the written description and are also incorporated by reference into the preferred embodiment with the same effect as just described with respect to the following references:

U.S. patent application Ser. Nos. 09/413,565, 60/300,011 and 60/280,905, which are assigned to the same assignee as the present application;

Published U.S. application Ser. Nos. 2002029058, 2002025469, 2002008038, 2001054319, and 2001017269, which are also assigned to the same assignee as the present application;

U.S. Pat. Nos. 5,307,263, 5,601,435, 5,899,855, 5,974,124, 6,153,062, 6,330,426, 6,334,778, D427,312, D439,242, D426,638, D424,696 6,338,790, 6,329,161, D450,854, 6,299,757, 6,294,281, 6,281,006, 6,251,260, 6,175,752, 6,120,676, 6,103,033; and GB 1579690, GB 2225637, GB 2194892, GB 2073891, GB 2154003, and GB 2204408; and EP 0504835, EP 0799896, EP 0800082, EP 0880936, EP 0048090, EP 0078636, EP 0096288, EP 0125139, EP 0136362, EP 0170375, EP 0080304, EP 0184909, EP 0206218, EP 0230472, EP 0241309, EP 0245073, EP 0278647, EP 0286084, EP 0359831, EP 0368209, EP 0390390, EP 0400918, EP 0453283, EP 0470290, EP 0255291, EP 0127958, EP 0781406 and EP 1147739 A2; and PCT applications No. WO 86/00513, WO 89/02246, WO 90/00367, WO 95/06240, WO 96/07907, WO 96/07908, WO 96/07893, WO 97/20207, WO 97/41421, WO 97/46868, WO 98/09167, WO 98/24366, WO 98/52045, WO 99/05966, WO 99/32883, WO 99/467582, WO 00/13580, WO 00/20626, WO 00/33065, WO 00/78210, WO 01/24038, WO 01/52727, WO 01/33216, WO 01/57238, WO 01/57239, WO 01/67009, WO 85/05119, WO 89/08713, WO 90/05300, WO 91/04704, WO 92/13271, WO 94/20602, WO 94/27140, WO 95/02817, WO 97/00441, WO 97/18464, WO 97/19344, WO 97/42882, WO 97/42883, WO 97/42886, WO 97/42888, WO 97/43962, WO 99/08106, WO 01/88524, WO 01/36430, WO 01/36660, WO 00/78992 and WO 99/30152; and Schrezenmeir, et al., Computer Assisted Insulin Dosage Adjustment-Perspectives for Diabetes Control, Hormone and metabolic Research, Supplement Series Vol. No. 24, pp. 116-123 Theme Medical Publishers (1990);

A. Michael Albisser, Intelligent Instrumentation in Diabetic Management, Vol. 17, Issue 1, pp. 1-24 (1989);

J. Stuart Soeldner, Treatment of Diabetes Millitus by Devices, the American Journal of Medicine, Vol. 70, 183-194 (January 1981);

New Computer Uses Can Improve Diabetics' Lot, The American Journal of Pharmacy, Vol. 70, pp. 144, 146 (February 1989);

Hiroyuki Horio, Clinical Telecommunication Network System for Home Monitoring, Med. & Biol. Eng. & Comput., 32, 227-230 (March 1994);

A. S. Douglas et al., Hand-Held Glucose Monitor and Recorder, Proceedings of the Annual International Conference of the IEEE Engineering in Medicine and Biology Society, New Orleans, 747-748 (Nov. 4-7, 1988);

User's Guide, Accu-Chek Compass Diabetes Care Software, Roche Diagnostics, pp. 1-93 (2000);

Laughton E. Miles, A Portable Microcomputer for Long-Term Physiological Monitoring in the Home and Work Environment, pp. 47-57, Raven Press, eds. Laughton E. Miles and Roger J. Broughton (1990);

P. G. Fabietti et al., Wearable System for Acquisition, Processing and Storage of the Signal from Amperometric Glucose Sensors, International Journal of Artificial Organs, Vol. 14, No. 3, pp. 175-178 (1991);

Heller, A., "Amperometric biosensors based on three-dimensional hydrogel-forming epoxy networks," Sensors and Actuators B, 13-14:180-183 (1993);

Heller, A., "Electrical Connection of Enzyme Redox Centers to Electrodes," J. Phys. Chem, 96(9):3579-3587 (1992); and Heller, A., "Electrical Wiring of Redox Enzymes," Acc. Chem. Res., 23(5):129-134 (1990).

DETAILED DESCRIPTION OF THE PREFERRED EMBODIMENTS

FIG. 1 schematically shows a perspective view of an integrated glucose measurement module 2 and a hand-held processing device 4, such as preferably a personal digital assistant (PDA) 4 or a mobile phone or combined PDA/phone or other wireless device with a processor as may be understood by those skilled in the art. Hereinafter when the term PDA is used it is meant to refer to any of these or other hand-held processing devices, any of which may also be operated using hands-free accessories and/or equipment. The glucose measurement module 2 (hereinafter "module 2") is shown in FIG. 1 mechanically attached to the PDA 4. The module 2 is in this way physically mounted to and integrated with the PDA 4. The module 2 is also electrically connected to the PDA 4 when mounted into the PDA 4. In addition, the module 2 is software interfaced with the PDA 4 when mounted into the PDA 4. The module 2 shown in FIG. 1 preferably does not have a display, since the display of the PDA 4 may be used for displaying information. The PDA 4 may be replaced by another processing device having a display such as a mobile phone having a connector for attaching the module 2.

The module is shown having a slot 6 for insertion of an in vitro test strip 8. Some details may be found at U.S. patent application Ser. No. 09/413,565, which is assigned to the same assignee as the present application and is hereby incorporated by reference. When the test strip 8 is inserted into the slot 6, preferably blood such as whole blood, plasma and/or serum, and alternatively another body fluid such as interstitial fluid, sweat, urine, tears, saliva, dermal fluid, spinal fluid, etc., is applied to the strip 8 and the module 2 measures the glucose level of the body fluid applied to the strip 8. Hereinafter, whenever blood or body fluid is referred to for being applied to the strip 8, it is meant to include whatever body and/or biological fluid that may be applied to strip 8 for testing. The glucose level data automatically transfers to the PDA 4 (the data transfer mechanism is described in more detail below with reference to FIGS. 2-5), and the glucose level in the blood tested is displayed on the display 10 of the PDA 4, or transmitted through a speaker or otherwise to a user of the device shown in FIG. 1.

The PDA 4 is configured to HotSync with a PC for transmitting data to a PC. The PDA 4 may also transmit data by wireless RF and/or IR connection to a remote or host client or server computer. The PDA 4 also preferably has internet connectability or is otherwise configured for logging into a network for transmitting and receiving data from the network.

Figure 2:
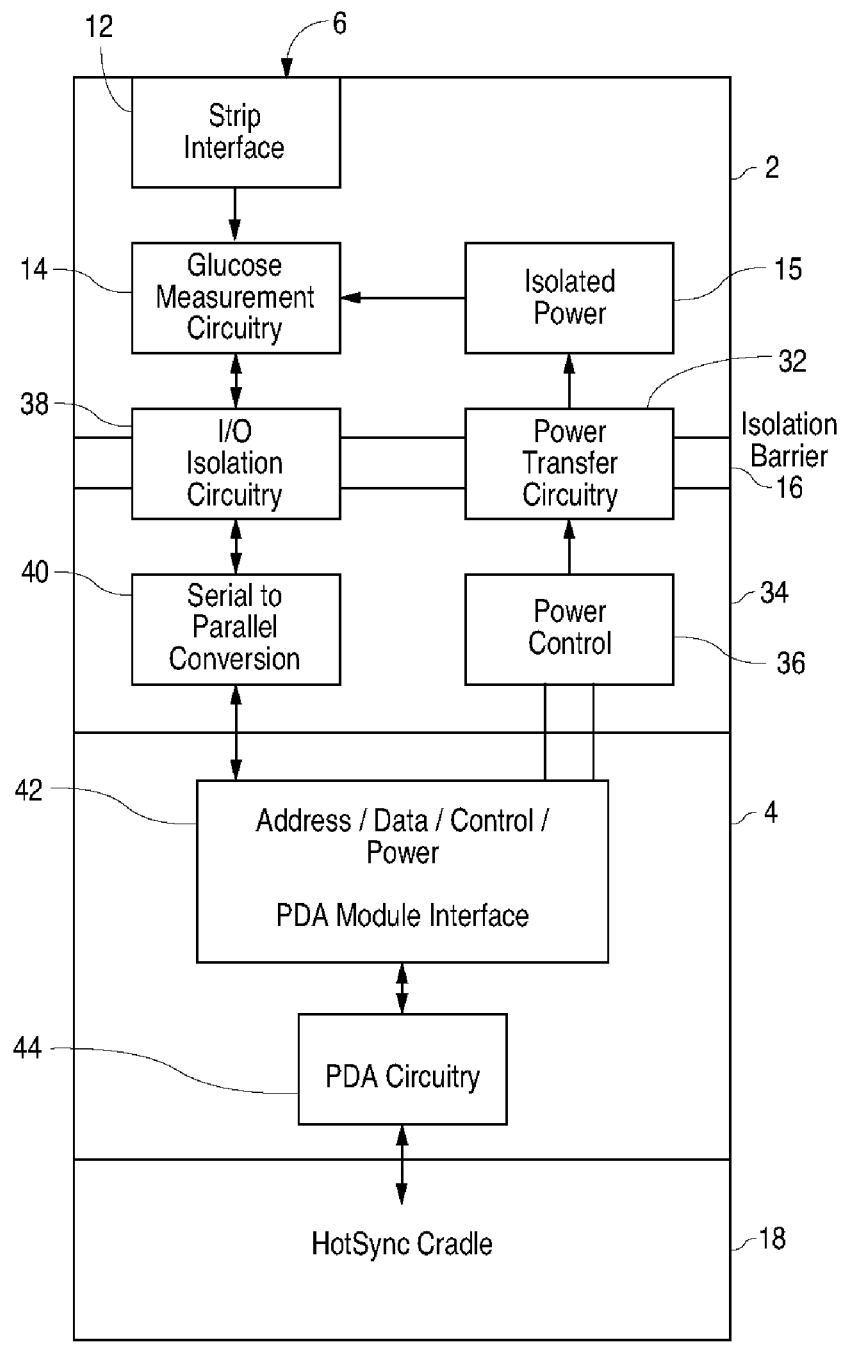
FIG. 2 shows a block diagram of electrical modules of the integrated glucose measurement module and PDA of FIG. 1.

FIG. 2 shows a block diagram of electrical modules of the integrated glucose measurement module 2 and PDA 4 of FIG. 1. At the point of the in vitro test strip slot 6 at the top of FIG. 2 is a strip interface 12 including circuitry for connecting to an in vitro test strip for passing a current through blood applied to the strip. Glucose measurement circuitry 14 is shown connected to the strip interface 12 for measuring one or more parameters indicative of a blood glucose level of the blood applied to the strip. An isolated power module 15 provides power to the glucose measurement circuitry 14 and strip interface 12 and ultimately to the test strip.

An isolation barrier 16 is shown for isolating the power at the module from the power at the PDA 4. The isolation barrier 16 is provided to protect the user from having a high current pass through his or her body when the PDA 4 is in a HotSync cradle 18 and thus is connected to AC power. Since an electrically conductive part of the integrated measurement module 2/PDA 4 system (i.e., a strip) contacts the patient, the system may be considered to have a "patient applied part" and would be bound to comply with applicable standards (AAMI ES1, IEC60601-1-2, etc) for isolated patient connections. These standards contain requirements for a maximum amount of current that can flow in either direction between the patient and an AC power line or ground with either the module 2 or the patient in contact with 110% of line voltage.

When the glucose measurement module 2 is inserted into the PDA 4 and the PDA 4 is connected to it's HotSync cradle 18 as shown in FIG. 2, AC ground is connected to the module 2. This connection is made because the ground connection of the HotSync cradle 18 to the PDA 4 is connected to ground at the computer to which the HotSync cradle is connected, which is in turn connected to earth ground at the AC outlet. If AC voltage is applied to the strip connector 12, a large amount of current would flow to AC ground through the module 2, PDA 4, HotSync 18, and/or computer circuitry.

Figure 3A:
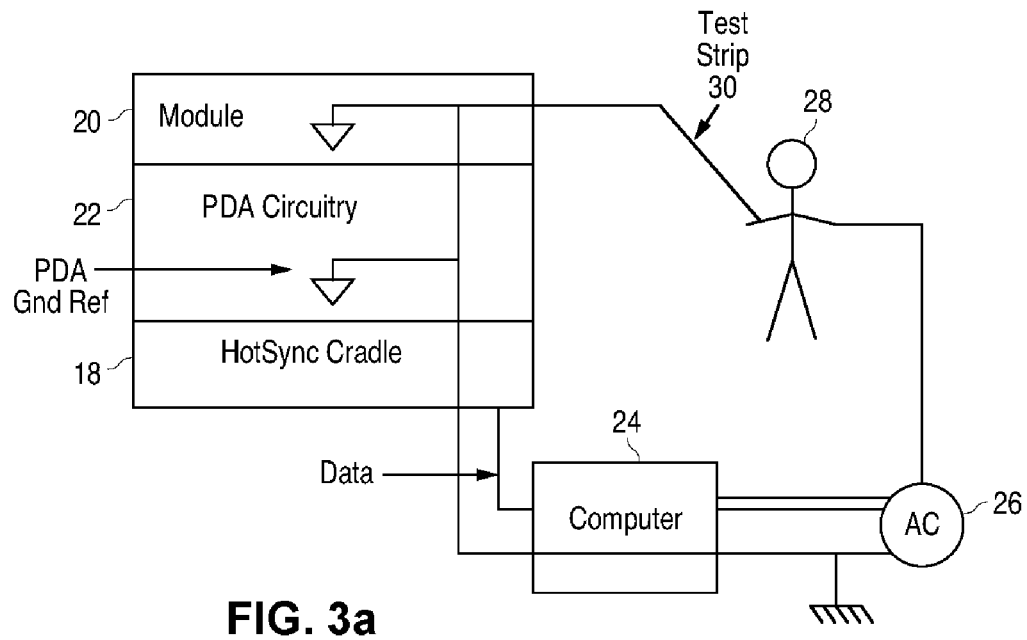
FIGS. 3a and 3b schematically illustrate an advantageous electrical isolation barrier feature of an integrated module and PDA according to a preferred embodiment.

Referring to FIG. 3a, a module 20 connected to PDA circuitry 22 and not having the electrical isolation barrier 16 of FIG. 2 is illustrated. A patient 28 is shown contacting a test strip 30, e.g., for applying blood to the strip or for inserting the strip into the module 20. The patient 28 is also contacting AC power 26 which also powers a computer 24. The computer 24 is shown communicating with the PDA 22 through the HotSync cradle 18. AC ground is shown connected to the computer 24, the Hotsync cradle 18, the PDA circuitry 22, and the module 20. If the user 28 became in contact with the test strip 30 and inadvertently came in contact with any earth referenced potential, large currents would flow through the user 28, and back to earth ground via this path. Conversely, if the module 20 or test strip 30 were to be inadvertently raised to a high potential reference to earth ground, again large currents would flow through the user 28. The risk in each case is electrocution of the user 28 and the standards consider having the user 28 in contact with significant potentials a viable scenario. Should even very small currents flow across the heart, e.g., there is significant risk of causing fibrillation.

Figure 3B:
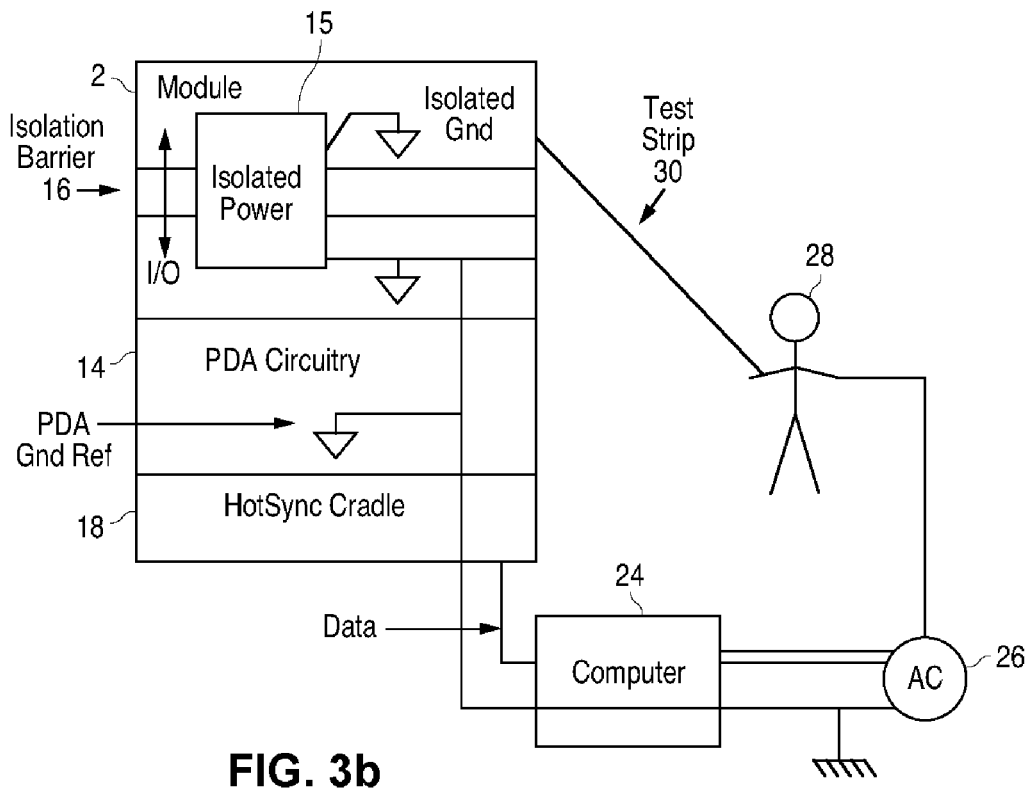

In order to prevent this potentially dangerous situation, electrical connections which come into contact with the user 28 at the strip connector 30 are advantageously isolated from earth ground or AC in accord with a preferred embodiment. FIG. 3b illustrates the scenario described above with respect to FIG. 3a except that the module 2 includes the isolation barrier 16 referred to above with reference to FIG. 2. The user 28 who is shown in FIG. 3b in contact with AC power 26 to the computer 24 is also contacting the strip 30 which is connected to the module 2. In contrast with the scenario illustrated by FIG. 3a, the strip 30 is not connected to AC ground, and thus no currents pass through the user 28.

This isolation barrier 16 is preferably created via a physical or otherwise insulating gap in the circuitry on the PC board or the module 20. A preferred dimension of this gap is around 4 mm and is generally dictated by electrical safety standards.

Referring back now to FIG. 2, the glucose measurement circuitry 14 and strip interface 12 are shown on the isolated side of the barrier 16. Power for this isolated circuitry is created by power transfer circuitry 32, which is a transformer coupled, switching power supply according to a preferred embodiment. The transformer 32 bridges the isolation barrier 16 and transfers isolated power 15 to the isolated side of the barrier 16 from the PDA-to-module interface connector 34. For sufficiently low power consumption requirements, a capacitively-coupled supply would be a viable alternative power transfer circuitry 15. Switching control circuitry 36 is on the PDA (ground referenced) side of the isolation barrier 16.

A glucose value is calculated by circuitry 14 on the isolated side of the barrier 16. The glucose value, status, and errors are communicated across the isolation barrier 16 preferably via a bidirectional serial interface 38. Control commands may be preferably received from the PDA 4 via this same interface 38. Serial communication lines of the serial interface 38 bridge the isolation barrier 16 preferably via optoisolators (not shown, but see FIG. 5 and discussion below). Serial information is converted to parallel by serial to parallel conversion circuitry 40 within the module 2 on the PDA side of the barrier 16, so that the module 2 can communicate with the PDA 4. The PDA interface 42 at the module connector 34 is parallel access directly to a PDA data/address bus of PDA circuitry 44. This interface 42 includes control lines as well as power connections.

As an alternative to providing an electrical isolation barrier between module 2 and PDA 4, features can be incorporated into module 2 that prevent it from being used at the same time that PDA 4 is connected to a HotSync cradle or cable, thereby eliminating the risk of passing high levels of electric current through the cradle or cable to or from the patient. This can be accomplished by providing an extended portion of the housing of module 2 that extends down along PDA 4 to interfere with the attachment of a cradle and/or cable to PDA 4 when module 2 is first attached thereto, or prevent the attachment of module 2 when a cradle or cable is already attached to PDA 4.

Figure 4:
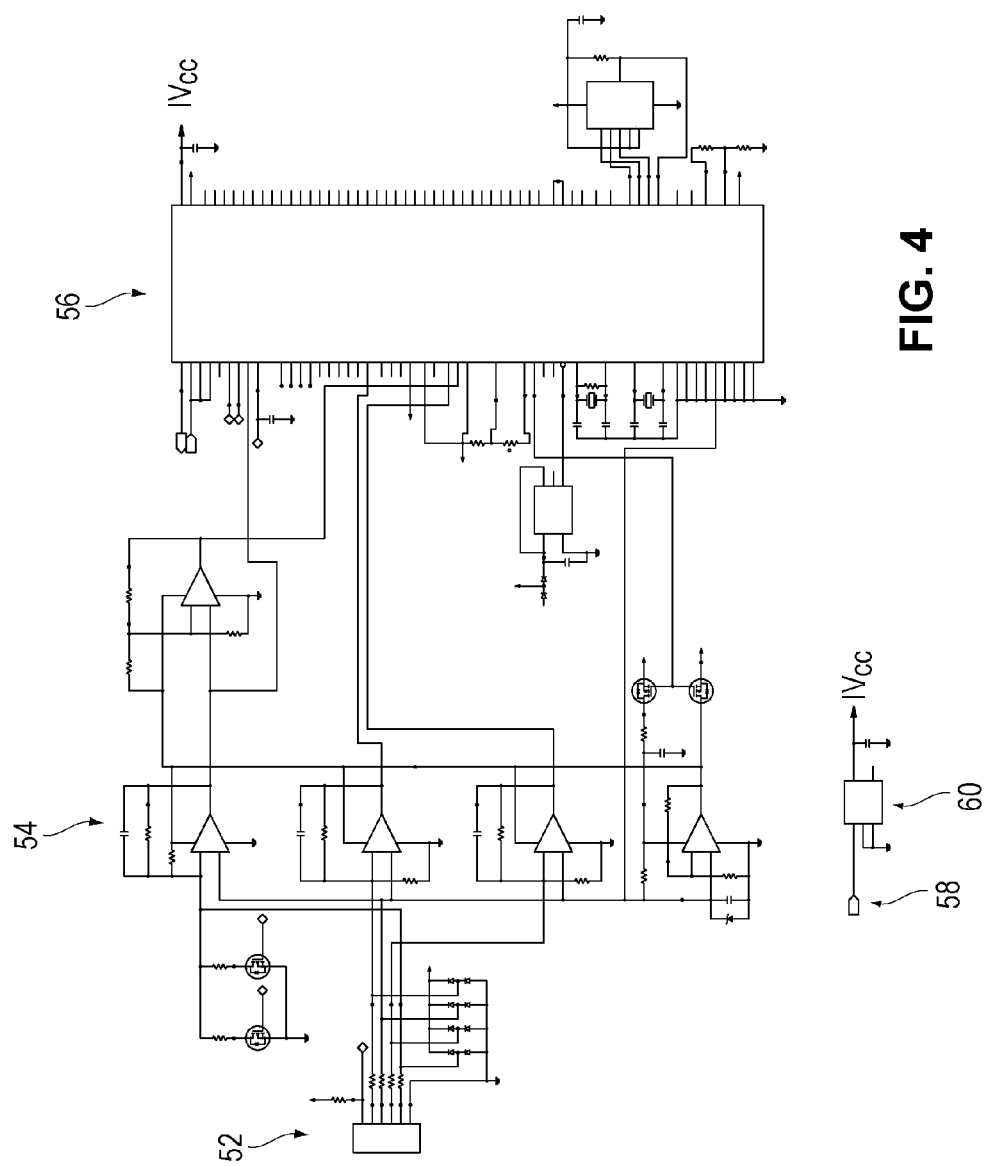
FIG. 4 shows an electrical circuitry schematic of a glucose measurement module for integrating with a PDA according to a preferred embodiment.

FIG. 4 shows an electrical circuitry schematic of a glucose measurement module for integrating with a PDA according to a preferred embodiment. The electrical schematic shown in FIG. 4 shows a strip connector 52 for making electrical connection to a strip 8 inserted into the slot 6 of the module 2 of FIG. 1. Analog front end signal acquisition circuitry 54 is shown for acquiring signals indicative of a blood glucose level in blood applied to the strip 8 (FIG. 1). A microprocessor 56 is shown for controlling the module 4. The microprocessor 56 receives isolated power (see element 15 of FIG. 2) as isolated voltage IVcc from an unregulated voltage at point 58 of the schematic of FIG. 4 appearing on the isolated side of the barrier (which is the barrier 16 of FIG. 2), and regulated through regulator 60.

Figure 5:
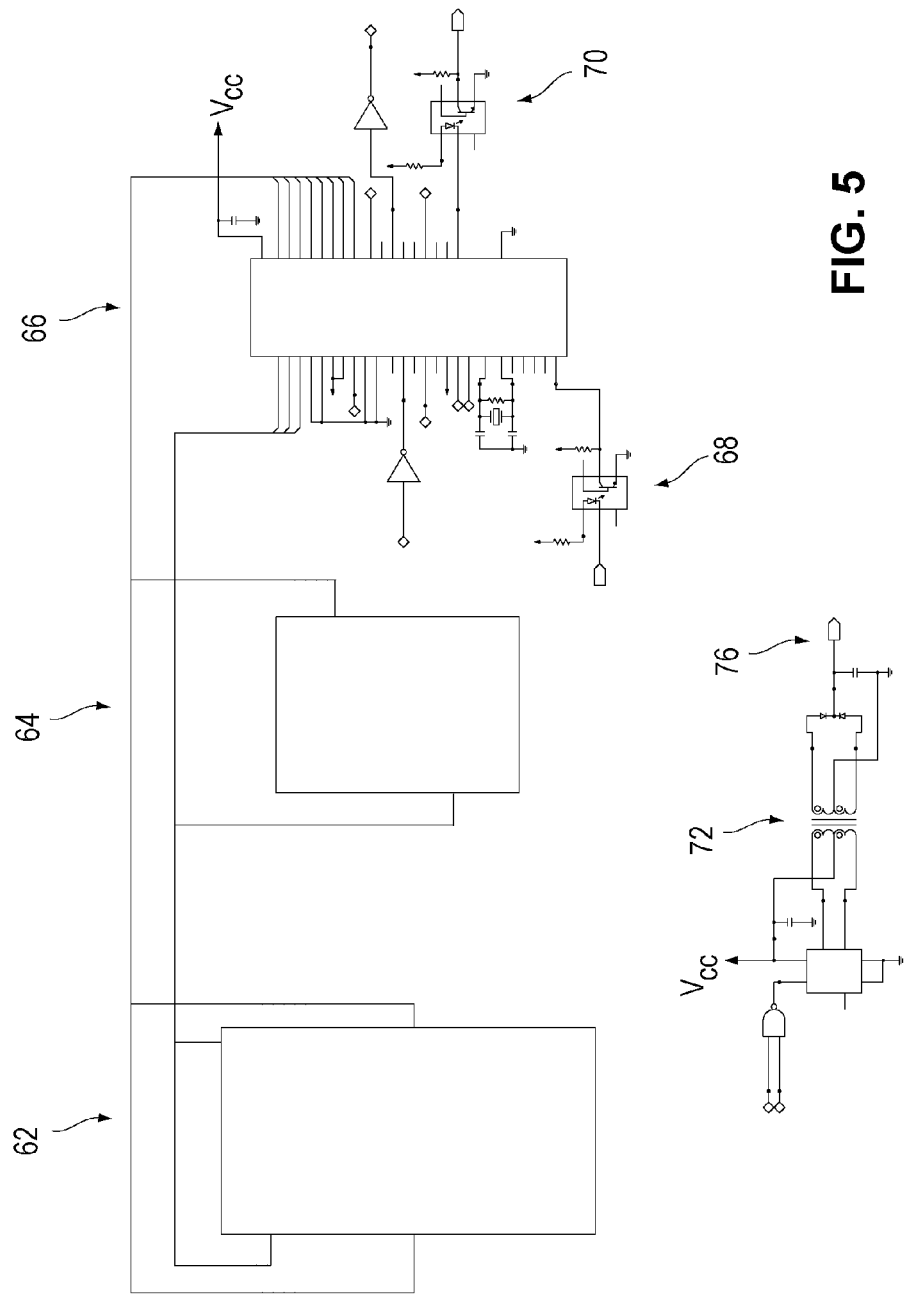
FIG. 5 shows an electrical circuitry schematic of a PDA for integrating with a glucose measurement module according to a preferred embodiment.

FIG. 5 shows an electrical circuitry schematic of a PDA for integrating with a glucose measurement module according to a preferred embodiment. A connector 62 for mounting the module 2 with the PDA 4 as shown in FIG. 1 is shown next to a memory 64 for storing digital data. At the right in FIG. 5 is a universal asynchronous receiver/transmitter or UART 66. The UART is on the non-isolated side of the barrier 16 of FIG. 2. The UARTs perform the serial to parallel conversion of element 40 of FIG. 2.

Data is transmitted serially from the glucose module 2 to the UART 66 (or converter 40 of the module 2 of FIG. 2) through optoisolator 68. Data is transmitted serially from the UART 66 to the isolated side of the barrier 16 of FIG. 2 through the optoisolator 70. Data may alternatively be transferred across the barrier 16 in parallel. Additional optoisolator components would be used for parallel data transfer compared with serial transfer. Serial transfer is preferred and allows the module 2 to be smaller, more economical to manufacture and more power efficient than if parallel transfer and additional optoisolators are used.

Power is transferred from the PDA 4 through the transformer (corresponding to the power transfer circuitry 32 of FIG. 2). The transformer is preferably a 1:1 transformer, and may be a step-down or step-up transformer of a desired ratio. Through the transformer, power as voltage Vcc is transferred from the non-isolated side of the barrier 16 to the isolated side as isolated power 76. The power may be around 3.3 Volts according to a preferred embodiment.

Figure 6A:
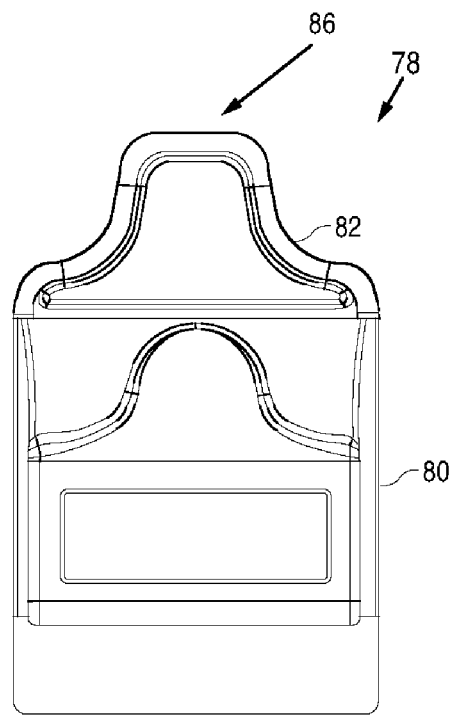
FIG. 6a schematically shows a bottom plan view of a glucose measurement module for integrating with a PDA according to a preferred embodiment.

FIG. 6a schematically shows a plan view of a glucose measurement module 78 for integrating with a PDA (not shown, but see FIGS. 7a-7b) according to a preferred embodiment. The module 78 includes a mounting portion 80 and a specially shaped extension portion 82. When the module 78 is inserted into a PDA and is mechanically and electrically attached to the PDA and configured to transfer data to/from the PDA, the mounting portion 80 is within the PDA and the extension portion 82 protrudes outside of the PDA.

The module 78 (corresponding to the module 2 of FIG. 2) is about 54 mm wide at the mounting portion 80 which plugs into the PDA 4 and scales down to around 23 mm at the end 86 of the extension portion 82 where the strip 8 of FIG. 1 is inserted. The extension portion 82 itself measures about 54 mm in width at the other end where the mounting portion 80 begins and the extension portion 82 is preferably about 28 mm long from the mounting portion 80 to the strip insertion end 86. The shoulder from which the extension portion 82 narrows most drastically in about 8.5 mm in extent o the approximately 28 mm extent of the extension portion 82. The curvature from the shoulder is about 0.5 rho, which changes direction at a curvature of about 0.5 rho and which changes direction again at a curvature of about 0.6 rho to the strip insertion end 86. As the shoulder flattens out, it makes an angle of about 100° with the elongated direction of the module 78 from the strip end 86, or 80° looking at it from the direction of the mounting portion 80, which angle can be varied somewhat while maintaining the shoulder and also the smoothness of the rounding of the extension portion 82. The extension portion 82 is shown symmetric, but may have an arbitrary curvature on one side the module 78 will be used by resting the extension portion on only the side with rounded features as just described, i.e., it is preferred there are no sharp corners on at least one side of the extension portion 82, and it is more particularly preferred that no sharp corners exist anywhere on the extension portion 82, nor even on the mounting portion 80.

Figure 6B:
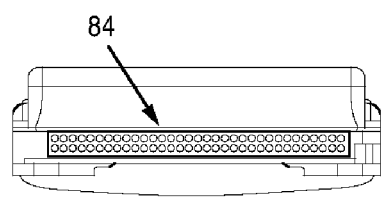

The mounting portion 80 connects electrically and for data transfer to the PDA by preferably a 68 pin electrical connector 84 as shown in FIG. 6b for connecting to a complementary 68 pin male connector of the PDA, wherein the male and female configuration may be reversed or mixed. The thickness of the module 78 is indicated as preferably around 19 mm. FIG. 6b schematically shows a rear view of the glucose module of FIG. 6a. Although not shown, the module 78 attaches mechanically in place in the PDA receptacle by a pair of mechanical latches preferably on opposing sides, e.g., the left and right side in FIG. 6a, of the PDA receptacle.

The extension portion 82 is particularly ergonometrically and/or arthopometrically configured so that a patient may insert a strip into a strip insertion slot (corresponding to slot 6 of FIG. 1) at the end 86 of the extension portion 82, and so that the patient can contact the strip with a drop of blood on the skin of the patient's body. The device is configured so that the patient may choose to use his or her arm, leg or any convenient anatomic location including the finger. This is advantageous because conventional systems often require application of blood to the strip at the finger.

A feature of the shape of the extension portion 82 is its protruding and/or telescoping trapezoidal profile. A utility design is provided at the extension portion 82 of the module 78 that promotes easy and efficient manipulation of the glucose strip on the blood drop whether if be on or off-finger or at an alternate site. The PDA module design incorporates a telescoping trapezoidal profile that allows ease of placement and inhibits the PDA body from encroaching or otherwise interfering with the placement, e.g., at a patient's arm. At the same time, the design is unobtrusive, streamlined and safe.

The telescopic and/or protruding trapezoidal profile of the module includes generous radii on each of the compound edges shown in FIG. 6a. The design allows easy and effective collection of a blood sample from any approved site on the body. The design allows for ease of positioning the module in the proximity of the blood drop and when actually placing the glucose strip on the blood drop. The preferred radii of curvature of each of the three bends on each side of the slot 86 of the extension portion 82 of FIG. 6a are drawn to scale. The curvatures are selected such that the PDA does not interfere with the blood application to the strip, e.g., from a patient's arm, leg or other approved off-finger location, and such that the shoulders of the extension portion 82 of the module 78 may rest gently on the patient's arm while the blood is applied, if the patient chooses, e.g., for support and/or stability. In addition, the design allows for a discreet and unobtrusive profile extending from the PDA. The design is compact and portable and preferably does not include cumbersome and potentially hazardous cables and extra attachments.

Figure 6C:
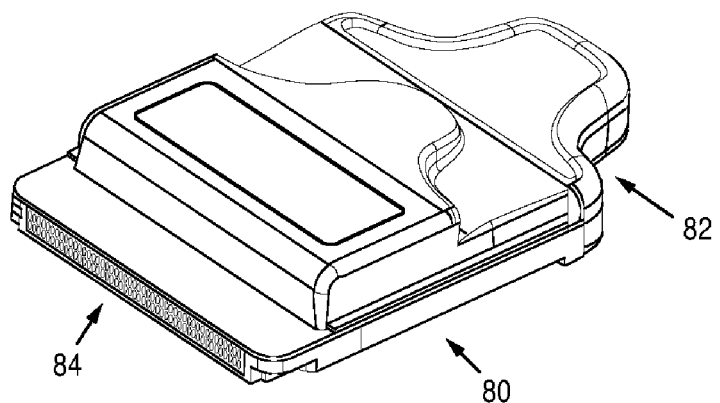
Figure 6D:
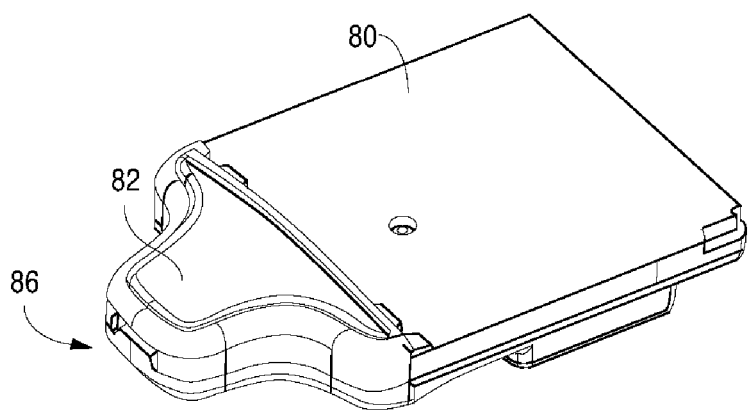
Figure 6E:
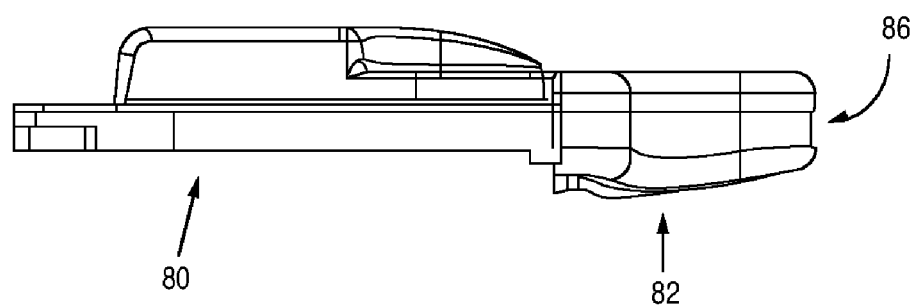
Figure 6F:
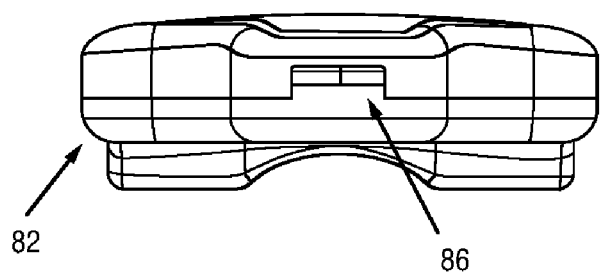

The extension 82 is preferably rounded in three dimensions or at least two dimensions, e.g., as illustrated by the various views of the preferred embodiment shown in FIGS. 6c-6f, and as mentioned, preferably has no sharp corners on at least one side which may be rested upon an arm or leg near an alternate site testing location, and for displaying information while testing on each arm for different tests such as on different days, the extension 82 is preferably rounded on both side and is particularly preferably symmetric as shown. FIG. 6c schematically shows a bottom perspective view of the glucose module 78 of FIG. 6a with extension portion 82, mounting portion 80 and pin connector 84. FIG. 6d schematically shows a top perspective view of the glucose module 78 of FIG. 6a with mounting portion 80, extension portion 82 and strip insertion end 86. FIG. 6e schematically shows a side view of the glucose module 78 of FIG. 6a, indicating a total length of about 85 mm, a thickness of about 14 mm at the extension portion 82 and a thickness of about 0.9 mm at the mounting portion 80, wherein the extension portion 82 and mounting portion 80 couple in a staggered fashion with each portion 80 and 82 having an edge which looks out somewhat over the other. FIG. 6f schematically shows a front view of the glucose module of FIG. 6a with the strip insertion portion 86 showing at the end of the extension portion 82. The corners are rounded with radius of curvature about 2.6 mm in the middle of the curve.

Figure 6G:
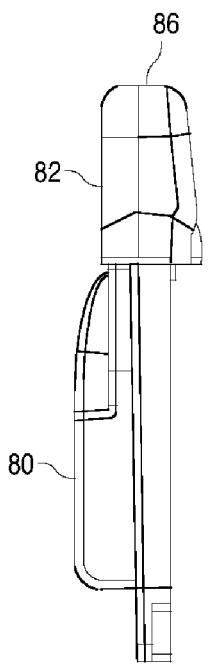
FIG. 6g schematically shows another side view of the preferred glucose module with preferred dimensions shown in millimeters.
Figure 6H:
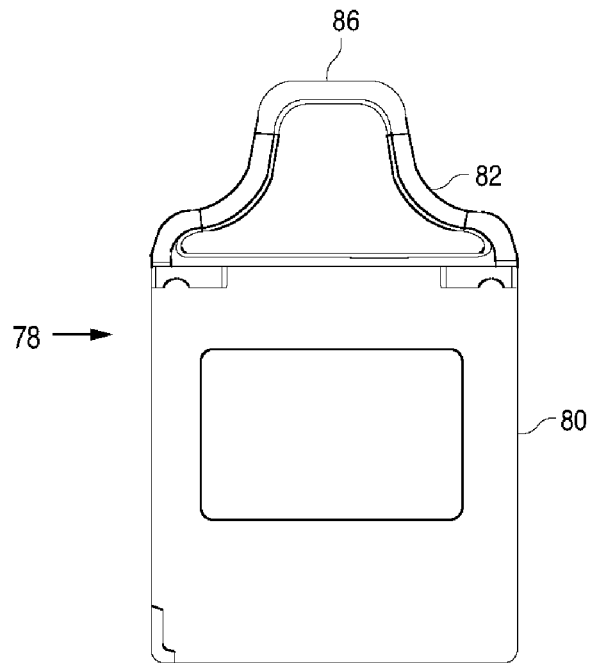
FIG. 6h schematically shows a top view of the preferred glucose module with preferred dimensions shown in millimeters.
Figure 6I:
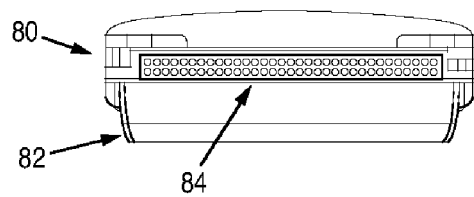
FIG. 6i schematically shows another rear view of the preferred glucose module with preferred dimensions shown in millimeters.

FIGS. 6g, 6h and 6i schematically show another side view, a top view and another rear view of the preferred glucose module with preferred dimensions shown in millimeters. Referring to FIG. 6g, the mounting portion 80 of the module 78 has a thickness of around 14.3 mm, which differs from the 0.9 mm thickness shown at FIG. 6e. The thickness, as well as the width and/or length, of the mounting portion 82 is preferably set to adapt to the dimensions of the receptacle of the hand-held processing device (e.g., PDA, mobile phone, combined PDA/phone, etc.) that the module 78 is to be connected, and these dimensions will vary depending on the device, and so no fixed numeric dimensions are necessarily universally preferred. The rounding of the strip insertion end 86 of the extension portion 82 is shown as having minimum radii of curvature of 9 mm on the bottom side and 2.5 mm on the top side. Referring to FIG. 6h, the rounding from the shoulder of the extension portion has a minimum radius of curvature around 12 mm, while the rounding which is opposite in direction as the rounding from the shoulder has a curvature radius of about 33 mm and that final rounding near the strip insertion end 86 is about 22 mm at minimum. Referring to FIG. 6i, a thickness of around 19.5 mm is shown for the rear view, which shows the pin connector 84, including the thickness of the mounting portion 80 added with the staggered overlooking portion of the extension portion 82, as briefly described above, i.e., so that the staggered overlook portion of the extension portion 82 is about 5 mm.

As shown in FIGS. 6a-6i, the extension portion 82 is rounded away from each side of the slot 86 in two orthogonal directions, and rounds from the slot 86 toward the mounting portion 80, corresponding to a third direction in which the extension portion 82 of the module 78 is rounded. This advantageous design prevents potential hazards such as pinching, lacerations, cuts or skin abrasions, during normal use and handling.

The module 78 serves as a housing for the strip connector, PC board and the opto-isolation components, while not appearing bulky or obtrusive. As mentioned above, the module 78 does not include a display such as a LCD screen because the PDA display may be used as an advantageous PDA accessory for displaying blood glucose levels without delay due to the integrated design of the module 78 with the PDA (see FIG. 1). This contributes to the compactness feature of the design, enabling the module 78 to entend less than two inches beyond the end of the PDA, and as shown in FIG. 6a, less than 1.5 inches and even below 1.2 inches. The module 78 at the extension portion 82 is around or less than 0.25 inches thicker than the PDA. The module 78 weighs less than two ounces and the preferred embodiment shown is around 1.1 ounces, while the design may be configured at less than one ounce. In contrast, if a display such as an LCD were included in the module 78, the module 78 would likely be 50-60% longer, 0.25 inches thicker and be at least two ounces. The preferred module 78 thus does not have a display, and is thus smaller and lighter than if it did have a display, while the integrated module-PDA system has full display capability. Obtaining power to run module 78 from the PDA rather than from an internal power source also contributes to the light, compact arrangement shown.

The module 78 shown and described with respect to FIGS. 6a and 6b including the telescoped, trapezoidal-shaped design has fully-radiused shoulders in an advantageous profile. Some preferred radii and compound angle values are shown in FIG. 6a. From the slot 86, the design rounds toward the PDA at a preferred radius of curvature of 0.6 rho, then rounds in the opposite direction away from the slot 86 at a preferred 0.5 rho and then reverses its curvature again toward the PDA at a preferred 0.5 rho.

The module 78 advantageously mates with a PDA device and forms a single, hand-held unit for glucose measuring and data management. The mechanical design shown in FIGS. 6a-6f allows measurements to be taken that suppress problems that might otherwise present themselves such as interference by the bulky PDA in the blood application process, improper strip placement and positioning, potential for injury, and obtrusiveness. The glucose monitoring strip may be positioned to apply the blood drop, while being attached to the module 78 which is itself mounted into the PDA. The sheer size of the PDA in relation to the module 78 does not inhibit the application process due to the design of the extension portion 82 such that the PDA body does not interfere with or become a hindrance to placement. The shape the profile of the module actually conforms to the shape of a body part such as an arm to which it rested, without presenting itself with an "arm-sliding" problem, as the user positions the module 78 in close proximity to the blood drop. The rounded shape, generous radii and material selection reduce potential hazards to the user, in terms of cuts, lacerations or skin abrasions.

Alternative designs would provide for a more pointed profile to the module 78 to presumably provide easier access to the glucose strip or the module 78 may be alternatively connected through a strip connector and a flexible cable to allow flexibility of placement, independent of the PDA body. These alternative designs are not preferred, however, as the size of the pointed profile may be limited by the size of the strip connector and would likely not allow the user to effectively position the strip due to a lack of plastic real estate. Additionally, a flexible cable, although affording flexibility of placement, would be cumbersome and visibly obtrusive. The preferred design thus has the slightly wider tip such as shown in FIG. 6a and no cumbersome cable is used in the preferred embodiment which includes the module 78 directly mechanically coupled with the PDA.

The module 78 and particularly the extension portion 82 are made of a low durometer material or thermoplastic elastomer facepad detail on both sides of the enclosure, to act as a gripping surface for module insertion and extraction, as well as afford the module a measure of shock absorption. The material may preferably be a PC-ABS alloy or other non-filled plastic resin.

Figure 7A:
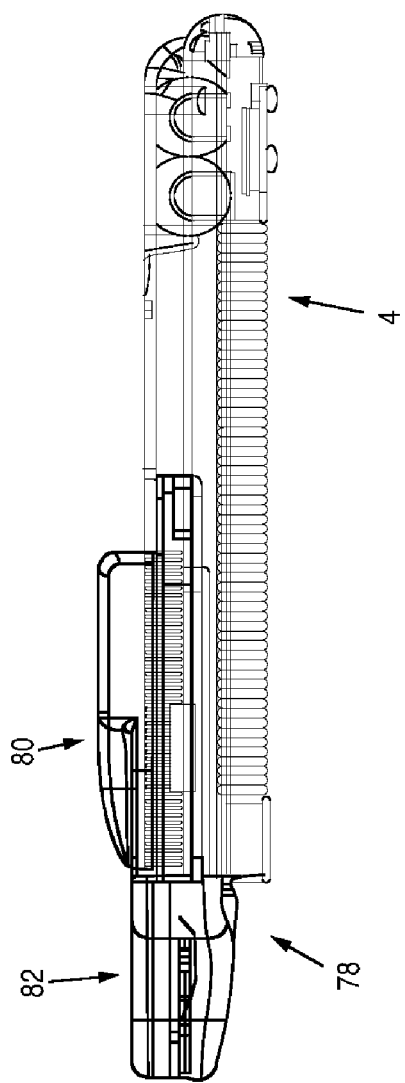
FIG. 7a schematically shows a side view of the measurement module of FIG. 6a integrated with a PDA according to a preferred embodiment.
Figure 7B:
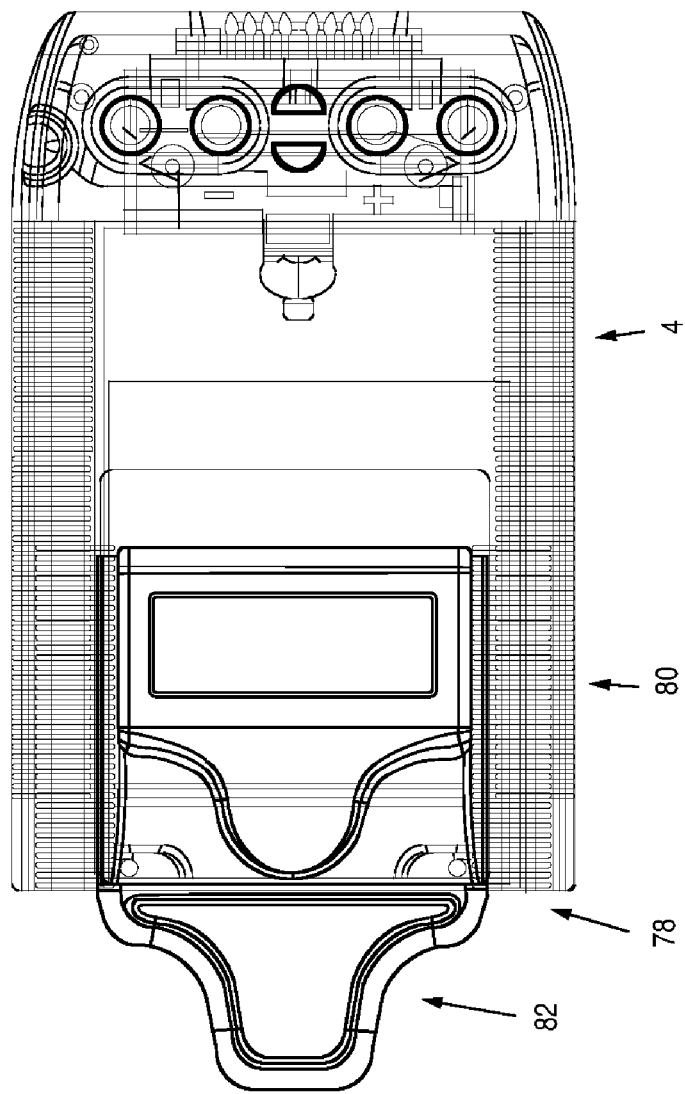

FIG. 7a schematically shows a side view of the measurement module 78 of FIG. 6a integrated with a PDA 4 according to a preferred embodiment. An indication of an staggered overlook portion of the extension portion 82 being 6.25 mm as opposed to the 5 mm shown about, again indicates that the dimensions of the module 78 can be varied to meet the specifications of the particular hand-held device 4 being used. The mounting portion 80 is shown inserted into the PDA 4 while the extension portion 82 is shown protruding from the PDA 4. FIG. 7b schematically shows a plan view of the integrated measurement module 78, with mounting portion 80 and extension portion 82, and PDA 4 of FIG. 7a. As shown, the extension portion 82, with length of about 28 mm, protrudes from the PDA 4 while the mounting portion 80 of the glucose measurement module 78, with overall length of about 73 mm, is inserted within the receptacle of the PDA 4 (or other hand-held processing device, see above).

Figure 8:
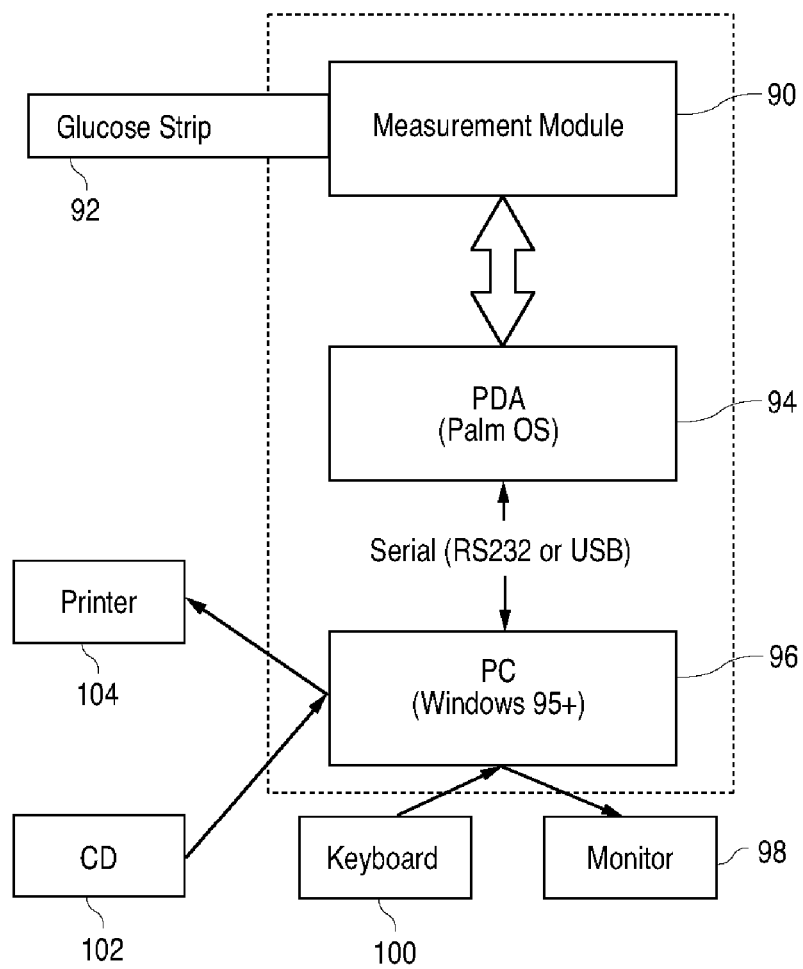
FIG. 8 illustrates a glucose data handling system software according to a preferred embodiment in block diagram form.

FIG. 8 illustrates generally a glucose data handling system software according to a preferred embodiment in block diagram form. FIG. 8 shows a measurement module 90 which receives a glucose strip 92 for measuring a glucose level of blood applied to the strip 92. The measurement module 90 communicates with the PDA which may be running a Palm operating system or other PDA operating system software. The measurement module 90 is preferably configured to turn off nonessential electronics when no measurement is being made. The measurement module preferably includes a microprocessor that controls internal timing, algorithms, result calculation and fault determination, among other responsibilities. The module 90 includes circuitry to connect the serial output of its internal microprocessor to PDA electronics including a mechanism for program initiation and data transfer. The module 90 also preferably provides electronic ESD protection on analog strip connector lines and flash memory for storage of meter firmware and associated user preferences. The module 90 is preferably powered by the PDA, but could alternatively include its own power source, such as button or AAA-size batteries. The module 90 includes electrical isolation between the strip connector and the HotSync port.

The PDA communicates with a PC when the PDA is preferably HotSynced to the PC. The PDA includes RAM as a temporary database for diabetes management application data and/or programs and non-volatile memory for permanent data and/or program storage. The measurement of the glucose level may however be advantageously performed when the PDA is not HotSynced to the PC, and the PDA includes many data processing features itself for managing data without support from the PC. For example, charts and/or graphs may be generated on the PDA display. The PC system includes standard peripheral devices such as a monitor 98, keyboard 100, CD-rom 102 and a printer 104.

Figure 9:
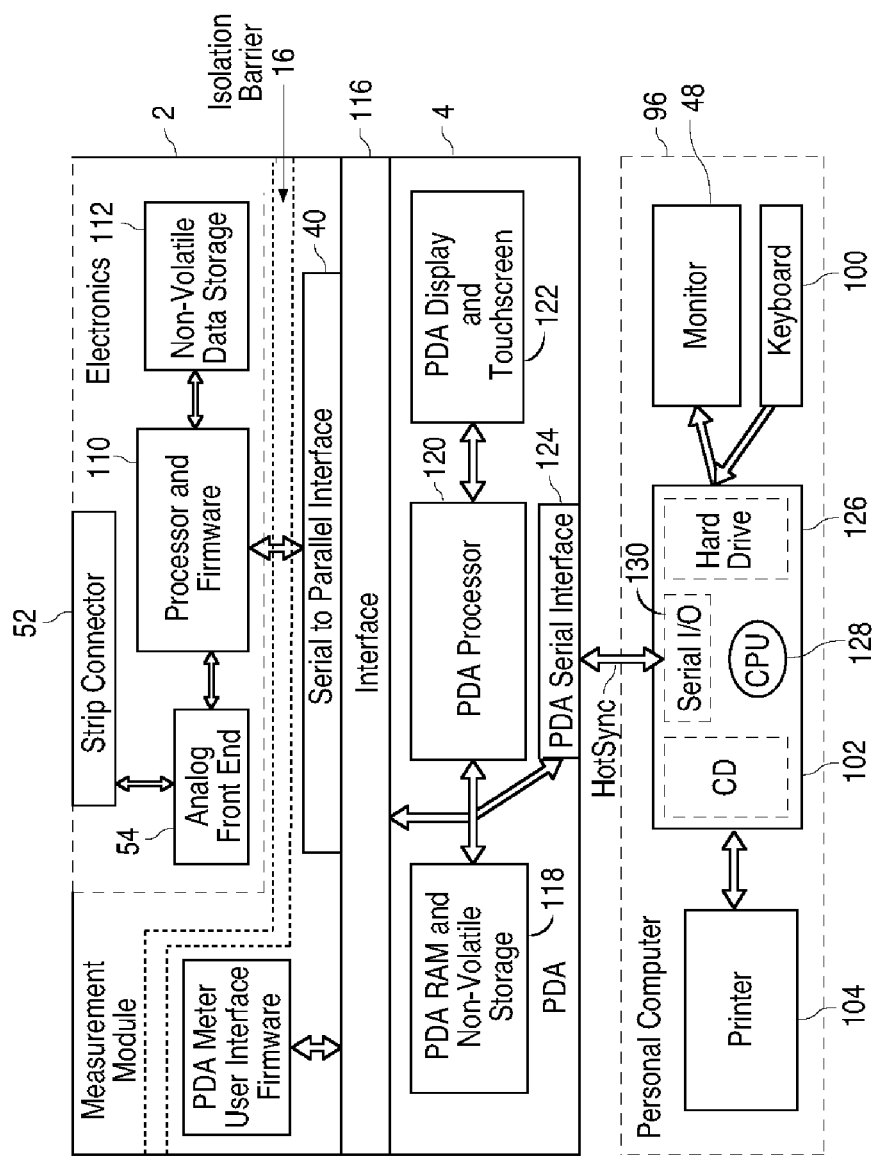
FIG. 9 illustrates a hardware/software block diagram of an integrated glucose measurement module and PDA according to a preferred embodiment.

FIG. 9 illustrates a hardware/software block diagram of an integrated glucose measurement module 2 and PDA 4 according to a preferred embodiment. The measurement module 2 shown includes a strip connector 52 and analog front end electronics 54, such as those shown in FIG. 4. The measurement module 2 also shows a processor running firmware 110, wherein the processor may be as the processor 56 shown in FIG. 4. The processor is shown having access to non-volatile data storage 112. The isolation barrier 16 is shown wherein the above-mentioned components of the measurement module 2, i.e., the strip connector 52, analog front end electronics 54, processor and firmware 110 and non-volatile data storage 112, are on the isolated side of the barrier 116. PDA meter user interface firmware 114 permits the module 2 to communicate with the PDA 4. A serial to parallel interface, such as that shown in FIG. 2, is also shown in FIG. 9 for converting the serial data transmitted across the barrier 16 using optoisolators 68, 70 such as those described above with respect to FIG. 5. An interface 116 is shown between the module 2 and PDA 4.

The PDA 4 is shown having a PDA RAM and non-volatile storage 118, a PDA processor 120, a PDA display and touchscreen 122 and a PDA serial interface 124. The PDA is configured to HotSync to a PC system 96, such as that described above with respect to FIG. 8, including a monitor 98, keyboard 100, CD-rom 102 and printer 104. The PC system shown in FIG. 9 also includes a hard drive 126, a CPU 128 and a serial I/O 130 which alternatively may be USB.

The data may be entered on the PDA 4. This data may be HotSynced to the PC 96. The data may also be entered on the PC 96 and reverse HotSynced to the PDA 4. In the former case, e.g., the PC 96 would have an application stored in its memory for accepting this data. This PC application would display and print logbook data in various formats. The PC application would also export data to various data processing applications. The application may use a Microsoft Access Database or MDB format, while the data on the PDA may be stored using the Palm PDB format.

The user is preferably able to reverse HotSync data from the PC in order to restore the data to the state it was when it was last HotSynced. The user might want to do this in the event the database on the PDA becomes corrupted. The PC application and database may store a complete history of data that was entered on the PDA. The PDA user may choose to archive some of the PDA data on the PC.

A conduit program may be used. The program may perform the following steps: (1) create a replica of the data stored on the PDA, on the PC; and (2) synchronize data from the PDA to the database on the PC. The two steps may be performed in two separate conduit programs. Synchronizing the data may include reading data from a PDB file and writing it to the PC database. Microsoft Visual Studio may be used for opening, reading and writing data in the PC database. The data may be read from the PDA, matched to data on the PC, format converted, and written to the PC database. Similarly, data entered or modified on the PC may be matched to data on the PDA. The data on the PDA may be updated to reflect the changes made on the PC.

To match data from the PDA to the PC, unique ID numbers may be used in records on the two systems. These ID numbers may be created on the PDA as logbook records or on the PC as logbook entries there. The uniqueness of the ID numbers may be achieved by pre/post fixing the ID with an origin code identifying PC or PDA, or alternatively perhaps a GUID.

To read data from a PDA file and write it to the PC database, it is recognized herein that data in the PC database may be organized into tables, which may be organized into records, which may be broken down into predefined fields. Similarly, at some level data will be organized into records with a consistent field structure on the PDA.

The conduit program reads the data from the PDA file(s) and writes it out to PC tables. The conduit program also reads data from the PC tables and writes them out to PDA file(s). Various types of data conversion may be used. For example, data residing in fields in the PDA file may be converted from the format it exists in the PDA file to a format compatible with the PC and vice-versa. The logical structure of the records in the two systems may be different. Tables may be created (either in code or in an external file such as a database) which define the mapping of data in fields of one system to data in fields in the other. Data may be stored in temporary table(s) that may later be synchronized with main table(s) that contain a complete logbook history, or the conduit program may write to these tables directly.

Figure 10:
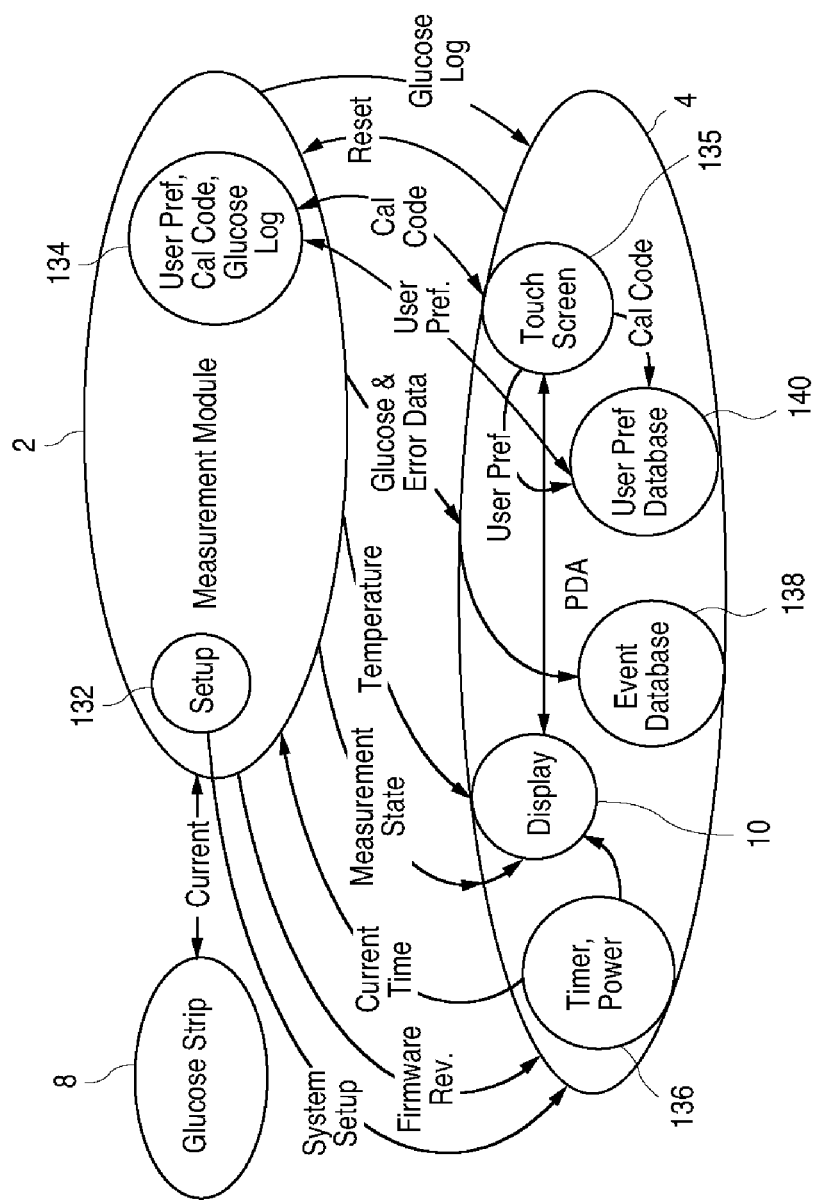
FIG. 10 shows a data flow diagram of an integrated glucose measurement module and PDA according to a preferred embodiment.

FIG. 10 shows a data flow diagram of an integrated glucose measurement module 2 and PDA 4 according to a preferred embodiment. Current is flowed to a strip 8 from the measurement module 2 which, as mentioned, is powered by the PDA 4 as shown and described with respect to FIG. 5. The measurement module 2 includes a setup component 132, which the module 2 communicates to the PDA 4, and a user preferences, calibration code and glucose log component 134. Component 134 serves to convert an electrical reading, such as the current that passes through the blood on the strip 8, to a glucose level, saves a glucose log, saves user preferences, and provides status and error data to the PDA 4. Error data may include glucose errors and charge errors. The PDA 4 is also configured to send user preferences and a calibration code to the measurement module 2 for use or storage by the component 134.

The PDA 4 also receives firmware revision data, measurement state data and temperature data from the measurement module 2. The measurement state and temperature are preferably displayed on a display 10 of the PDA 4 or otherwise provided to a patient by sensory output such as audio or vibration output. The display 10 is preferably also configured to function with touchscreen software and electronics 135. The PDA 4 includes a timer and power module 136, information about which is also displayed. Data regarding the current time is also sent to the module 2 from the timer and power module 136 of the PDA 4.

The PDA advantageously also includes an event database 138 and a user preferences database 140. The event database 138 generally includes information relevant to diabetes management, such as glucose readings. Fields of an event may include time, data, event type. The glucose and error data are stored to the event database 138 after the PDA 4 receives the data from the module 2. The event database includes a logbook which collects glucose, insulin, carbohydrate and exercise data and time. The data in the event database 138 may be graphed in many ways according to helpful default or pre-programmed graphs or according to filtering and preferences inputs from a user. Some exemplary graphs that may be generated on the PDA display 10 from the event database and software loaded on the PDA without the PDA being HotSynced or otherwise connected to a PC or other processing device. In addition, the data including glucose data is automatically sent to the PDA 4 from the module 2 to be stored in the event database 138 where the data can be used to generate graphs that help a user such as a diabetes patient to track glucose and other information. The data measured by the module 2 does not need to be manually entered by the user into a computer before the data can be processed into graphs and the like, or so that the PDA's own software can process or analyze the data to provide useful data analysis to the patient regarding the glucose and other information relating to the condition of the patient. Software on the PDA also preferably includes insulin and carbohydrate tools, and software for communicating with a PC. The user preferences database 140 may store user input such as units of measure, date and time format, an audible or otherwise sensory alert level, the language to be used and other user preferences.

The PC 96 such as that schematically shown at FIGS. 8 and 9 may have additional features. For example, the PC may be configured for viewing and printing the logbook stored on the PDA 4 and transferred to the PDA 4. The PC may be configured to take glucose values and put them into a data management database of its own that may have the same or different capabilities as the event database loaded on the PDA 4. The PC would be helpful for backing-up data and for downloading applications programs to the PDA and also for communicating with other computers over one or more networks. Additional data processing features of the system of the preferred embodiment herein are set forth below with reference to FIG. 11.

Figure 11:
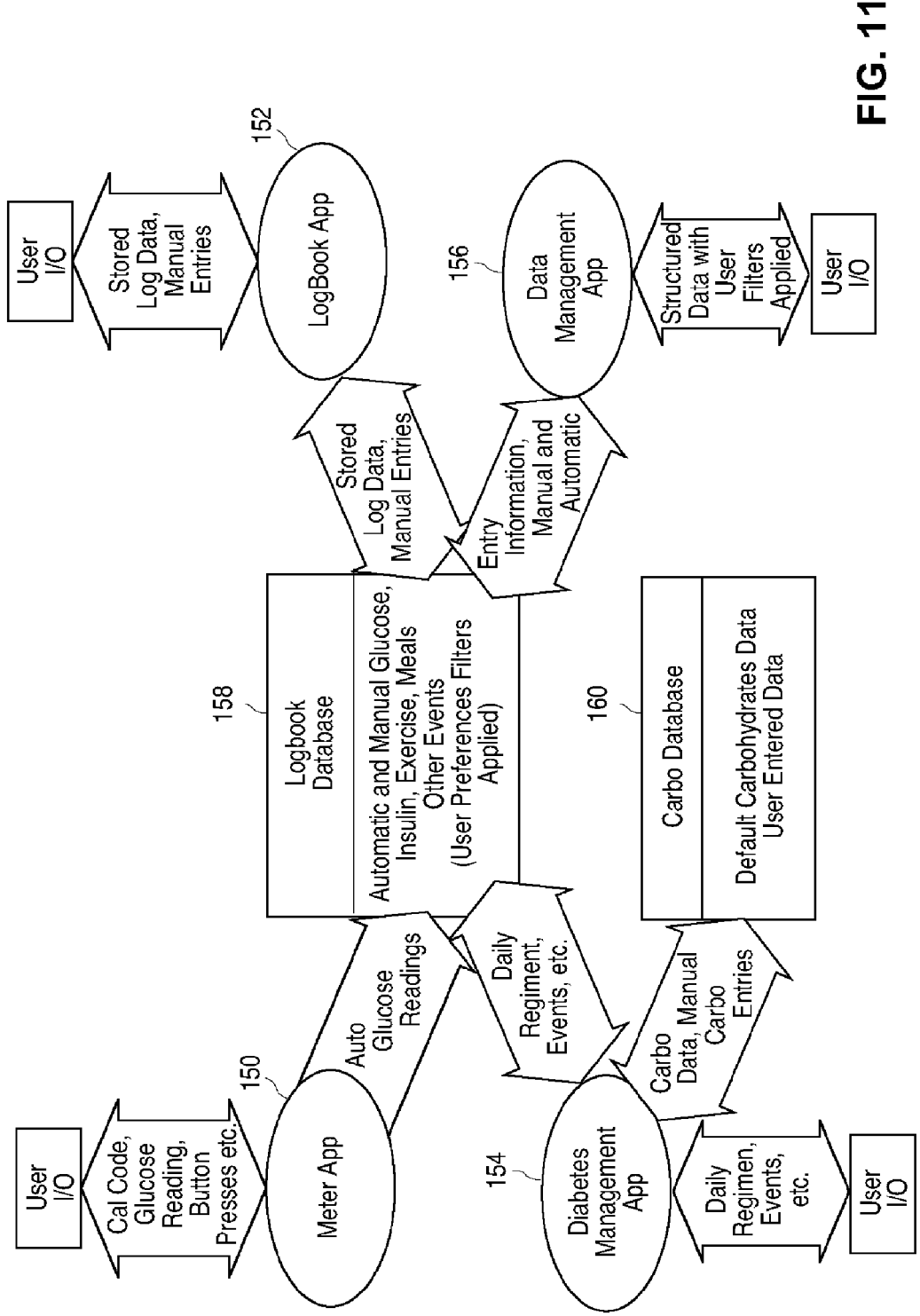
FIG. 11 shows a software data flow diagram of an integrated glucose measurement module and PDA according to a preferred embodiment.

FIG. 11 shows a software data flow diagram of an integrated glucose measurement module 2 and PDA 4 according to a preferred embodiment. FIG. 11 shows how four software applications according to a preferred embodiment interact and illustrate functions of these applications and databases that the applications are programmed to utilize. The applications include a meter application 150, a logbook application 152, a diabetes management application 154 and a data management application 156. Each of these applications preferably runs on the PDA which has been described above (e.g., see FIG. 10). These applications may also each run on a PC to which the PDA is configured to communicate. The applications may be downloaded to the PDA or another device from the PC or a server or other digital data storage device such as a CD-rom or magnetic disk.

FIG. 11 also shows a logbook database 158 and a carbohydrate ("carbo") database 160. The databases 158 and 160 are generally electronic stored records. These may be separate databases or parts of a same database. The logbook and carbo databases may be part of the event database 138 mentioned above with reference to FIG. 10. The logbook database 158 is preferably utilized by each of the applications 150, 152, 154 and 156 mentioned above and shown in FIG. 11, and includes automatic and manual glucose entries, insulin, exercise, meal and other data, and applies user preference filters. The carbo database 160 is preferably utilized by the diabetes management application 154, and includes default carbohydrate data and user entered data. Diabetes management generally refers to activities performed by an individual with diabetes to organize and optimize aspects of life with diabetes such as medication, diet, and exercise that are involved in treating and managing the diabetic condition. The diabetes management application facilitates these activities for the diabetic. The data management application generally provide graphic representations and/or text summaries of data relevant to diabetes management.

The logbook database 158 preferably includes time and date tagged events which are automatically or manually stored such as glucose measurements, manually entered glucose readings, exercise records, insulin injection records, meal time records, state of health records, note records, and medication among others. The user may input entries to the logbook database 158, e.g., that are derived from other glucose meters. Manually entered glucose readings may be flagged as user input rather than meter input. The user may enter other items such as insulin amount, type, and time period, meal times and carbohydrate values, exercise time, type, and degree of exertion (e.g., high, medium, low), state of health, comments and medications. These items may be available to the user from a predefined drop down list that can be edited and added to, or can be manually entered. Data associated with a past event may be entered or modified in the database 158 by the user. Events may be tagged with time periods.

Each application 150-156 is configured to process user inputs including glucose measurements. For example, the meter application is configured to process calibration code input, glucose readings and button presses. The glucose readings are advantageously automatically stored in the logbook database 158 on the PDA according to the programming of the meter application 150. The logbook application 152 is configured to process stored log data and manual entries, and to store and retrieve the log stored log data and manual entries into and from the logbook database 158, respectively. The diabetes management application 154 is configured to process a daily regimen and events such as exercise, meals, insulin dosages and times, etc. and to store and retrieve the daily regimen and events into and from the logbook database 158, respectively. The diabetes management application 154 is also configured to store and retrieve carbo data and manual carbo entries into and from the carbo database 160, respectively. The data management application 156 is configured to process structured data with user filters applied, and to store and retrieve automatic and manual entry information into and from the logbook database, respectively.

The data management application 156 may be configured to allow the user to view data summaries in graphical and text formats. The user may be able to select the length of time to be viewed. The user may also be able to set a default length of time to be viewed from within user preferences. The user may be able to view a complete data set or filter the screen display to show only a selected time period to view. The user may be able to select the event type to be displayed, more than one event type may be selected to be displayed simultaneously. Glucose summary statistics may be displayed by a selected date range and time period. Both selected date range and time period may appear on the display. The summary statistics may include the number of measurements, the highest measurement, the lowest measurement, the average measurement, the standard deviation of the measurements, the percentage of measurements within the target range, the percentage of measurements above the target range, the percentage of measurements below the target range, and insulin and carbohydrate statistics summary. Graphical summaries may also be provided such as line graphs and pie charts (see FIGS. 12-13). The user may be able to select a point on a line graph and see the logbook entry associated with that point.

The diabetes management application 154 may be configured with diabetes management tools such as carbohydrate tables, insulin tables, fast acting carbohydrate list, daily regimen (food and exercise patterns) and target glucose levels. The application 154 may process one or more carbohydrate tables and a food database. The user may be able to choose entries from a database listing carbohydrate values of foods per listed serving size. The user may be able to customize the food database by adding food items to the food database. The user may be able to tag entries as "quick picks". The diabetes management application 154 may include a lookup table containing the dose of insulin required to lower glucose concentration by a known amount.

The user may input insulin dosages based on a health care professional's recommendations.

One or more of the applications 150-156 may be configured to issue "alerts". These alerts may be warnings directed to the user that are audible, or otherwise sensory such as by vibration, and displayed with graphics and/or text using the display screen on the PDA. Alerts may indicate that a planned activity is due to begin. Event markers may be used to indicate that the user makes an entry into the logbook 158 to designate a specific condition or incident that relates to a specific blood glucose measurement such as meals, time before or after exercise, medication taken, sickness, feeling hypoglycemic, etc. The applications 150-156, and particularly the diabetes management application 154, may be used for self-monitoring of glucose in whole blood, and may be used by people with diabetes and by healthcare professionals as an aid to monitor the effectiveness of diabetes management.

The applications 150-156, and particularly the meter application 150, may be used to provide direction to a user taking a glucose measurement and control data flow to the logbook 158. For example, when the user inserts a test strip into the module, the module is programmed to check the strip and perform a self test. The display then indicates to the user when to apply the blood. The user then applies the blood sample to the strip. The measurement module monitors for fill (the PDA may, e.g., beep on fill) and takes the measurement. The module is programmed to then determine the glucose level and the PDA displays the result. The glucose value is then automatically entered into the electronic logbook, i.e., without user intervention, and the meter waits for further user input. Once the glucose measurement is complete, the meter application 150 may be configured to relinquish control to one or more of the other applications 152-156.

Figure 12:
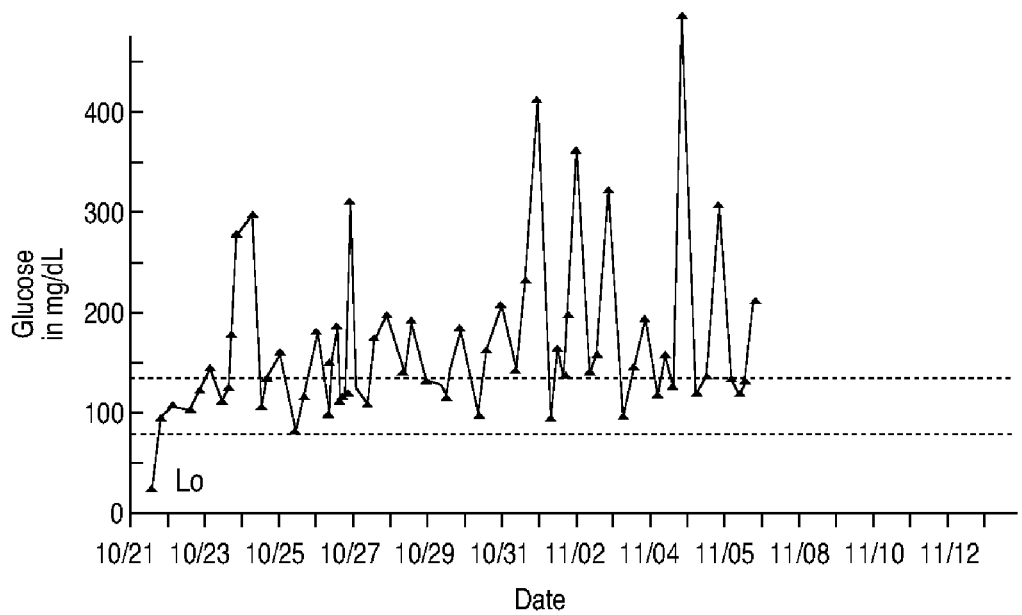
FIG. 12 illustrates a line graph of blood glucose data generated by an integrated measurement module and PDA according to a preferred embodiment.

FIG. 12 illustrates a line graph of blood glucose data generated by an integrated measurement module and PDA according to a preferred embodiment. The data used to generate this graph is stored in the logbook database. The line graph of FIG. 12 shows glucose levels according to the date that the glucose level was taken. As shown, a glucose level that was recorded on November 5 at around 500 mg/dL is labeled as being "Hi" while a glucose level recorded on October 21 at around 20 mg/dL is labeled as "Lo". A range between around 80 mg/dL and 140 mg/dL is indicated by dashed lines in FIG. 12 suggesting an optimal glucose level range.

Figure 13:
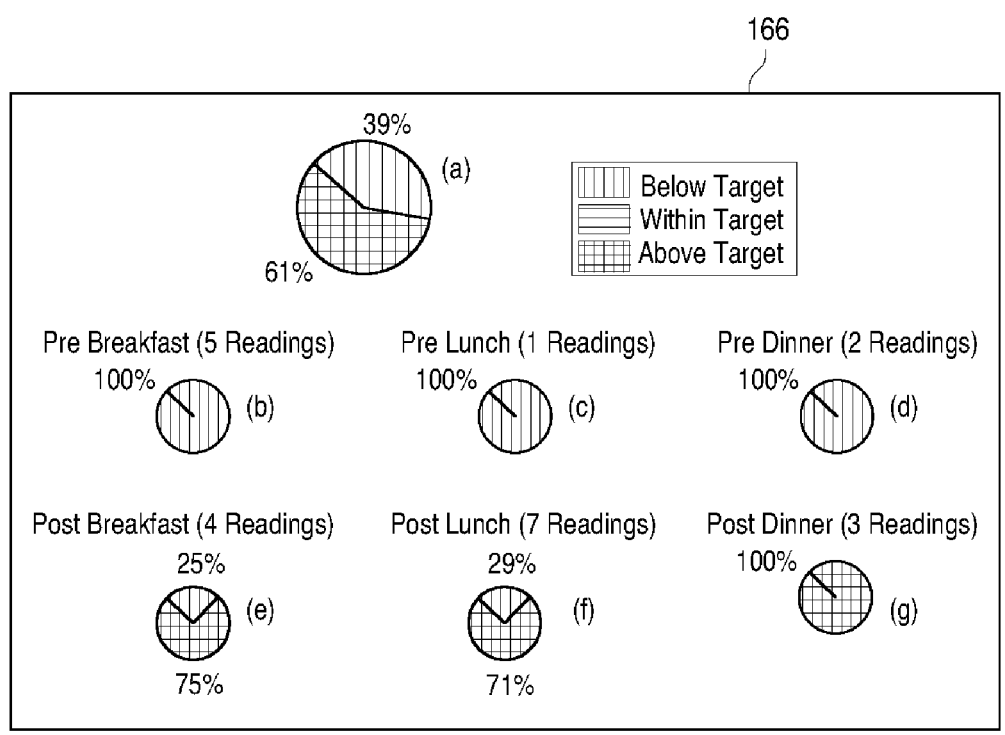
FIG. 13 illustrates pie charts of blood glucose data generated by an integrated measurement module and PDA according to a preferred embodiment.

FIG. 13 illustrates pie charts of blood glucose data generated by an integrated measurement module and PDA according to a preferred embodiment. The data used to generate the illustrative graphs of FIG. 13 is stored in the logbook database. All of the pie charts shown in FIG. 13 may be displayed on a display screen 166 of the PDA at the same time, or one or more may be displayed at a single time. The graphs show the percentage of readings that are below, within or above target. For example, chart (a) shows that overall 39% of the time the readings are within target or within the optimal glucose level range of FIG. 12. Charts (b)-(g) show the percentages of readings that are below, within or above target pre-breakfast, pre-lunch, pre-dinner, post-breakfast, post-lunch and post-dinner, respectively. The user can understand his or her glucose level trends from these graphs.

As described above, the advantageous glucose measurement module 2, as schematically shown, e.g., at FIG. 1, including its rounded-contour, tapered-shape narrowed end portion protruding from an inset shoulder of a connector end, and its composition, facilitates off-finger or alternate site testing. The strip 8, and/or any of various embodiments thereof are described at PCT published application No. WO 01/33216 and U.S. patent application Ser. No. 09/434,026, which are assigned to the same assignee as the present application and are hereby incorporated by reference. For example, the invention may use an electrochemical coulometric test strip such as the FreeStyle brand strip sold by TheraSense, Inc. of Alameda, Calif. The FreeStyle strip uses a so-called "side-fill" arrangement.

"Coulometry" is the determination of charge passed or projected to pass during complete or nearly complete electrolysis of the analyte, either directly on the electrode or through one or more electron transfer agents. The charge is determined by measurement of charge passed during partial or nearly complete electrolysis of the analyte or, more often, by multiple measurements during the electrolysis of a decaying current and elapsed time. The decaying current results from the decline in the concentration of the electrolyzed species caused by the electrolysis. "Amperometry", another method of electrochemically measuring glucose, includes steady-state amperometry, chronoamperometry, and Cottrell-type measurements.

While exemplary drawings and specific embodiments of the present invention have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention as set forth in the claims that follow, and equivalents thereof.

In addition, in the method claims that follow, the steps have been ordered in selected typographical sequences. However, the sequences have been selected and so ordered for typographical convenience and are not intended to imply any particular order for performing the steps, except for those claims wherein a particular ordering of steps is expressly set forth or understood by one of ordinary skill in the art as being necessary.

What is claimed is:

1. A glucose monitoring apparatus, comprising:
    a measurement module having
        a measurement module housing,
        a test strip receptacle formed at a first end of the of the measurement module housing,
        electronics for determining the amount of glucose present in a sample of blood placed on a test strip that is received in the test strip receptacle,
        a connector portion at a second end of the measurement module, and
        an isolated power module disposed within the measurement module;
    a processing device having a housing, wherein the measurement module is detachably integrated with and protrudes from the housing of the processing device, and wherein the measurement module housing is narrowed at the first end compared with the second end;
    a power isolation barrier between the measurement module and the processing device; and
    a transformer-coupled power transfer circuit that bridges the power isolation barrier and thereby transfers isolated power from a power source in the processing device to the isolated power module in the measurement module;

wherein the processing device comprises a processor and computer readable medium comprising instructions when executed by the processor, cause the processor to:
measure glucose data of a sample applied to a glucose test strip inserted into the glucose test strip receptacle using instructions residing on the computer readable medium of the processing device,
provide a sensory output of a glucose level corresponding to the measured glucose data using a code residing on the processing device,
enter the measured glucose data into a database accessible by a diabetes management software program stored on the computer readable medium of the processing device, and
execute the diabetes management software program whether or not the measurement module is integrated with the processing device.

2. The apparatus of claim 1, wherein the processing device is a mobile phone, a PDA or a PDA/mobile phone combination.

3. The apparatus of claim 1, wherein the instructions when executed by the processor, further cause the processor to receive manual entries and integrating the manual entries into the database.

4. The apparatus of claim 1, wherein the instructions when executed by the processor, further cause the processor to generate a graph according to previously entered data filtering instructions.

5. A glucose monitoring apparatus, comprising:
a measurement module having
a measurement module housing,
a test strip receptacle formed at a first end of the of the measurement module housing,
electronics for determining the amount of glucose present in a sample of blood placed on a test strip that is received in the test strip receptacle,
a connector portion at a second end of the measurement module, and
an isolated power module disposed within the measurement module,
wherein a portion of the measurement module housing has a trapezoidal profile such that the first or second end of the measurement module housing is narrower than the opposite end;
a processing device having a housing, wherein the measurement module is detachably integrated with and protrudes from the housing of the processing device, and wherein the measurement module housing is narrowed at the first end compared with the second end;
a power isolation barrier between the measurement module and the processing device; and
a transformer-coupled power transfer circuit that bridges the power isolation barrier and thereby transfers isolated power from a power source in the processing device to the isolated power module in the measurement module;
wherein the processing device comprises a processor and computer readable medium comprising instructions when executed by the processor, cause the processor to:
measure glucose data of a sample applied to a glucose test strip inserted into the glucose test strip receptacle using instructions residing on the computer readable medium of the processing device,
provide a sensory output of a glucose level corresponding to the measured glucose data using a code residing on the processing device,
enter the measured glucose data into a database accessible by a diabetes management software program stored on the computer readable medium of the processing device, and
execute the diabetes management software program whether or not the measurement module is integrated with the processing device.

6. The apparatus of claim 5, wherein the processing device is a mobile phone, a PDA or a PDA/mobile phone combination.

7. The apparatus of claim 5, wherein the instructions when executed by the processor, further cause the processor to receive manual entries and integrating the manual entries into the database.

8. The apparatus of claim 5, wherein the instructions when executed by the processor, further cause the processor to generate a graph according to previously entered data filtering instructions.

9. A glucose monitoring apparatus, comprising:
a measurement module having
a measurement module housing having a trapezoidal profile such that a first end of the housing is narrower than a second end of the housing,
a test strip receptacle formed at the first end of the of the measurement module housing,
electronics for determining the amount of glucose present in a sample of blood placed on a test strip that is received in the test strip receptacle,
a connector portion at the second end of the measurement module, and
an isolated power module disposed within the measurement module;
a processing device having a housing, wherein the measurement module is detachably integrated with and protrudes from the housing of the processing device, and wherein the measurement module housing is narrowed at the first end compared with the second end;
a power isolation barrier between the measurement module and the processing device; and
a transformer-coupled power transfer circuit that bridges the power isolation barrier and thereby transfers isolated power from a power source in the processing device to the isolated power module in the measurement module;
wherein the processing device comprises a processor and computer readable medium comprising instructions when executed by the processor, cause the processor to:
measure glucose data of a sample applied to a glucose test strip inserted into the glucose test strip receptacle using instructions residing on the computer readable medium of the processing device,
provide a sensory output of a glucose level corresponding to the measured glucose data using a code residing on the processing device,
enter the measured glucose data into a database accessible by a diabetes management software program stored on the computer readable medium of the processing device, and
execute the diabetes management software program whether or not the measurement module is integrated with the processing device.

10. The apparatus of claim 9, wherein the processing device is a mobile phone, a PDA or a PDA/mobile phone combination.

11. The apparatus of claim 9, wherein the instructions when executed by the processor, further cause the processor to receive manual entries and integrating the manual entries into the database.

12. The apparatus of claim 9, wherein the instructions when executed by the processor, further cause the processor to generate a graph according to previously entered data filtering instructions.

* * * * *